United States Patent
Monte et al.

(10) Patent No.: US 8,530,512 B2
(45) Date of Patent: Sep. 10, 2013

(54) **BROAD SPECTRUM GRAM-POSITIVE ANTIMICROBIALS AND ANTHELMINTICS WITH EFFICACY AGAINST DRUG-RESISTANT STRAINS AND *MYCOBACTERIUM* SPECIES**

(76) Inventors: Aaron P. Monte, La Crosse, WI (US); M. Shahjahan Kabir, Milwaukee, WI (US); Marc A. Rott, Victory, WI (US); William R. Schwan, Onalaska, WI (US); James M. Cook, III, Whitefish Bay, WI (US); Jennifer A. Miskowski, La Crosse, WI (US); Ranjit Verma, Shorewood, WI (US); Leah Defoe, Punta Gorda, FL (US)

( * ) Notice: Subject to any disclaimer, the term of this patent is extended or adjusted under 35 U.S.C. 154(b) by 234 days.

(21) Appl. No.: 12/973,078

(22) Filed: Dec. 20, 2010

(65) Prior Publication Data

US 2011/0092578 A1    Apr. 21, 2011

Related U.S. Application Data

(63) Continuation-in-part of application No. 11/697,582, filed on Apr. 6, 2007, now abandoned, which is a continuation-in-part of application No. 11/163,421, filed on Oct. 18, 2005, now abandoned.

(60) Provisional application No. 61/295,384, filed on Jan. 15, 2010, provisional application No. 60/522,587, filed on Oct. 18, 2004.

(51) Int. Cl.
*A61K 31/38* (2006.01)
*A61K 31/34* (2006.01)
*A61K 31/404* (2006.01)

(52) U.S. Cl.
USPC ............ 514/443; 514/438; 514/720; 549/52; 549/55; 549/58; 549/78; 568/45; 568/49; 568/633; 568/646

(58) Field of Classification Search
None
See application file for complete search history.

(56) References Cited

U.S. PATENT DOCUMENTS 6,814,960 B1 * 11/2004 Holzl et al. ................... 424/65

OTHER PUBLICATIONS

Choi et al. (The Korean Journal of Parasitology, vol. 17, No. 1, Jun. 1979, pp. 60-66).*

* cited by examiner

*Primary Examiner* — Rosalynd Keys
(74) *Attorney, Agent, or Firm* — Boyle Fredrickson, S.C.

(57) ABSTRACT

The present invention provides compounds and methods of using of the compounds as anti-infective and anthelminitc agents. In a preferred embodiment, the present invention provides the following compound of Formula III:

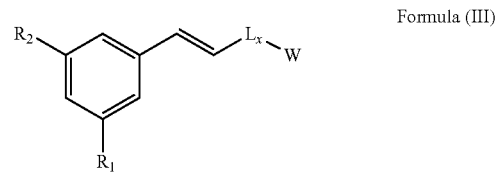

Formula (III)

wherein:
$R_1$ is not H when $R_2$ is H and $R_2$ is not H when $R_1$ is H, further wherein $R_1$ is OH or $CH_{(2n+1)}O$, wherein n is 1-10;
$R_2$ is OH or $CH_{(2n+1)}O$, where n is 1-10;
W is alkyl, phenyl, halophenyl, pyridyl, piperidyl, or a substituted or unsubstituted aryl group, including unsubstituted and substituted aromatic heterocycles; and
L is an optional linker or linking group selected from O, S, NH, $CF_2$, or $CH_2$, and x=0 or 1, i.e., if x=0, no linking group is present and when x=0, W is not phenyl.

13 Claims, 16 Drawing Sheets

```
CURRENT DATA PARAMETERS
USER              PRESCHER
NAME                 MONTE
EXPNO                    1
PROCNO                   1

F2 ACQUISITION PARAMETERS
DATE_             20020928
TIME                 13.03
INSTRUM            DRK-500
PROBHD       5 mm MULTINU
PULPROG             IPULSE
TD                   65536
SOLVENT              CDCl3
NS                       8
DS                       0
SW              19.995 ppm
FIDRES        0.152588 Hz
AQ           3.2768500 sec
RG                   203.2
DE                7.11 usec
TE                 293.0 K
D1          0.03100000 sec ------CHANNEL F1------
NUC1                    1K
PQ                5.44 usec
PL1                -6.00 dB
SFO1      500.1321569 MHz F2 - PROCESSING PARAMETERS
SI                   65536
SF        500.1300127 MHz
WDW                     EM
SSB                      0
LB                 0.20 Hz
GB                       0
PC                   30.00
```

Fig. 2B

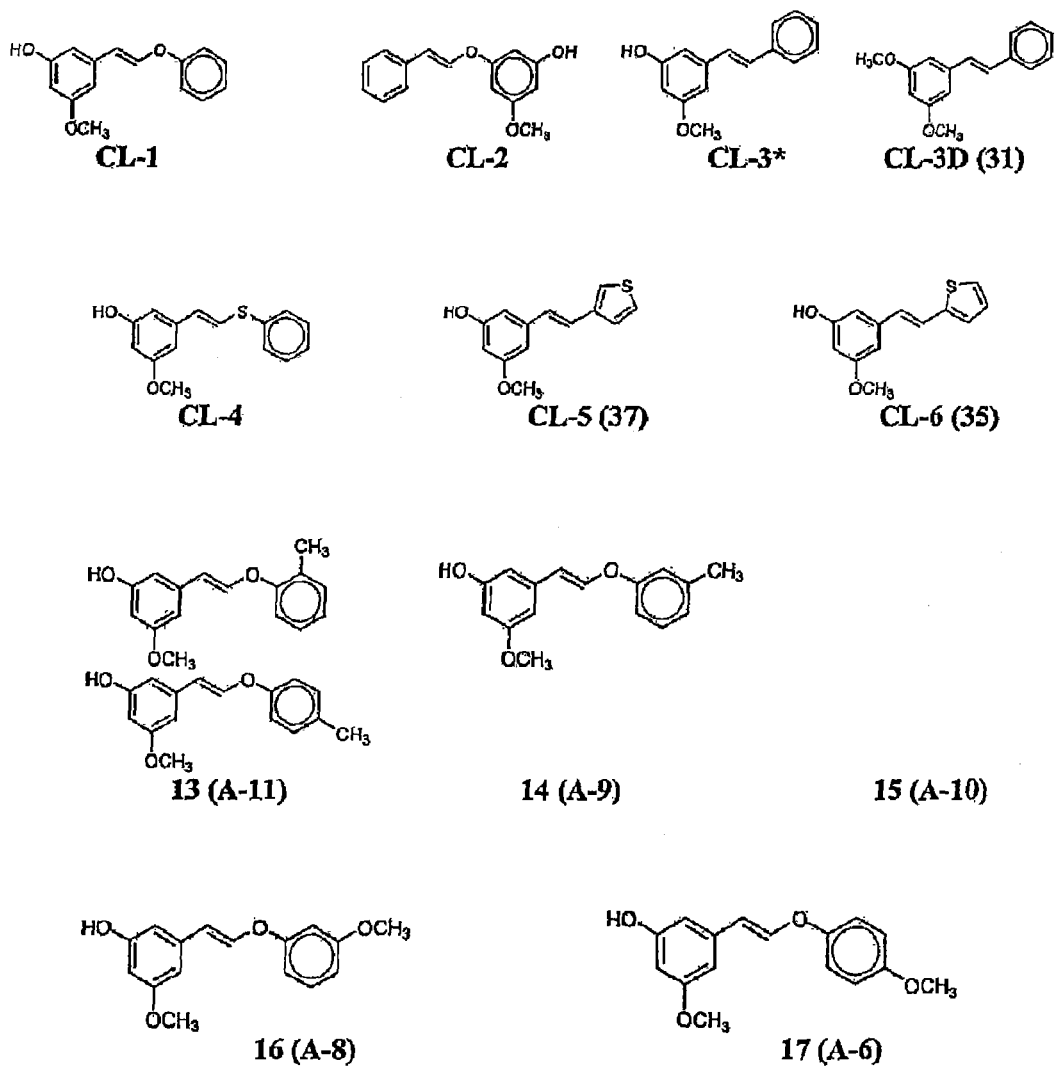
Figure 6. Compounds synthesized and assayed. Antimicrobial activity data for these compounds is shown in Table 1.

Figure 7F
Generic analogues
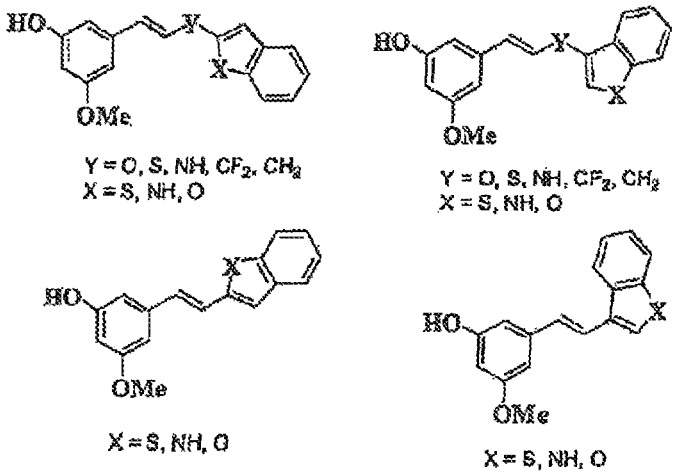
Cis and trans epoxides of all analogues in this work, as well as any enantiomers or diastereomers derived therefrom are contemplated herein:
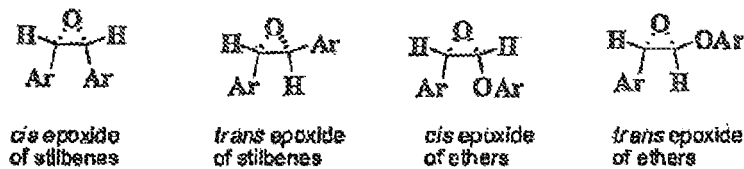
All compounds listed above with aromatic substitution patterns as such:
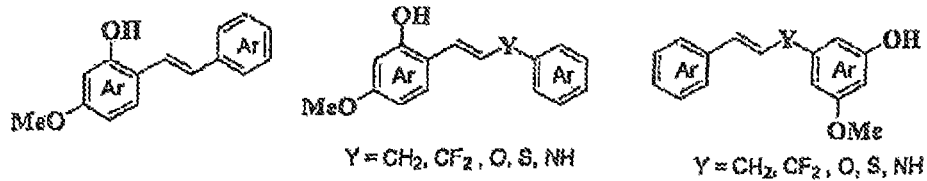
are also contemplated herein.

BROAD SPECTRUM GRAM-POSITIVE ANTIMICROBIALS AND ANTHELMINTICS WITH EFFICACY AGAINST DRUG-RESISTANT STRAINS AND *MYCOBACTERIUM* SPECIES

CROSS-REFERENCE TO RELATED APPLICATIONS

This application claims priority from U.S. Provisional Application Ser. No. 61/295,384, filed on Jan. 15, 2010, and as a continuation-in-part of U.S. Non-Provisional application Ser. No. 11/697,582, filed Apr. 6, 2007 now abandoned, which claims priority as a continuation-in-part of U.S. Non-Provisional application Ser. No. 11/163,421, filed on Oct. 18, 2005 now abandoned, which claims priority from U.S. Provisional Application Ser. No. 60/522,587, filed on Oct. 18, 2004, each of which are expressly incorporated by reference herein in their entirety.

TECHNICAL FIELD

Present invention generally relates to anti-infective agents and specifically to anti-infective agents isolated from Myricaceae family plants, especially *Comptonia peregrina* (sweet fern).

BACKGROUND

Myricaceae family plants typically include resinous trees or shrubs having evergreen or deciduous leaves. Family characteristics of plants of the Myricaceae family are well known and established. Such plants include *Comptonia peregrina, Comptonia ceterach, Myrica asplenfolia, Liquidamber peregrina, Myrica comptonia, Myrica peregrina, Gale palustris, Myrica gale, Myrica palustris, Myrica cerifera, Myrica pusilla, Cerothammus ceriferus* and *Cerothammus pusilla*.

*Comptonia peregrina* (L.) Coulter ("sweet fern") is a shrub of the Myricaceae family. It is also known as *Myrica asplenifolia* or *Myrica peregrina*. It is not actually a fern but a low deciduous rhizomatous shrub, with fernlike foliage. It is a woody plant found in the North Woods, New Brunswick, New England, the Great Lakes region, Saskatchewan, Georgia, and North Dakota.

Historically Mi'kmaq used the leaves to treat poison ivy rashes. Plant materials from *C. peregrina* have also been used as potpourri and tea for relieving symptoms of dysentery. Further, its fruits are eaten as food and the fresh leaves are used as lining for fruit baskets to preserve the fruits.

As well, the Ojibwe of northern Wisconsin and other Indian cultures as well as European settlers and more modern herbalists have used the leaves of this plant in the treatment of stomach ailments and dermatological problems, such as psoraisis, eczema and skin cancers. Previous chemical and biological investigations of this plant described in the literature have primarily focused on the volatile oil and flavonoid components of this plant.

For other diseases, such as bacterial diseases, antimicrobial resistance is an ever growing problem. For example, see comments by Linda Brenon on the FDA web site <http://www.fda.gov/fdac/ifeatures/2002/402_bugs.html>. Bacteria that resist not only single, but multiple, antibiotics have become increasingly widespread—making some diseases particularly hard to control. In fact, according to the Centers for Disease Control and Prevention (CDC), virtually all significant disease-causing bacteria in the world are becoming resistant to the antibiotic treatment of choice. For some patients, bacterial resistance could mean more visits to the doctor, a lengthier illness, and possibly more toxic drugs. For others, it could mean death. The CDC estimates that each year, nearly 2 million people in the United States acquire an infection while in a hospital, resulting in 90,000 deaths. More than 70 percent of the bacteria that cause these infections are resistant to at least one of the antibiotics commonly used to treat them.

Antibiotic resistance, also known as antimicrobial resistance, is not a new phenomenon. Just a few years after the first antibiotic, penicillin, became widely used in the late 1940s, penicillin-resistant infections emerged that were caused by the bacterium *Staphylococcus aureus* (*S. aureus*). These "staph" infections range from urinary tract infections to bacterial pneumonia. Methicillin, one of the strongest in the arsenal of drugs to treat staph infections, is no longer effective against some strains of *S. aureus*. Vancomycin, which is the most effective drug against these resistant pathogens, may be in danger of losing its effectiveness; recently, some strains of *S. aureus* that are resistant to vancomycin have been reported.

Although resistant bacteria have been around a long time, the scenario today is different from even just 10 years ago, as suggested by the Alliance for the Prudent Use of Antibiotics. The number of bacteria resistant to many different antibiotics has increased, tenfold or more. Even new drugs that have been approved are confronting resistance, fortunately in small amounts.

Accordingly, the need exists for further investigating new drugs such as antibiotics, antimicrobials, anthelmintics, compounds and derivatives, which have so far not been discovered to counter increasing bacterial resistance of currently known compounds and derivatives. Of course, the compounds and derivatives of the present invention may be used in a multitude of situations where these anti-infective and/or anthelmintic properties and capabilities are desired. Thus, the present invention should not be interpreted as being limited to application in connection with those preferred embodiments described in the present invention.

SUMMARY OF THE INVENTION

The present invention provides a compound of Formula I, or a salt or prodrug. Generally, the compound, salt or prodrug is an anti-infective and/or anthelmintic agent useful for the treatment of disease caused by bacteria, and preferably, Gram-positive bacteria, or in the immobilization or inhibition of growth of helminths.

Formula I is described as follows:

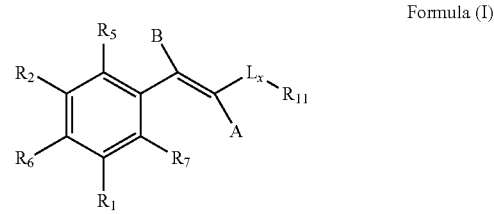

wherein:
$R_1$ is not H when $R_2$ is H and $R_2$ is not H when $R_1$ is H, further wherein $R_1$ is $CH_{(2n+1)}O$, wherein n is 1-10;
$R_2$ is OH or $CH_{(2n+1)}O$, wherein n is 1-10;
A, B and $R_1$, $R_2$, $R_5$, $R_6$, and $R_7$ are separately and independently selected from a group consisting of H, alkyl and aryl groups;
$R_{11}$ is an alkyl or an aryl group; and L is an optional linker or linking group, with x=0 or 1, i.e., if x=0, no linking group is present.

In one preferred embodiment, the compound, salt or prodrug is according to Formula II.

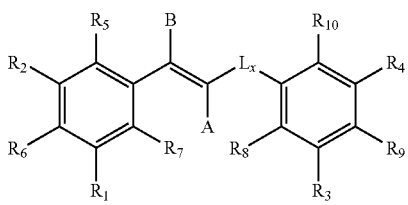

Formula (II)

wherein:
R$_1$ is not H when R$_2$ is H and R$_2$ is not H when R$_1$ is H, further wherein R$_1$ is CH$_{(2n+1)}$O, wherein n is 1-10;
R$_2$ is OH or CH$_{(2n+1)}$O, wherein n is 1-10;
A, B and R$_3$ through R$_{10}$ are separately and independently selected from a group consisting of H, alkyl and aryl groups; and
L is an optional linker or linking group, with x=0 or 1, i.e., if x=0, no linking group is present. In a preferred embodiment, L=1, and is —O-(oxygen).

In a preferred embodiment, R$_1$ is CH$_3$O and R$_2$ is OH or CH$_{(2n+1)}$O, wherein n is 1-10; and wherein A, B and R$_3$ through R$_{10}$ are separately and independently selected from a group consisting of H, alkyl and aryl groups.

In another preferred embodiment, R$_1$ is CH$_3$O, R$_2$ is OH and wherein A, B and R$_3$ through R$_{10}$ are separately and independently selected from a group consisting of H, alkyl and aryl groups.

Further, said compound, salt or prodrug may have an E or Z orientation. More preferably, the compound of Formula I is:

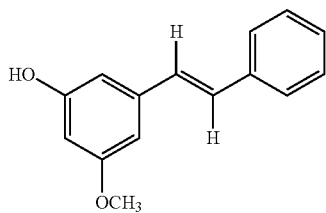 [SMILES: COc1cc(O)cc(/C=C/c2ccccc2)c1]

or a salt or prodrug thereof. Further, said compound, salt or prodrug may have an E or Z orientation.

In another embodiment, said anti-infective and/or anthelmintic compound, salt or prodrug is shown in Formula III as follows:

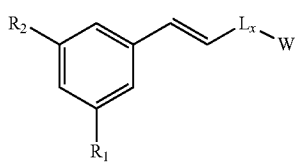

Formula (III)

wherein:
R$_1$ is not H when R$_2$ is H and R$_2$ is not H when R$_1$ is H, further wherein R$_1$ is OH or CH$_{(2n+1)}$O, wherein n is 1-10;
R$_2$ is OH or CH$_{(2n+1)}$O, where n is 1-10;

W is alkyl, phenyl, halophenyl, pyridyl, piperidyl, or a substituted or unsubstituted aryl group, including certain unsubstituted and substituted aromatic heterocycles; and
L is an optional linker or linking group selected from O, S, NH, CF$_2$, or CH$_2$, and x=0 or 1, i.e., if x=0, no linking group is present. The term "aryl" herein is to be broadly understood as is described below.

Another aspect of the invention teaches a method of isolating an anti-infective compound from a Myricaceae family plant. In one embodiment, the plant is *Comptonia peregrina, Comptonia ceterach, Myrica asplenfolia, Liquidamber peregrina, Myrica comptonia, Myrica peregrina, Gale palustris, Myrica gale, Myrica palustris, Myrica cerifera, Myrica pusilla, Cerothammus ceriferus* or *Cerothammus pusilla*. The method comprises the steps of (a) collecting a plant material (b) extracting crude extract from the plant material; and (c) isolating and purifying at least one anti-infective compound from the crude extract. Preferably, the plant material includes leaves of *C. peregrina* plant. Further, in a preferred embodiment, the isolation and purification are carried out by chromatography. In a more preferred embodiment, the isolated anti-infective compound is E-3-hydroxy-5-methoxy stilbene.

Yet another aspect of the present invention describes a method of treating infections or inhibiting microbial growth in a subject in need thereof, said method comprising the step of administering an effective amount of a compound having a structure represented by Formulas I, II or III or a salt or prodrug thereof. Such infections may be caused by a bacterium.

Another aspect of the invention provides a pharmaceutical composition, comprising: (a) an effective amount of a compound having a chemical structure represented by Formulas I, II or III, or a salt or a prodrug thereof; and (b) a pharmaceutically-acceptable carrier. The compound, salt or prodrug is an anti-infective agent useful for the treatment of disease caused by a bacterium.

Yet another aspect of the invention provides a method of inhibiting microbial growth. The method comprising contacting microbe to be inhibited with a microbial inhibiting amount of a compound according to Formula I, II or III, or salt or prodrug thereof.

Preferably the microbe to be inhibited is selected from the group consisting of: *Staphylococcus aureus, Staphylococcus epidermidis, Streptococcus pneumoniae, Enterococcus faecalis, Bacillus cereus, Helicobacter pylori, Bacillus megaterium, Bacillus subtilis, Corynebacterium pseudodiptherium, Corynebacterium diphtheriae* TOX.sup.-, *Corynebacterium xerosis, Enterococcus faecium* VRE 1, *Enterococcus faecium* VRE 14, *Enterococcus faecalis* ATCC 29212, *Staphylococcus aureus* ATCC 29213, *Staphylococcus aureus* ATCC 25923, *Staphylococcus aureus* MRSA MC-1, *Staphylococcus aureus* MRSA MC-4, *Streptococcus mitis, Streptococcus agalactiae, Streptococcus pyogenes, Streptococcus pneumoniae* ATCC 49619, *Listeria monocytogenes, Mycobacterium bovis* BCG, *Mycobacterium tuberculosis*, and *Bacillus anthracis*. Further, the microbe to be inhibited is a gram positive bacterium. In certain embodiments, the bacterium is a Gram positive bacterium, a *Mycobacterium* species, or *H. pylori*.

Another aspect of the invention provides a composition suitable for inhibiting growth of microbes. The composition comprises: a first ingredient which inhibits microbial growth comprising the compound, prodrug or salt of claim 1; and a second ingredient which comprises an acceptable carrier or an article of manufacture. In one embodiment, the acceptable carrier is a pharmaceutically acceptable carrier, an antibacterial agent, a skin conditioning agent, a lubricating agent, a coloring agent, a moisturizing agent, binding and anti-cracking agent, a perfuming agent, a brightening agent, a UV absorbing agent, a whitening agent, a transparency imparting agent, a thixotropic agent, a solubilizing agent, an abrasive agent, an antioxidant, a skin healing agent, a cream, a lotion, an ointment, a shampoo, an emollient, a patch a gel or a sol. In another embodiment, the article of manufacture is a textile, a fiber, a glove or a mask. Preferably, in the composition, the first ingredient is E-3-hydroxy-5-methoxy stilbene.

Another aspect of the present invention provides a composition suitable for immobilizing and/or adversely affecting the development of helminths or parasitic intestinal worms. The anthelmintic agent or composition comprises: a first ingredient which inhibits microbial growth comprising the compound, prodrug or salt of claim 1; and a second ingredient which comprises an acceptable carrier or an article of manufacture.

Yet another aspect of the invention describes a method of treating immobilizing or adversely affecting the development of helminthes in a subject in need thereof, said method comprising the step of administering an effective amount of a compound having a structure represented by Formulas I, II or III or a salt or prodrug thereof.

In sum, the present invention represents new compounds and methods of using these compounds for the treatment and prevention of various infections, parasitic organisms and growth of microbes. These and other objects and advantages of the present invention will become apparent from the detailed description accompanying the drawings.

BRIEF DESCRIPTION OF THE DRAWINGS

The drawings illustrate the best mode currently contemplated of practicing the present invention.

In the drawings.

Figure 1:
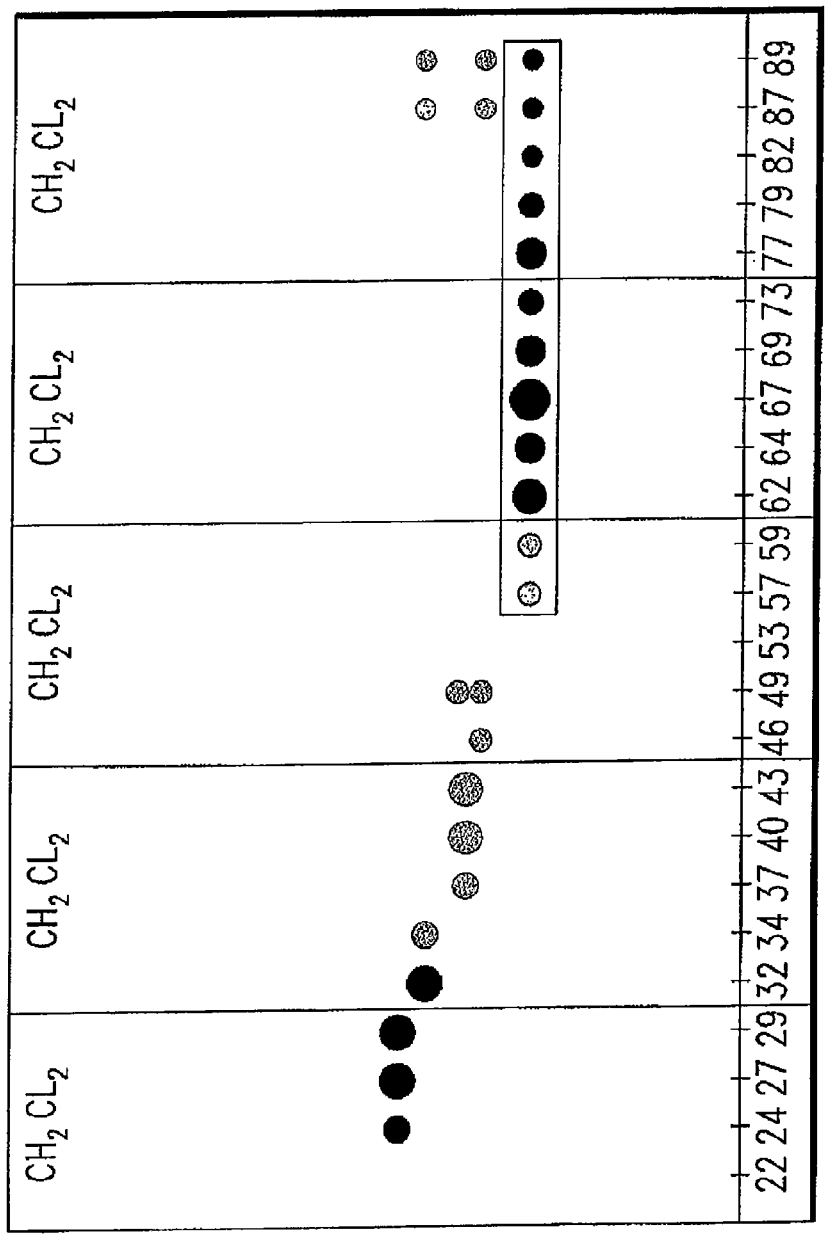
FIG. 1. TLC analysis of *C. peregrina* crude extract after flash column fractionation.
Figure 2A:
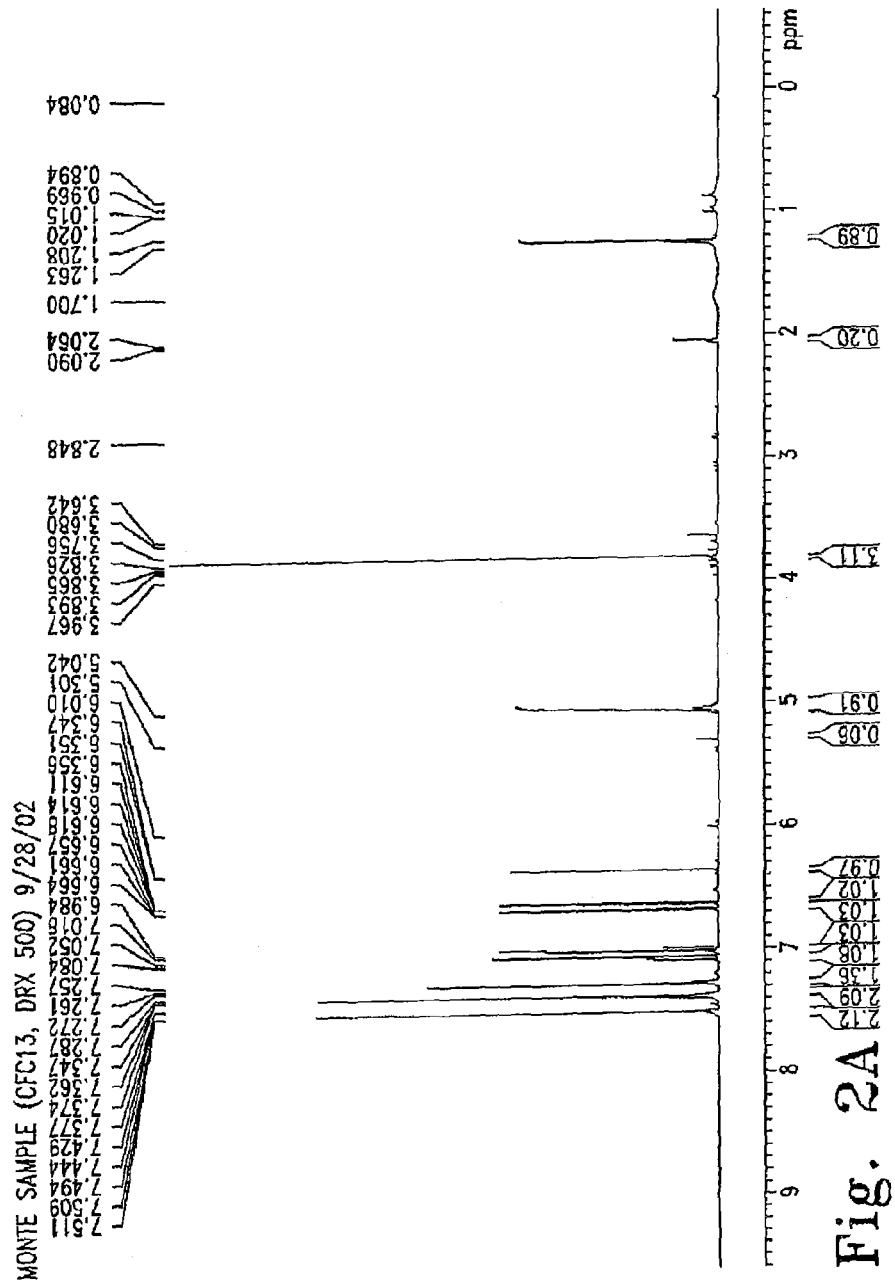
FIG. 2. $^{1}$H NMR spectrum of an isolated anti-infective compound from *C. peregrina.*
Figure 3:
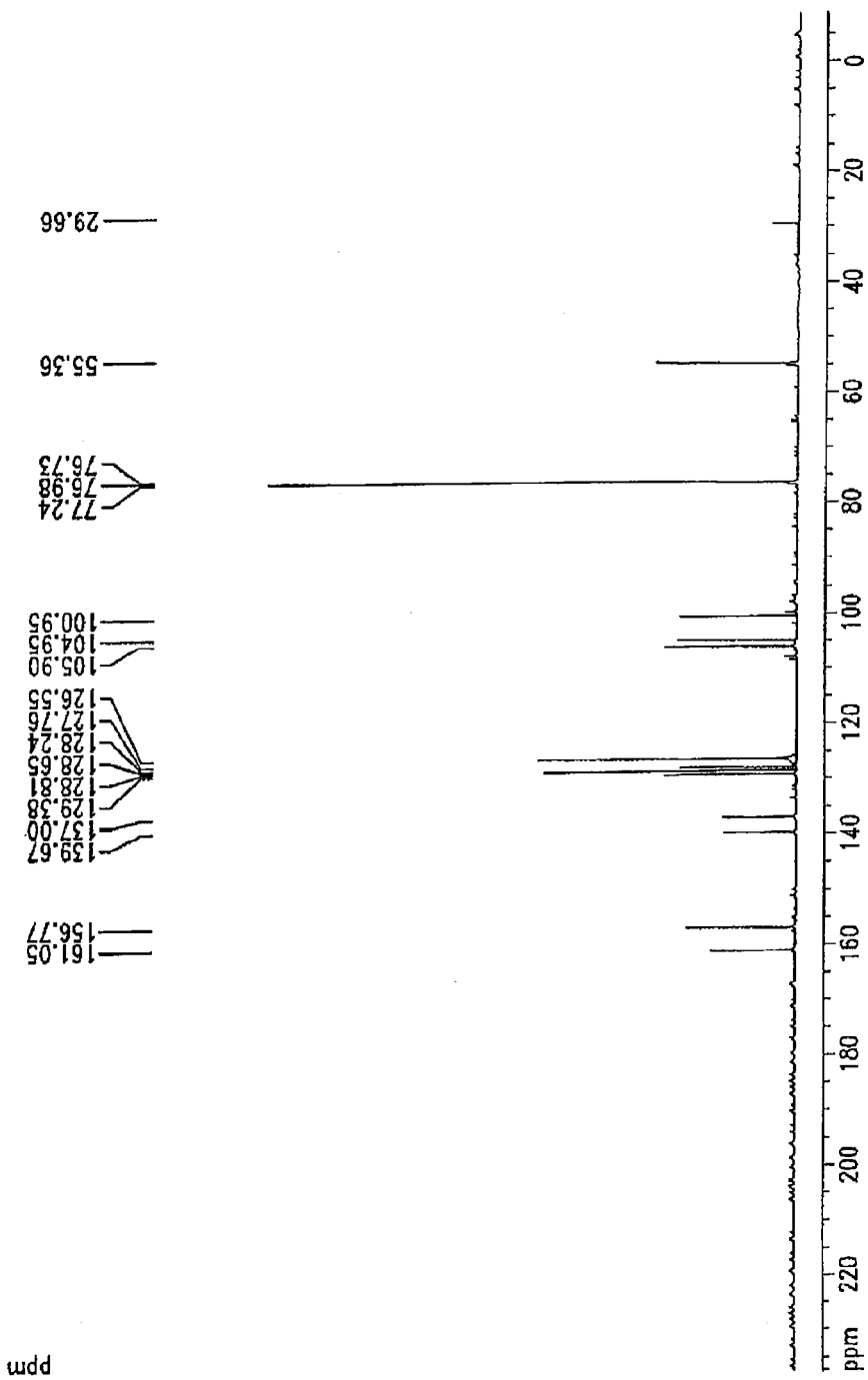
FIG. 3. $^{13}$C NMR spectrum of the isolated compound of FIG. 2.
Figure 4A:
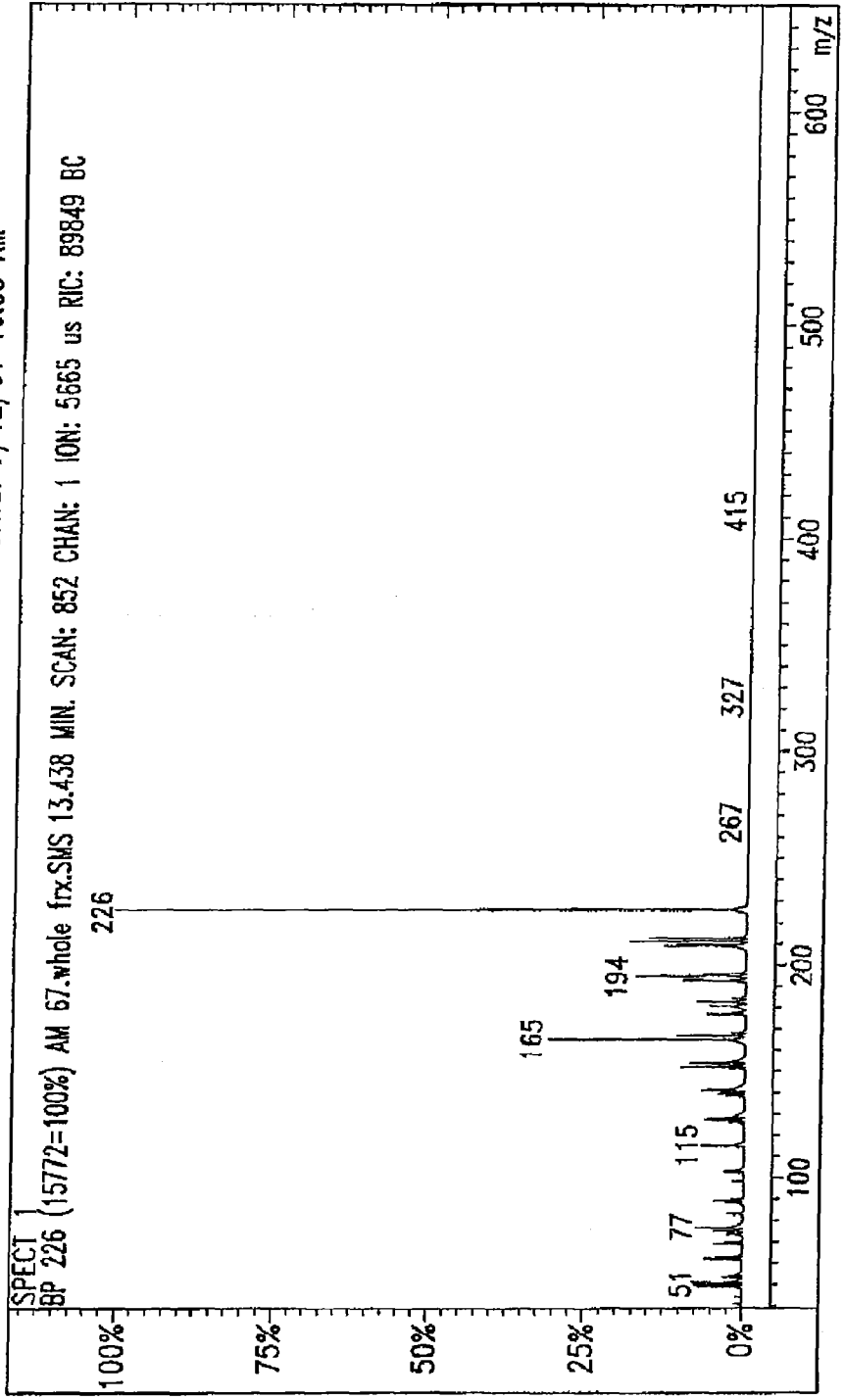
FIG. 4. GC-MS spectrum of the isolated compound of FIG. 2.
Figure 4B:
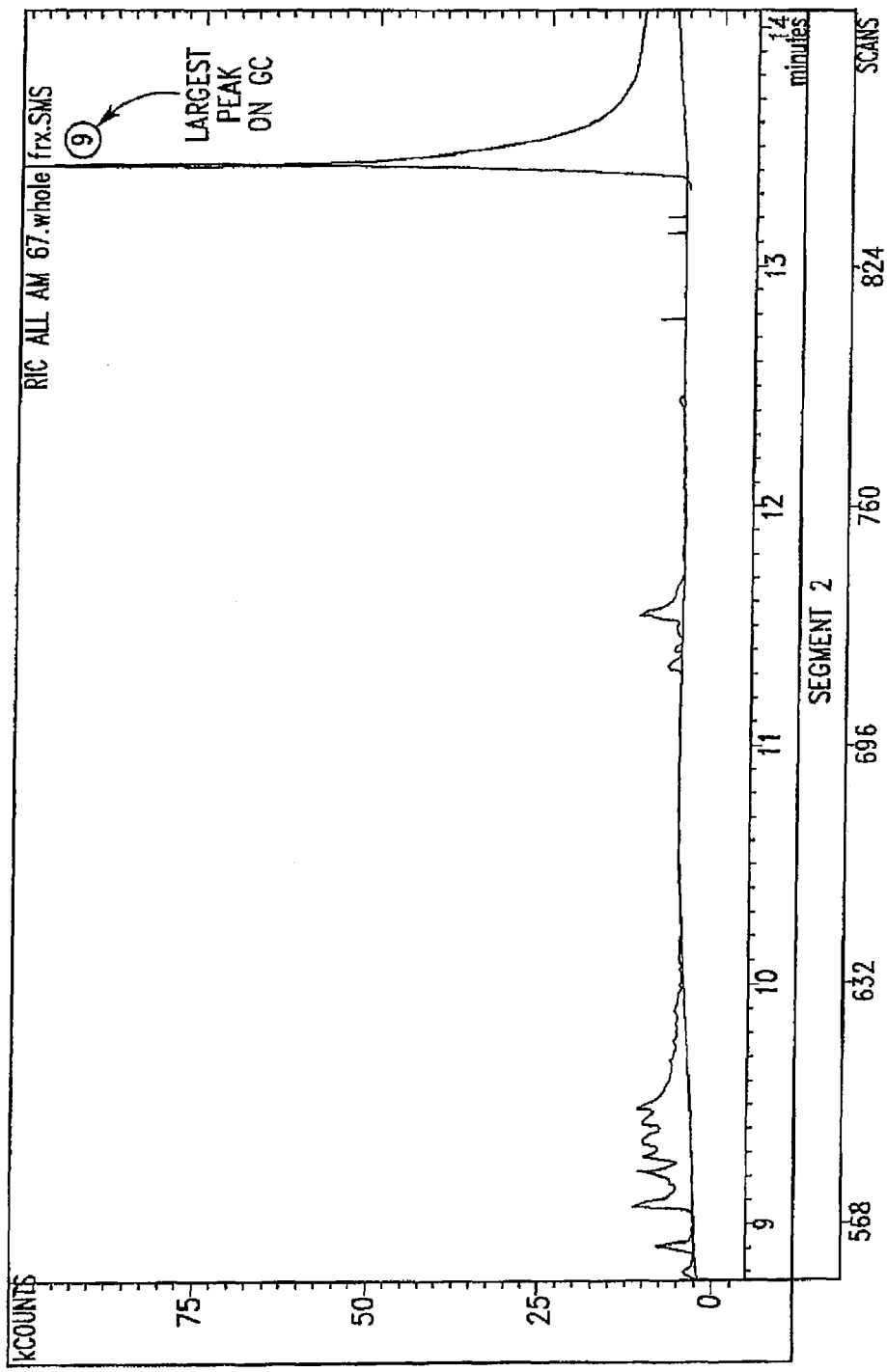
Figure 5:
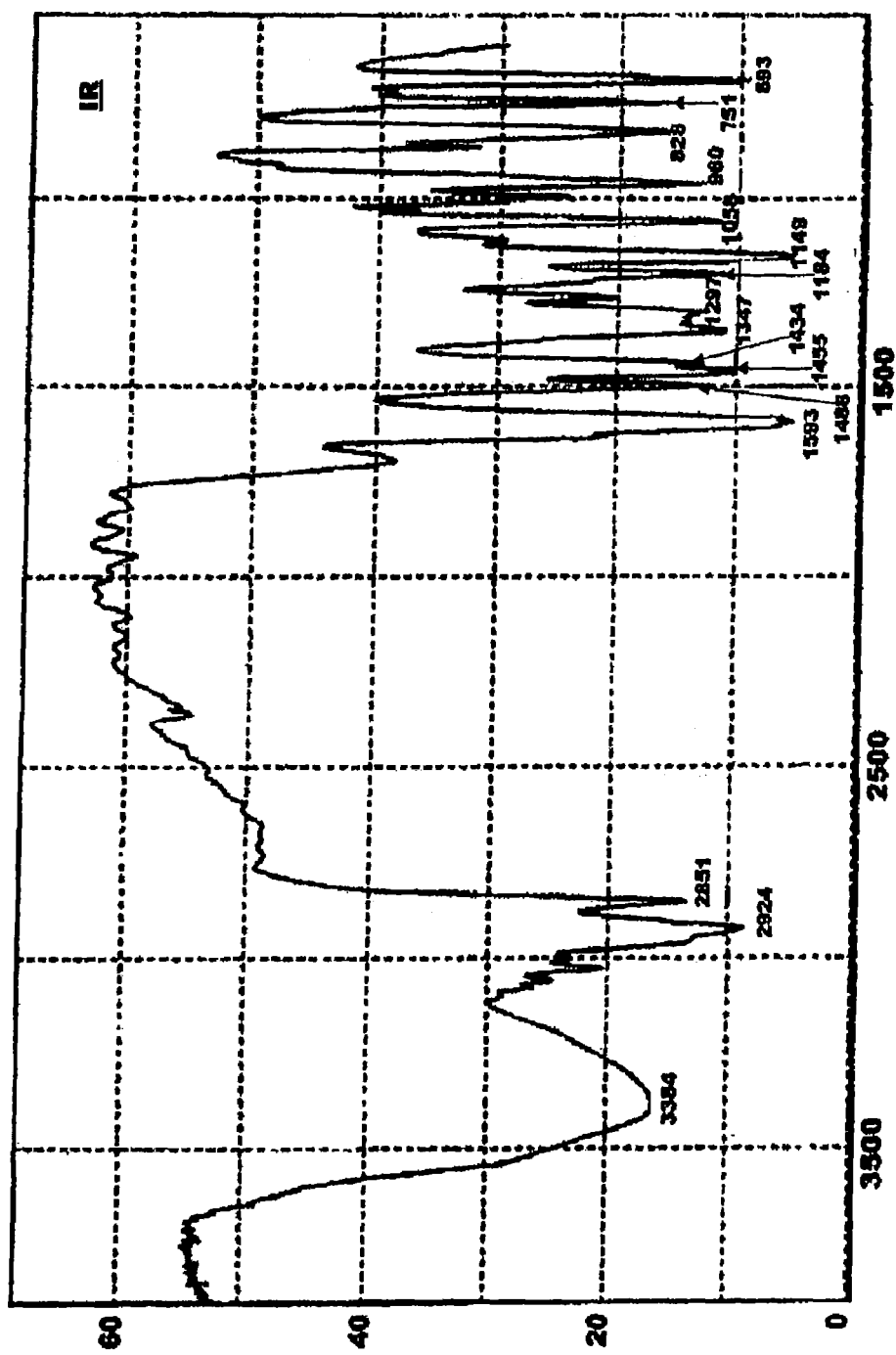
FIG. 5. IR spectrum of the isolated compound of FIG. 2.

FIG. 6 shows the structures of representative compounds of this invention.

FIG. 7 shows the structures of further representative compounds of this invention. Additional analogs, e.g., -Et, —OMe, —F, —Cl, Br, —I (halogen), etc., in place of the methyl groups on the aryl rings are contemplated but are not shown.

FIG. 8. Preliminary efficacy testing of SK-03-92 using a murine thigh abscess model of infection. Swiss Webster mice were infected with *S. aureus* MW2 and treated the next day with DMSO (control, diamonds), a low dose of SK-03-92 (3.2 mg drug per g mouse, squares), or a high dose of SK-03-92 (160 mg drug per g mouse, triangles). Abscesses were collected after another two days and viable bacterial counts assessed. The solid bars represent the median values in each cohort.

FIG. 9. Effects of ivermectin on *C. elegans*. (A) Percentage of worms motile after treatment with various concentrations of ivermectin. The number of motile worms and total number of worms were counted to determine the percentages for each treatment. Most worms were paralyzed after exposure to 0.5 ng/μl of the drug. (B) *C. elegans* in M9 buffer negative control are irregular in shape, illustrating muscle contraction. (C) *C. elegans* after treatment with 0.5 ng/μL ivermectin (right). Most worms in the ivermectin treated well show the characteristic straightening associated with paralysis. Images taken with Leica DFC295 microscope camera (100× magnification). Scale bars=500 μm.

DETAILED DESCRIPTION OF THE INVENTION

Before the present methods are described, it is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a compound" includes a plurality of such compounds and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As defined herein, the term "isomer" includes, but is not limited to stereoisomers and analogs, structural isomers and analogs, conformational isomers and analogs, and the like. In one embodiment, this invention encompasses the use of different stereoisomers of an anti-infective and/or anthelmintic compound of Formulas I, II or III. It will be appreciated by those skilled in the art that the anti-infective compounds useful in the present invention may contain a chiral center. Accordingly, the compounds used in the methods of the present invention may exist in, and be isolated in, optically-active or racemic forms. Some compounds may also exhibit polymorphism. It is to be understood that the present invention encompasses the use of any racemic, optically-active, polymorphic, or stereroisomeric form, or mixtures thereof, which form possesses properties useful in the treatment of microbial infection-related conditions described and claimed herein. In one embodiment, the anti-infective and/or anthelmintic compounds are the pure (Z) or (E)-isomers. In another embodiment, the anti-infective and/or anthelmintic compounds are the pure (R) or (S)-isomers. In another embodiment, the compounds are a mixture of the (R) and the (S) isomers or (E) and (Z) isomers. In another embodiment, the compounds are a racemic mixture comprising an equal amount of the (R) and the (S) isomers. Furthermore, where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention. Preparation of these isomers, compounds and derivatives are well known to one of ordinary skill in the art.
Figure 7A:
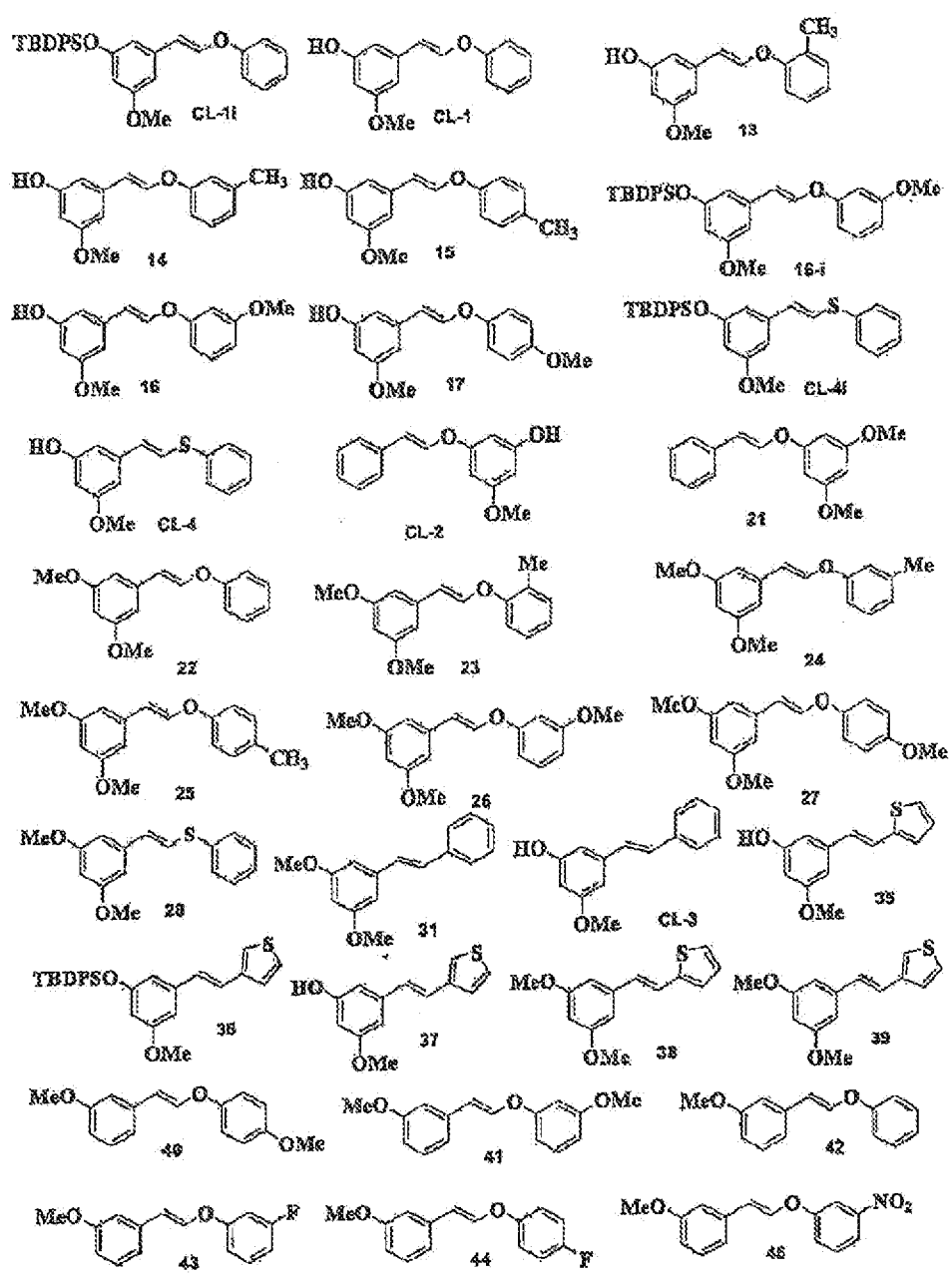
Figure 7B:
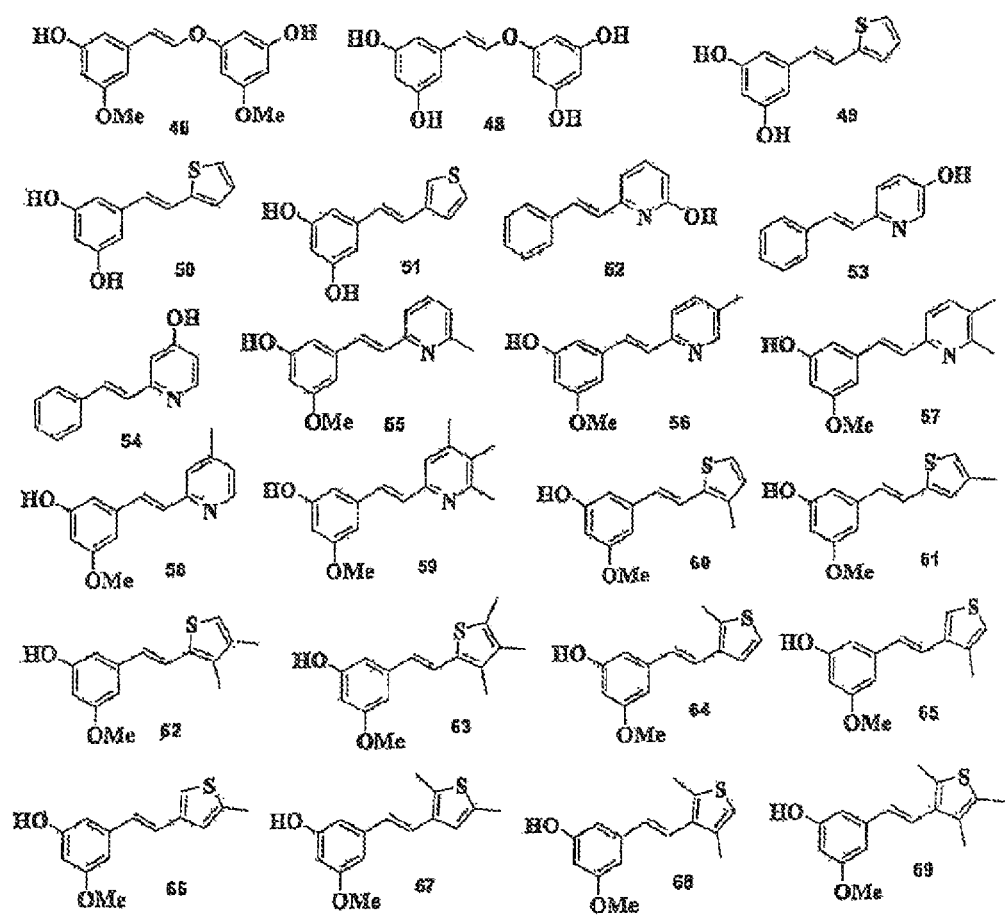
Figure 7C:
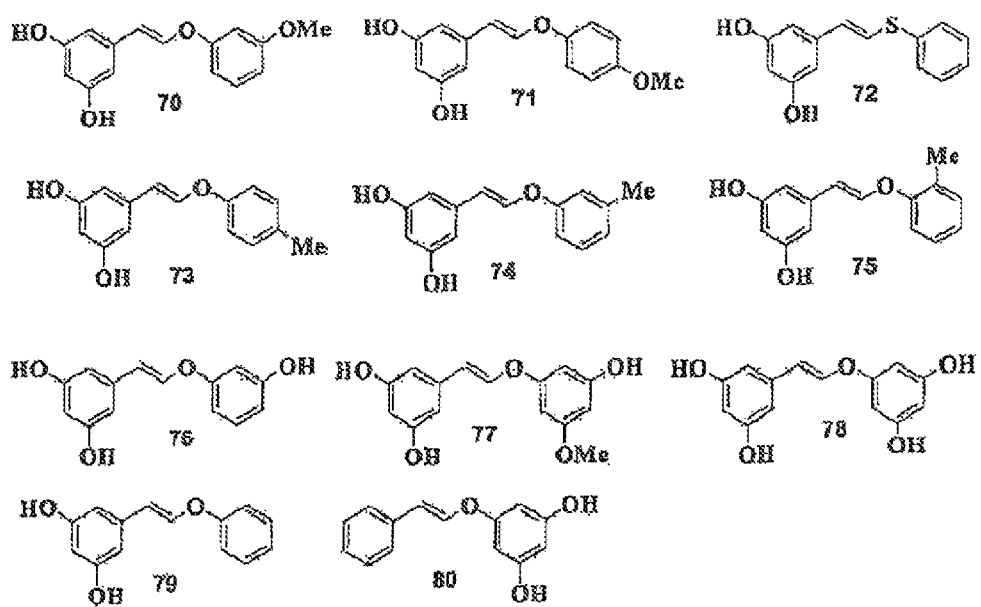
Figure 7D:
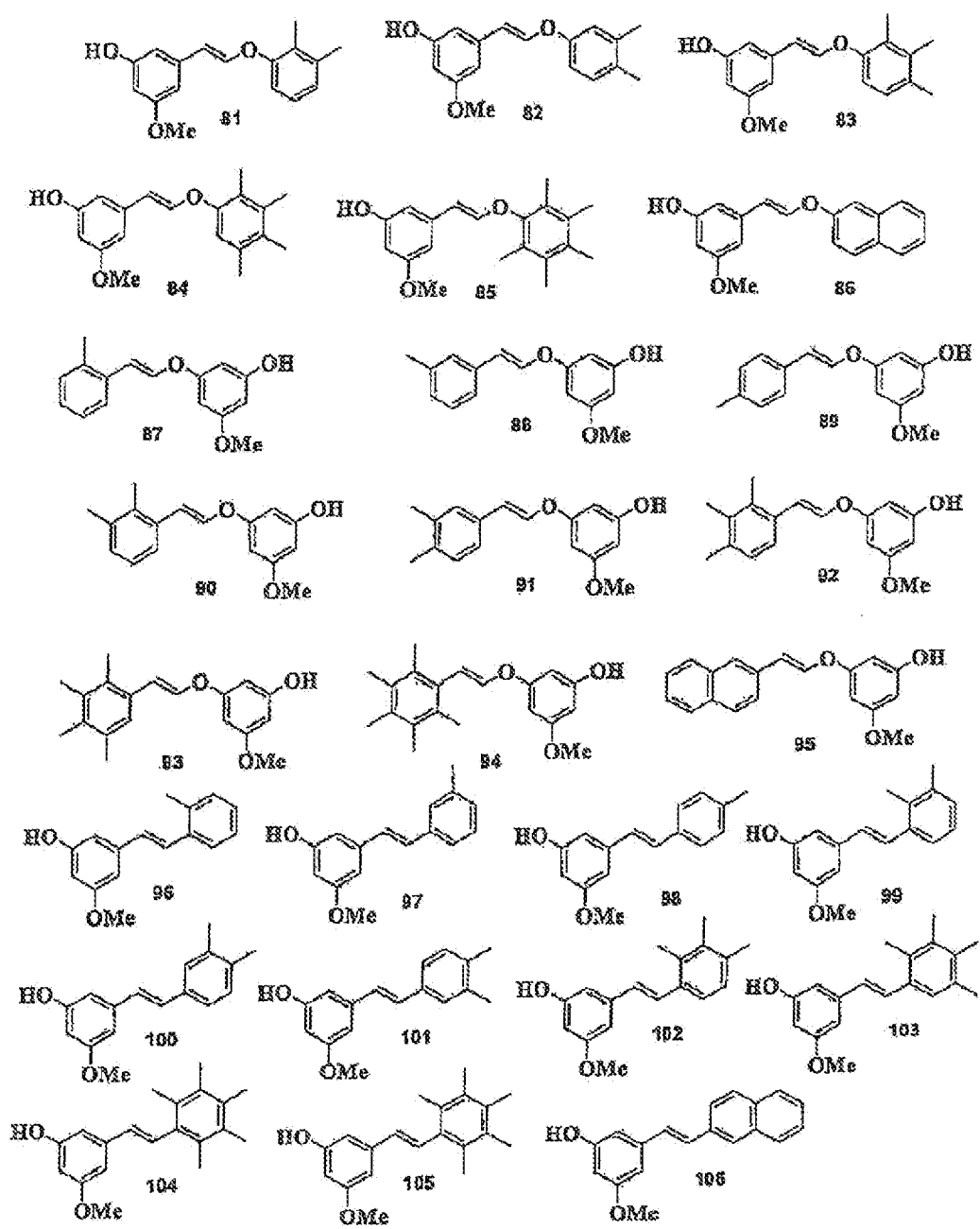
Figure 7E:
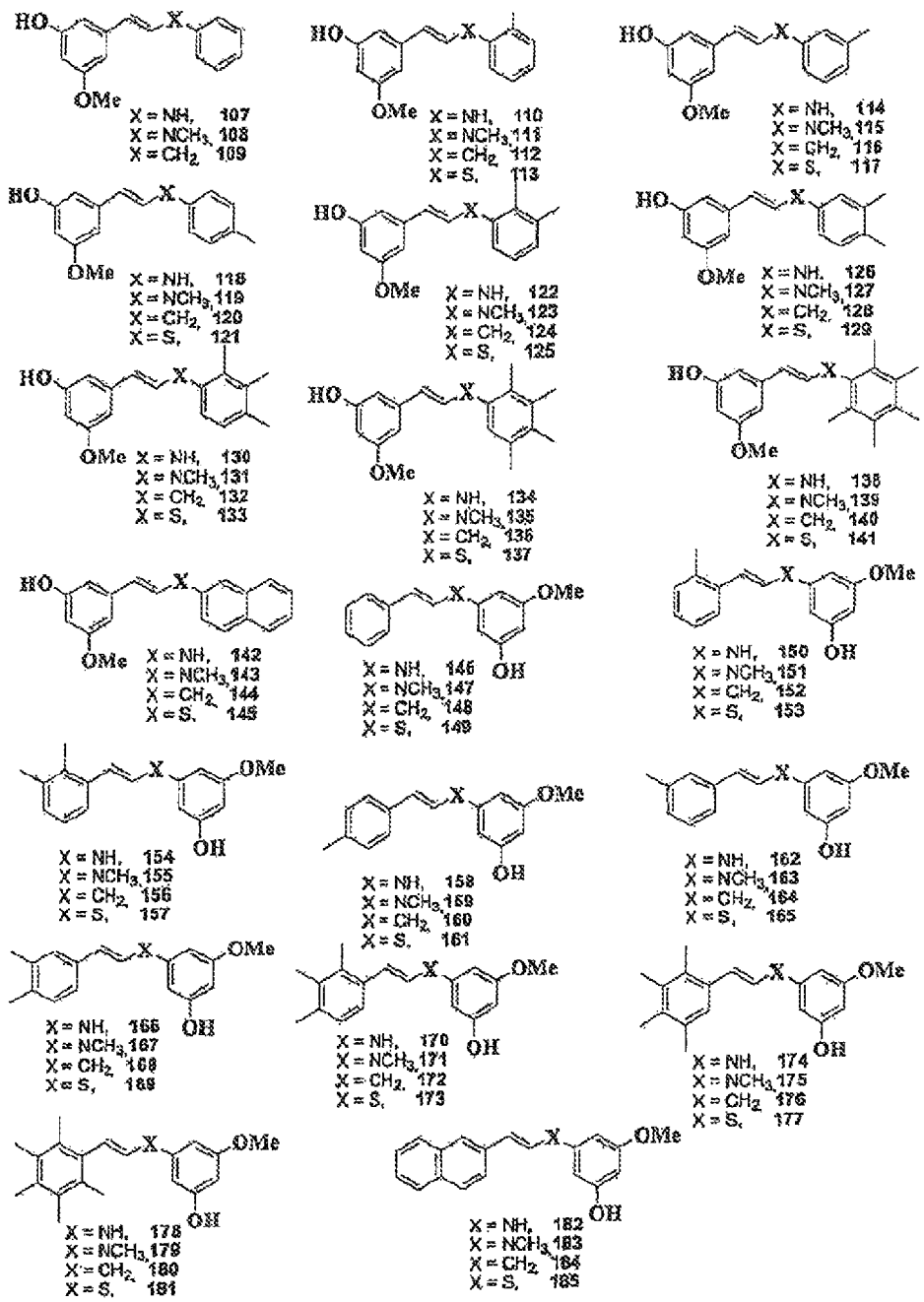

The invention includes the use of pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters. As used herein, the term "pharmaceutically acceptable salt" refers to a compound formulated from a base compound which achieves substantially the same pharmaceutical effect as the base compound.

An active component can be formulated into the composition as neutralized pharmaceutically acceptable salt forms. Pharmaceutically acceptable salts include the acid addition salts, which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Pharmaceutically acceptable salts for topical administration to body surfaces using, for example, creams, gels, drops, and the like, include the anti-infective compounds or their physiologically tolerated derivatives such as salts, esters, N-oxides, and the like are prepared and applied as solutions, suspensions, or emulsions in a physiologically acceptable diluent with or without a pharmaceutical carrier.

This invention further includes methods utilizing derivatives of the anti-infective and/or anthelmintic compounds. The term "derivatives" includes but is not limited to ether derivatives, acid derivatives, amide derivatives, ester derivatives and the like. In addition, this invention further includes methods utilizing hydrates of the anti-infective and/or anthelmintic compounds. The term "hydrate" includes but is not limited to hemihydrate, monohydrate, dihydrate, trihydrate and the like.

This invention further includes methods of utilizing metabolites of the anti-infective and/or anthelmintic compounds. The term "metabolite" means any substance produced from another substance by metabolism or a metabolic process.

The present invention includes within its scope prodrugs of the anti-infective and/or anthelmintic compound. In general, such prodrugs will be functional derivatives of the compound of Formulas (I), (II) or (III) which are readily convertible in vivo into the required compound of Formulas (I), (II) or (III). Conventional procedures for the selection and preparation of suitable prodrug derivatives are described, for example, in Design of Prodrugs, ed. H. Bundgaard, Elsevier, 1985.

As defined herein, "contacting" means that the anti-infective and/or anthelmintic compound used in the present invention is introduced into a sample containing the receptor in a test tube, flask, tissue culture, chip, array, plate, microplate, capillary, or the like, and incubated at a temperature and time sufficient to permit binding of the anti-infective and/or anthelmintic compound to a receptor. Methods for contacting the samples with the anti-infective and/or anthelmintic compound or other specific binding components are known to those skilled in the art and may be selected depending on the type of assay protocol to be run. Incubation methods are also standard and are known to those skilled in the art.

In another embodiment, the term "contacting" means that the anti-infective and/or anthelmintic compound used in the present invention is introduced into a subject receiving treatment, and the compound is allowed to come in contact in vivo. In yet another embodiment, "contacting" includes topical application of the anti-infective and/or anthelmintic agent on a subject.

As used herein, the term "treating" includes preventative as well as disorder remittent treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

In the treatment of infections, minimum inhibitory concentrations (MIC) of a preferred compound of the present invention are shown in Table II. Accordingly, suitable dosage level or an effective amount may be calculated to be about 0.01 to 250 mg/kg per day, preferably about 0.05 to 100 mg/kg per day, and especially about 0.05 to 5 mg/kg per day. The compounds may be administered on a regimen of 1 to 4 times per day, or on a continuous basis via, for example, the use of a transdermal patch.

As used herein, the term "administering" refers to bringing a patient, tissue, organ or cells in contact with an anti-infective and/or anthelmintic compound according to Formulas I, II or III. As used herein, administration can be accomplished in vitro, i.e. in a test tube, or in vivo, i.e. in cells or tissues of living organisms, for example, humans. In certain embodiments, the present invention encompasses administering the compounds useful in the present invention to a patient or subject. A "patient" or "subject", used equivalently herein, refers to a mammal, preferably a human or an animal, that: (1) has a microbial infection remediable or treatable by administration of the anti-infective or anthelmintic according to Formulas I, II or III; (2) is susceptible to a microbial infection that is preventable by administering the anti-infective or anthelmintic compound according to Formulas I, II or III; or (3) has a helminth infestation remediable or treatable by administration of the anti-infective or anhelminitic according to Formulas I, II or III.

In yet another method according to the invention, a pharmaceutical composition can be administered in a controlled release system. For example, the agent may be delivered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In yet another embodiment, polymeric materials can be used. In yet another embodiment, a controlled release system can be placed in proximity to the therapeutic target, i.e., the skin, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including topical, parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially intrathecally, sublingually, rectally, vaginally, nasally, by inhalation, cutaneously, topically and systemically.

The pharmaceutical preparations administrable by the invention can be prepared by known dissolving, mixing, granulating, or tablet-forming processes. For oral administration, the anti-infective compounds or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intra-arterial, or intramuscular injection), the anti-infective compounds or their physiologically tolerated derivatives such as salts, esters, N-oxides, and the like are converted into a solution, suspension, or expulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. It is also envisioned that the compounds of the present invention may be incorporated into transdermal patches designed to deliver the appropriate amount of the drug in a continuous fashion. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50 or 100 mg, of the active ingredient. The tablets or pills of the novel composition can be coated or otherwise compounded to provide a dosage from affording the advantage of prolonged action. For example, the tablet or pill can comprise an inner dosage and an outer dosage component, the latter being in the form of an envelope over the former. The two components can be separated by an enteric layer which, serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, "pharmaceutical composition" means therapeutically effective amounts of the anti-infective and/or anthelmintic compound together with suitable diluents, preservatives, solubilizers, emulsifiers, and adjuvants, collectively "pharmaceutically-acceptable carriers." As used herein, the terms "effective amount" and "therapeutically effective amount" refer to the quantity of active therapeutic agent sufficient to yield a desired therapeutic response without undue adverse side effects such as toxicity, irritation, or allergic response. The specific "effective amount" will, obviously, vary with such factors as the particular condition being treated, the physical condition of the subject, the type of animal being treated, the duration of the treatment, the nature of concurrent therapy (if any), and the specific formulations employed and the structure of the compounds or its derivatives. In this case, an amount would be deemed therapeutically effective if it resulted in one or more of the following: (a) the prevention of microbial infections; (b) the reversal or stabilization of microbial infections; and (c) the reversal or stabilization of helminth infestations. The optimum effective amounts can be readily determined by one of ordinary skill in the art using routine experimentation.

Pharmaceutical compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, milamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

The liquid forms in which the pharmaceutical compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone or gelatin. Thus for example, in a preferred example, liquid form of the novel composition will include oral rinse solutions, anti-caries solutions, disinfectant solutions, and other liquids forms well known to one of ordinary skill in the art.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

Other embodiments of the compositions administered according to the invention incorporate particulate forms, protective coatings, protease inhibitors or permeation enhancers for various routes of administration, including parenteral, pulmonary, nasal and oral.

In another method according to the invention, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, N.Y., pp. 353-365 (1989); Lopez-Berestein ibid., pp. 317-327; see generally ibid).

The pharmaceutical preparation can comprise the anti-infective compound alone, or can further include a pharmaceutically acceptable carrier, and can be in solid or liquid form such as tablets, powders, capsules, pellets, solutions, suspensions elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the anti-infective and/or anthelmintic compound can be administered to a subject by, for example, subcutaneous implantation of a pellet. In a further embodiment, a pellet provides for controlled release of anti-infective and/or anthelmintic compound over a period of time. The preparation can also be administered by intravenous, intraarterial, or intramuscular injection of a liquid preparation oral administration of a liquid or solid preparation, or by topical application. Administration can also be accomplished by use of a rectal suppository or a urethral suppository.

Further, as used herein "pharmaceutically acceptable carriers" are well known to those skilled in the art and include, but are not limited to, 0.01-0.1M and preferably 0.05M phosphate buffer or 0.9% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Pharmaceutically acceptable parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Pharmaceutically acceptable carriers for controlled or sustained release compositions administerable according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Pharmaceutically acceptable carriers include compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

PREFERRED EXEMPLARY EMBODIMENTS

The inventors have found a compound isolated from *Comptonia peregrina* that shows selective anti-infective and anthelmintic activity against several clinically relevant microorganisms. Furthermore, the inventors have found that crude ethanolic extracts of the leaves of *C. peregrina*, and the methanol- and methylene chloride-soluble fractions of the crude extract to generally inhibit the growth of several organisms, as shown in Table I using disc diffusion assay.

TABLE 1

Spectrum of microbial growth inhibition of *C. peregrina* Extracts using disc diffusion assay

| Organism | Gram reaction | Growth inhibition |
| --- | --- | --- |
| Staphylococcus aureus | + | yes |
| Staphylococcus epidermidis | + | yes |
| Streptococcus pneumoniae | + | yes |
| Enterococcus faecalis | + | yes |
| Bacillus cereus | + | yes |
| Helicobacter pylori | − | yes |
| Morganella morganii | − | no |
| Escherichia coli | − | no |
| Pseudomonas aeruginosa | − | no |
| Enterobacter aerogenes | − | no |
| Serratia marcescens | − | no |

Upon chromatographic separation of the crude extracts, this activity was ascribed to two compounds, one present in larger amount with a lower chromatographic $R_f$ value (termed the "major" or "low $R_f$" product), and another present in a lesser amount with a higher chromatographic $R_f$ value (termed the "minor" or "high $R_f$" product). In the following examples, the major or low $R_f$ compound found in *C. peregrina* was studied. Structure elucidation and purification of the major compound resulted in identification of a compound, having an IUPAC nomenclature of E-3-hydroxy-5-methoxy stilbene.

Following extensive chromatographic purification of the major/low compound, the mass and structural data were determined by GC-MS, IR and NMR methods (FIGS. 2-5). Once isolated, the minimum inhibitory concentrations (MIC) of the pure major/low compound were determined against several significant bacteria. The results of these MIC assays are presented in Table 2.

TABLE 2

Minimum inhibitory concentrations (MIC) of the purified major/low compound from *C. peregrina* against several species of bacteria

| Organism | Gram reaction | MIC (µg/mL) |
|---|---|---|
| *Bacillus anthracis* | + | 4 |
| *Bacillus megaterium* | + | 64 |
| *Bacillus cereus* | + | 16 |
| *Bacillus subtilis* | + | 16 |
| *Corynebacterium pseudodiphthericum* | + | 16 |
| *Corynebacterium diphtheriae* Tox⁻ | + | 32 |
| *Corynebacterium xerosis* | + | 16 |
| *Enterococcus faecium* VRE 1 | + | 16 |
| *Enterococcus faecium* VRE 14 | + | 16 |
| *Enterococcus faecalis* ATCC 29212 | + | 16 |
| *Staphylococcus aureus* ATCC 29213 | + | 32 |
| *Staphylococcus aureus* ATCC 25923 | + | 32 |
| *Staphylococcus aureus* MRSA MC-1 | + | 32 |
| *Staphylococcus aureus* MRSA MC-4 | + | 32 |
| *Streptococcus mitis* | + | 64 |
| *Streptococcus agalactiae* | + | 32 |
| *Streptococcus pyogenes* | + | 16 |
| *Streptococcus pneumoniae* ATCC 49619 | + | 8 |
| *Listeria monocytogenes* | + | 32 |
| *Mycobacterium bovis* BCG | N/A | 26 |
| *Escherichia coli* | − | >128 |
| *Pseudomonas aeruginosa* | − | >128 |

ATCC = American Type Culture Collection
MRSA = Methicillin-resistant *Staphylococcus aureus*
VRE = Vancomycin-resistant *enterococci*

Accordingly, the present invention provides anti-infective compound of Formula I, or a salt or prodrug useful for the treatment of disease caused by a microbe. Preferably, the microbe is a bacterium, and more preferably, a gram positive bacterium. Formula I is shown as follows:

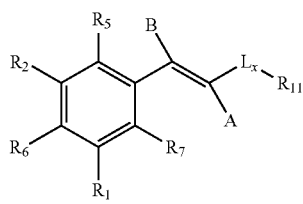

wherein:

$R_1$ is not H when $R_2$ is H and $R_2$ is not H when $R_1$ is H, further wherein $R_1$ is $CH_{(2n+1)}$ O, wherein n is 1-10;

$R_2$ is OH or $CH_{(2n+1)}O$, wherein n is 1-10;

A, B and $R_1$, $R_2$, $R_5$, $R_6$, and $R_7$ are separately and independently selected from a group consisting of H, alkyl and aryl groups;

$R_{11}$ is an alkyl or an aryl group; and

L is an optional linker or linking group;

with x=0 or 1, i.e., if x=0, no linking group is present.

As is noted, "L" is an optional linking group. Various suitable linking groups will be suggested to one skilled in this art in view of this disclosure. "L" is preferably a chalcogen, more preferable O, or S. "L" can also be, essentially, a divalent linking structure known to the art. For example, "L" can be —$CH_2$—, lower alkyl, amino e.g., —NH—, —NR— where R is lower alkyl, and —$CF_2$— among many others.

In a preferred embodiment, the compound, salt or prodrug is according to Formula II:

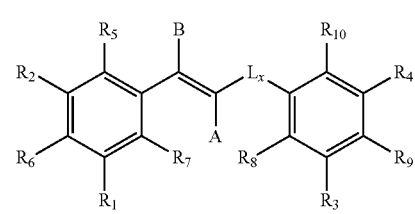

Formula (II)

wherein:

$R_1$ is not H when $R_2$ is H and $R_2$ is not H when $R_1$ is H, further wherein $R_1$ is $CH_{(2n+1)}$ O, wherein n is 1-10;

$R_2$ is OH or $CH_{(2n+1)}O$, where n is 1-10;

A, B and $R_3$ through $R_{10}$ are separately and independently selected from a group consisting of H, alkyl and aryl groups; and L is an optional linker or divalent linking group;

with x=0 or 1, i.e., if x=0, no linking group is present.

In a preferred embodiment, $R_1$ is $CH_3O$, $R_2$ is OH or $CH_{(2n+1)}O$, where n is 1-10; and A, B and $R_3$ through $R_{10}$ are independently selected from a group consisting of H, alkyl and aryl groups.

In another preferred embodiment, $R_1$ is $CH_3O$, $R_2$ is OH and A, B and $R_3$ through R.sub.10 are independently selected from a group consisting of H, alkyl and aryl groups.

Further, said compound, salt or prodrug may have an E or Z orientation. Most preferably, the anti-infective compound is shown as:

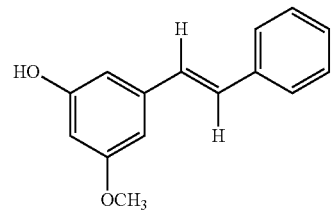 [SMILES: COc1cc(O)cc(/C=C/c2ccccc2)c1]

or a salt or prodrug thereof.

In another embodiment, said anti-infective and/or anthelmintic compound, salt or prodrug is shown in Formula III as follows:

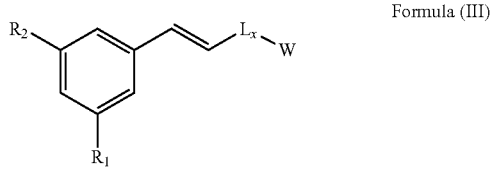

Formula (III)

or salt and prodrug thereof, wherein:

$R_1$ is not H when $R_2$ is H and $R_2$ is not H when $R_1$ is H, further wherein $R_1$ is $CH_{(2n+1)}O$, wherein n is 1-10;

$R_2$ is OH or $CH_{(2n+1)}O$, where n is 1-10;

W is alkyl, phenyl, halophenyl, pyridyl, piperidyl, or a substituted or unsubstituted aryl group, including certain unsubstituted and substituted aromatic heterocycles, such as:

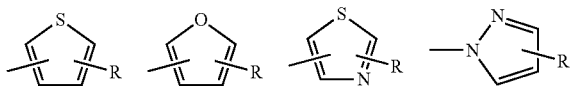

thiophenes · furans · thiazoles · pyrazoles

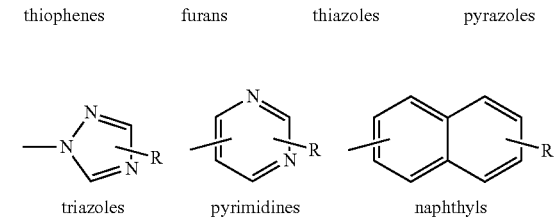

triazoles · pyrimidines · naphthyls

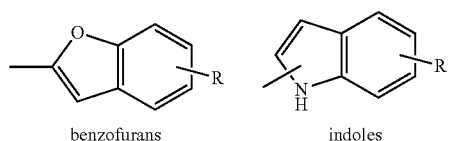

benzofurans · indoles

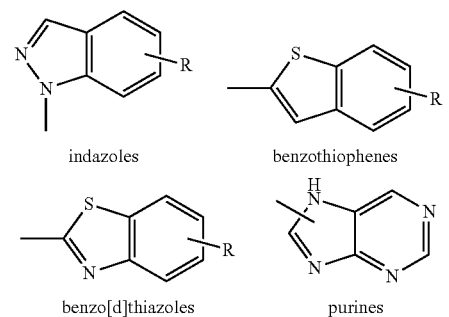

indazoles · benzothiophenes benzo[d]thiazoles · purines where R is selected from: H, or one or more hydroxy, alkyl, alkoxy, amino, nitro, and/or halo substituents; and L is an optional linker or linking group selected from O, S, NH, $CF_2$, or $CH_2$, or from O, S and NH, and x=0 or 1, i.e., if x=0, no linking group is present.

In another embodiment, said anti-infective and/or anthelmintic compound, salt or prodrug is shown in Formula IV as follows:

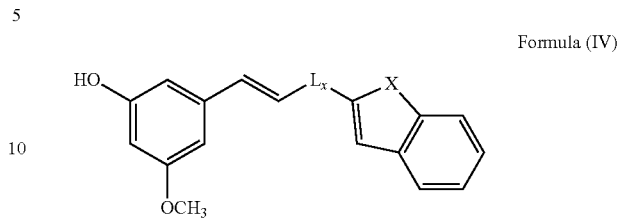

Formula (IV)

or a salt or prodrug thereof, where X is S, NH or O and L is an optional linker or linking group selected from O, S, NH, $CF_2$, or $CH_2$, or from O, S and NH, and x=0 or 1, i.e., if x=0, no linking group is present.

Certain embodiments of the composition of Formula IV having anti-microbial and/or anthelmintic properties are as follows:

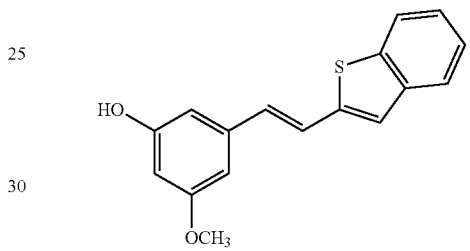

(E)-3-(2-(benzo[b]thiophen-2-yl)vinyl)-5-methoxyphenol, "SK-03-92"

Chemical Formula: $C_{17}H14O_2S$
Exact Mass: 282.07 g/mol
Molecular Weight: 282.36 g/mol
m/z: 282.07 (100.0%), 283.07 (19.2%), 284.07 (4.7%), 284.08 (2.0%)
Elemental Analysis: C, 72.31; H, 5.00; O, 11.33; S, 11.36
Log P: 4.74
CLogP: 5.2962;

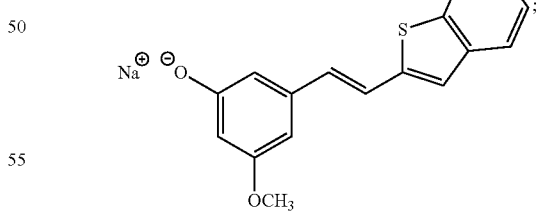

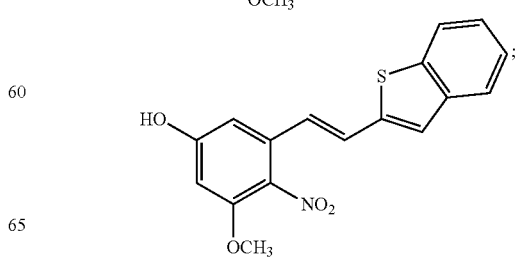

-continued

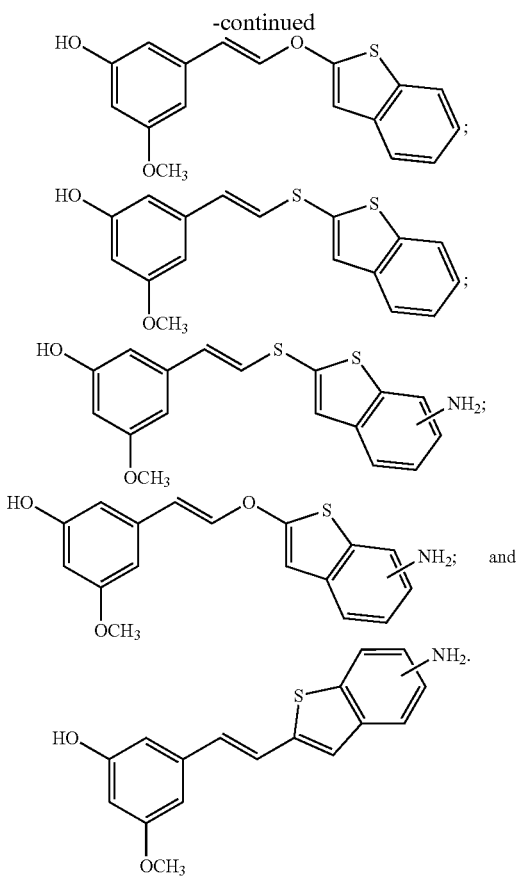

As used herein "alkyl" group refers to a straight chain, branched or cyclic, saturated or unsaturated aliphatic hydrocarbons. The alkyl group has 1-16 carbons, and may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. A "hydroxy" group refers to an OH group. An "alkoxy" group refers to an —O-alkyl group wherein alkyl is as defined above. A "thio" group refers to an —SH group. A "thioalkyl" group refers to an —SR group wherein R is alkyl as defined above. An "amino" group refers to an —NH$_2$ group. An "alkylamino" group refers to an —NHR group wherein R is alkyl is as defined above. A "dialkylamino" group refers to an —NRR' group wherein R and R' are all as defined above. An "amido" group refers to an —CONH$_2$. An "alkylamido" group refers to an —CONHR group wherein R is alkyl is as defined above. A "dialkylamido" group refers to an —CONRR' group wherein R and R' are alkyl as defined above. A "nitro" group refers to an NO$_2$ group. A "carboxyl" group refers to a COOH group.

As used herein, "aryl" includes both carbocyclic and heterocyclic aromatic rings, both monocyclic and fused polycyclic, where the aromatic rings can be 5- or 6-membered rings. Representative monocyclic aryl groups include, but are not limited to, phenyl, furanyl, pyrrolyl, thienyl, pyridinyl, pyrimidinyl, oxazolyl, isoxazolyl, pyrazolyl, imidazolyl, thiazolyl, isothiazolyl and the like. Fused polycyclic aryl groups are those aromatic groups that include a 5- or 6-membered aromatic or heteroaromatic ring as one or more rings in a fused ring system. Representative fused polycyclic aryl groups include naphthalene, anthracene, indolizine, indole, isoindole, benzofuran, benzothiophene, indazole, benzimidazole, benzthiazole, purine, quinoline, isoquinoline, cinnoline, phthalazine, quinazoline, quinoxaline, 1,8-naphthyridine, pteridine, carbazole, acridine, phenazine, phenothiazine, phenoxazine, and azulene.

As used herein, aryl group also includes an arylalkyl group. Further, as used herein "arylalkyl" refers to moieties, such as benzyl, wherein an aromatic is linked to an alkyl group which is linked to the indicated position in the compound of Formula I, II or III.

Another aspect of the invention teaches a method of isolating an anti-infective compound from a Myricaceae family plant. In one embodiment, the plant is *Comptonia peregrina, Comptonia ceterach, Myrica asplenfolia, Liquidamber peregrina, Myrica comptonia, Myrica peregrina, Gale palustris, Myrica gale, Myrica palustris, Myrica cerifera, Myrica pusilla, Cerothammus ceriferus* or *Cerothammus pusilla*. The method comprises the steps of (a) collecting a plant material (b) extracting crude extract from the plant material; and (c) isolating and purifying at least one anti-infective compound from the crude extract. Preferably, the plant material includes leaves of *C. peregrina* plant. Further, in a preferred embodiment, the isolation and purification are carried out by chromatography. In a more preferred embodiment, the isolated anti-infective compound is E-3-hydroxy-5-methoxy stilbene. While the anti-infective agent is preferably extracted from a Myricaceae family plant, other known plants may also provide the anti-infective compound.

Yet another aspect of the present invention describes a method of treating infections or inhibiting microbial growth in a patient in need thereof, said method comprising the step of administering an effective amount of a compound having a structure represented by Formula I, II, III or IV or a salt or prodrug thereof. Such infections may be caused by a bacterium.

Another aspect of the invention provides a pharmaceutical composition, comprising: (a) an effective amount of a compound having a chemical structure represented by Formula I, II, III or IV, or a salt or a prodrug thereof, and (b) a pharmaceutically-acceptable carrier. The compound salt or prodrug is an anti-infective agent useful for the treatment of disease caused by a bacterium. Most preferably, the bacterium is a gram positive bacterium.

Yet another aspect of the invention provides a method of inhibiting microbial growth. The method comprising contacting microbe to be inhibited with a microbial inhibiting amount of a compound according to Formula I, II, III or IV or salt or prodrug thereof.

Preferably the microbe to be inhibited is a bacterium. Further, the bacterium to be inhibited is selected from the group consisting of *Staphylococcus aureus, Staphylococcus epidermidis, Streptococcus pneumoniae, Enterococcus faecalis, Bacillus cereus, Helicobacter pylori, Bacillus megaterium, Bacillus subtilis, Corynebacterium pseudodiphthericum, Corynebacterium diphtherias tox, Corynebacterium xerosis, Enterococcus faecium* VRE 1, *Enterococcus faecium* VRE 14, *Enterococcus faecalis* ATCC 29212, *Staphylococcus aureus* ATCC 29213, *Staphylococcus aureus* ATCC 25923, *Staphylococcus aureus* MRSA MC-1, *Staphylococcus aureus* MRSA MC-4, *Streptococcus mitis, Streptococcus agalactiae, Streptococcus pyogenes, Streptococcus pneumoniae* ATCC 49619, *Listeria monocytogenes, Mycobacterium bovis* BCG, *Mycobacterium tuberculosis, Brevibacillus* sp., *Clostridium perfringens, Corynebacterium xerosisurealyticum* and *Bacillus anthracis*. In certain embodiments, the bacterium is a gram Gram-positive bacterium, *Mycobacterium* species, or *H. pylori*.

The invention also provides a composition suitable for inhibiting growth of microbes. The composition comprises: a first ingredient which inhibits microbial growth comprising the compound, prodrug or salt of Formula I, II, III or IV; and a second ingredient which comprises an acceptable carrier or an article of manufacture. Preferably, in the composition, the first ingredient is E-3-hydroxy-5-methoxy stilbene.

In one embodiment, the acceptable carrier is an antibacterial agent, a skin conditioning agent, a lubricating agent, a coloring agent, a moisturizing agent, binding and anti-cracking agent, a perfuming agent, a brightening agent, a UV absorbing agent, a whitening agent, a transparency imparting agent, a thixotropic agent, a solubilizing agent, an abrasive agent, an antioxidant, a skin healing agent, a cream, a lotion, an ointment, a shampoo, an emollient, a patch a gel, a sol or other pharmaceutically acceptable carriers as described above. In another embodiment, the article of manufacture is a textile, a fiber, a glove or a mask. Therefore the composition in combination with the article of manufacture will provide anti-infective textiles and fibers, or anti-infective gloves and masks, useable in medical facilities, and other locations where anti-infective properties are desirable. Furthermore, the microbe inhibiting composition will include anti-caries solution, oral rinse solutions, anti-microbial cosmetic applications, anti-microbial soaps, sprays, cleaning solutions, detergents, and other applications where the anti-infective properties are desirable. Compositions, methods and techniques for using the acceptable carriers and articles of manufacture are well known to one of ordinary skill in the art.

The following examples are related to the compounds and methods of the present invention and are put forth for illustrative purposes only. These examples are not intended to limit the scope of the invention.

EXAMPLE 1

Isolation and Identification of the Major Anti-Infective Compound from *C. peregrina*

The stems and leaves of *C. peregrina* were collected from various northern Wisconsin locales during the summer months of June-September and air dried in closed paper bags to protect the plant material from exposure to light. In an exemplary preparation, the leaves of *C. peregrina* were separated from the woody stems, and 163.69 g of this dried leaf material was placed in a cellulose extraction thimble. The plant material was subjected to continuous extraction for 24 hours using a Soxhlet extractor and methylene chloride ($CH_2Cl_2$) as the solvent. After removal of the solvent under reduced pressure and thorough drying the crude leaf extract was obtained as a sticky brown gum that weighed 8.87 g (5.4%).

The crude extract was then fractionated by flash column chromatography, using a 42 mm ID column, silica gel 60 as the stationary phase, and $CH_2Cl_2$ as the eluting solvent. Typically, 100-150, 10 mL fractions were collected and assayed for microbial growth inhibition. This bioassay-directed fractionation allowed for the identification of a major component, "CL-low," that inhibited the growth of several strains of bacteria in the Kirby-Bauer disc diffusion assay. The column fractions, including the active component, were also analyzed by thin-layer chromatography (TLC) using Baker-flex® silica gel IB2-F plates (with fluorescent indicator) and $CH_2Cl_2$ as the eluting solvent (see FIG. 1). In this TLC system, the active CL-low component was found to produce an intense, violet-colored spot when viewed under short-wave UV light (254 nm) and to have a relatively low $R_f$ value of 0.19 (enclosed in box in FIG. 1).

All column fractions containing the active CL-low component were pooled, and this component was purified and isolated by successive, preparative TLC, using $CH_2Cl_2$ as the solvent.

In another preferred embodiment, HPLC Assay for CL Low was performed as shown below:

EXAMPLE 2

HPLC Assay for CL Low

Sample Preparation: Dried samples extracted from TLC plates are dissolved in a minimal volume of methylene chloride and diluted to approximately 20 $A_{290}$/ml with isopropanol. Absorbance at 290 nm is close to the UV maximum for CL Low.

Column and Conditions: The assay is run on a 4.6 mm.times.300 mm Aligent C-8 HPLC column. The elution buffer is Methanol: 1% acetic acid in water (65%/35%) run isocratically. Flow rate is 1.25 ml/min.

Assay Analysis: The Waters HPLC system has a diode array detector that allows analysis at several wavelengths during the run. A 15 μl sample is injected and the column is monitored at 254 nm and 290 nm.

Additional information: Spectra may be analyzed across a given peak to insure that the peak is pure (i.e., the spectra at the leading edge of the peak looks the same as at the end of the peak). The amount of material injected may also be adjusted to so that peak heights are about 1 Absorbance unit in height. Once the HPLC assay is run, the controls and standards may be run. Preferably, the controls and standards are run both before and the HPLC runs.

In the chromatograph as shown in FIG. 12, the method described above was used to assess the purity of the CL low compound that the inventors used to deduce structure and characterize activity.

EXAMPLE 3

Characterization of 3-hydroxy-5-methoxy Stilbene Against Methicillin-Resistant *Staphylococcus aureus*, Vancomycin-Resistant Enterococci and *Mycobacterium bovis*

Methods: Methylene chloride extracts of the dried leaves of *C. peregrina* were initially screened for anti-microbial activity with disk diffusion assays (DDAs) against four indicator bacterial species. Successive flash column and thin layer chromatography were used to partition the crude extract into fractions that were tested for activity using DDAs against *Staphylococcus epidermidis*. An active compound was purified, and its structure was obtained using IR, GC-MS, and NMR analyses. Using NCCLS guidelines, DDAs and minimum inhibitory concentration (MIC) assays were performed against clinically significant Gram-positive bacterium. Isoniazid was used as a control for MIC assays performed with *Mycobacterium bovis* strain BCG. Tetracycline and rifampin were used as controls against all other bacterial species tested to ensure validity of the MIC assays.

Results: Structural analysis indicates the active compound is E-3-hydroxy-5-methoxy stilbene. This compound was found to inhibit the growth of all Gram-positive bacteria tested, including vancomycin-resistant enterococci (MIC 32 μg/mL), methicillin-resistant *Staphylococcus aureus* (MIC 32 μg/mL) and M bovis (MIC 25.6 μg/mL). The compound did not show significant activity against the Gram-negative bacteria tested (MICs>128 μg/mL).

Conclusion: A novel anti-bacterial compound isolated from *C. peregrina* possesses broad-spectrum activity against clinically important Gram-positive bacterial species.

*Bacillus anthracis*

Furthermore, the species *Bacillus cereus* and *Bacillus anthracis* have been shown to have extensive homologies at the DNA (Read et al., 2003) and protein (Gohar et al., 2005) levels. Most of the differences that are attributed to these species can be explained by the presence of separate virulence plasmids in each species. In terms of screening with known antibiotics, both species do have some common susceptibility patterns against ciprofloxacin and gentamicin (Turnbull et al., 2004). Differences in susceptibility patterns were noted for penicillin and erythromycin (*B. anthracis* typically susceptible and *B. cereus* typically resistant). The penicillin susceptibility results in *B. anthracis* are due to a truncation of a positive regulatory gene, not because of a lack of β-lactamase genes (Read et al., 2003). For screening against new classes of antibiotics, both species are likely to show the same susceptibility patterns as a result of their structural similarities. (These similarities and differences have been discussed in the literature, as shown in Gohar et al. 2005. A Comparative Study of *Bacillus cereus, Bacillus thuringiensis*, and *Bacillus anthracis* Extracellular Proteomes. Proteomics 5:3696-3711; Read et al. 2003. The genome sequence of *Bacillus anthracis* Ames strain and comparisons to closely related bacterium. Nature 423:81-86; and Turnbull et al. 2004. MICs of selected antibiotics for *Bacillus anthracis, Bacillus cereus, Bacillus thuringiensis*, and *Bacillus mycoides* from a range of clinical and environmental sources as determined by the Etest. J. Clin. Microbiol. 42:3626-3634, which are incorporated herein by reference for all purposes.)

*Mycobacterium bovis* BCG

The active compound is E-3-hydroxy-5-methoxy stilbene and may also be highly effective in treating tuberculosis. The purified extract was screened against *Mycobacterium bovis* BCG, a virulent, slow growing, BSL level 2/3 pathogen, closely analogous to *M. tuberculosis*. The minimum inhibitory concentration (MIC) in this assay was found to be 25.6 μg/mL.

EXAMPLE 4

Spectral Interpretation and Structural Assignments

A sample of CL-low was obtained as a yellow, waxy solid, and this was analyzed spectroscopically (GC-MS, IR, and NMR) and found to have a molecular mass of 226 g/mol and molecular formula, $C_{15}H_{14}O_2$. On the basis of the available spectral information, the chemical structure of CL-low is:

IUPAC nomenclature of the CL-low compound was determined to be E-3-hydroxy-5-methoxy stilbene.

The material from Example I was characterized by using numerous analytical chemistry tools such as MS, IR, $^1$H-NMR and $^{13}$C-NMR. In MS, following observations were made: MS (m/z): Molecular ion, $M^{30}$=226 and $C_{15}H_{14}O_2$.

IR observations were made to further characterize and elucidate the structure of the active ingredient, for example a strong, broad absorption at 3384 $cm^{-1}$ indicated presence of —OH group (phenol).

Further, .sup.1H-NMR (.delta.ppm) produced the following observations: 3.85, s, 3H; —$OCH_3$; 5.05, bs; 1H, —OH 6.35; 1H, t, (J=1.5 Hz) Hc 6.61, 1H, t, (J=1.5 Hz), Ha 6.66, 1H, t, (J=1.5 Hz), Hb 7.03, 2H, q, (J=16 Hz, trans), 2 vinyl protons of trans-/E-alkene 7.27, 1H, t, (J=7.5 Hz), Hp 7.36, 2H, t, (J=1.5 Hz), Hm 7.50, 2H, d, (J=7.5 Hz), Ho.

Finally $^{13}$C-NMR (.delta.ppm) produced the following observations: 55, —$OCH_3$ 101, CH, (vinyl carbon near the substituted arene) 105, CH 107, CH 126.5, CH×2 (identical, 2 carbons at Ho) 127.8, CH 128.3, CH 128.7, CH×2 (identical, 2 carbons at Hm) 129.4, CH 137, 140, 156, 162, C×4 (4 unsubstituted aromatic carbons).

In the most preferred embodiment, the present compound was determined to be E-3-hydroxy-5-methoxy stilbene.

EXAMPLE 5

Chemical Synthesis Procedures and Spectral Data

General Experimental Details

All chemicals were purchased from Sigma-Aldrich Chemical Co., Inc., Milwaukee, Wis., or Alfa Aesar, A Johnson Matthey Co., Ward Hill, Mass. All solvents (THF, DCM, toluene, DMF) were distilled prior to use except for chloroform, hexane, ethyl acetate, methanol, ethanol, acetone and diethyl ether. Solvents used in syntheses were distilled and dried under an argon atmosphere as follows: tetrahydrofuran (THF) from Na/benzophenone; dichloromethane (DCM), toluene, and benzene from $CaH_2$; methanol from $Mg(OMe)_2$; DMSO from $P_2O_5$ at reduced pressure; and acetone over $CaSO_4$. All experiments involving air and/or moister-sensitive compounds were conducted in oven dried round-bottom flasks capped with rubber septa, and attached via a needle and connecting tubing to an argon manifold equipped with a mercury bubbler (ca. 5 mm positive pressure of argon, and after the addition of solvents and regents, the reaction vessel was sealed with a cap. All the reactions were carried out under argon unless stated otherwise. All Cu-coupling reactions were executed under degassing conditions. Low temperature reactions were carried out in ice/water (0° C.), ice/NaCl (−22° C.) and in dry ice/EtOAc (−78° C.).

Analytical thin layer chromatography (TLC) was carried out on glass plates precoated (0.25 mm) with silica gel 60 $F_{254}$. Compounds were detected by visualization under an ultraviolet lamp (254 nm) and by dipping the plates inside an $I_2$ tank. Preparative thin layer chromatography (PTLC) was performed on silica gel glass plates (EM science, 60 $F_{254}$, 20×20 cm, 0.25 mm thickness). Compounds were visualized under UV light. All solvent mixtures used were volume/volume (v/v) mixtures. Flash column chromatography (FCC) was performed on silica gel, Merck Grade 60 (40-63 μm), mesh size 230-400, 60 A$^0$ according to Still, W. C. et al. 1978. Dry column flash chromatography was carried out according to Harwood, L. M, 1985. All mixed solvent eluents are reported as v/v solutions.

Concentration refers to removal of volatiles at water aspirator pressure on a rotary evaporator, followed by evacuation at 0.5-10 torr using a high vacuum pump. Unless otherwise noted, all reported compounds were homogeneous by thin layer chromatography (TLC) and by $^1$H NMR.

The $^1$H, $^{13}$C, $^{13}$CDEPT-135, $^{13}$CDEPT-90, $^1$H—$^{13}$C HSQC, $^1$H—$^{13}$C HMBC experiments were recorded on a Bruker 300/75 MHz spectrometer. Chemical shifts are given in ppm (.delta.) relative to tetramethylsilane as an internal standard. Coupling constants (J) are given in Hz where indicated. NMR peak assignments were made using HSQC, and HMBC experiments. Low resolution mass spectra (EI/CI) were recorded on a Hewlett-Packard 5985B gas chromatography mass spectrometer, and infrared spectra were recorded on a Thermo Nicolet Nexus 870 FT-IR E. S. P. spectrometer.

General Procedure A. $CrCl_2$ Mediated Preparation of 2-aryl vinyl iodide.

Aldehyde (1.0 eq) and iodoform (2.0 eq) in THF (0.5 M) were added to a suspension of anhydrous $CrCl_2$ (6.0 eq) in dry THF (0.6 M) under argon at 0° C. The reaction mixture was stirred at 0° C. for a specific time depending on the substrate. The reaction mixture was then poured into water and extracted with ether (3×mL). The combined organic extracts were dried ($Na_2SO_4$) and concentrated in vacuo. The crude oil was purified by flash column chromatography (FCC) on silica gel to afford the pure vinyl iodide.[3]

General Procedure B. O-vinylation of Phenol or Substituted Phenols and S-vinylation of Thiophenols by 2-aryl vinyl iodides.

NMO (3.0 eq) was added to a suspension of the vinyl iodide (1.0 eq), phenol or substituted phenol or thiophenol (1.5 eq) and $Cs_2CO_3$ (2.1 eq) in dry toluene under argon at rt, and this was stirred for 5 min, followed by degassing of the solvent and subsequent addition of CuCl (3.0 eq) to the reaction mixture. The reaction flask was sealed with a condenser and degassing was repeated three times. Under positive pressure of argon the reaction mixture was heated to 115° C. and stirred for 12 h. This mixture was cooled to rt, diluted with diethyl ether (3×mL), and filtered through a plug of celite. The filtrate was washed with 14% aq. ammonium hydroxide and dried ($Na_2SO_4$). It was then concentrated in vacuo and subjected to FCC on silica gel to afford the pure vinyl ether.[4]

General Procedure C. Deprotection of the TBDPS (tert-butyldiphenylsilyl) Group of the Coupled Product.

TBAF.THF (1.0 M, 1.1 eq) was added to a stirred solution of the TBDPS protected coupled product (1.0 equiv) in THF (0.5 M) under argon at rt, and the solution was allowed to stir for 2 h. The reaction mixture was diluted with $H_2O$, extracted with EtOAc (3×mL) and washed with brine. The organic extracts were dried ($Na_2SO_4$), and concentrated in vacuo. The crude ether was purified by FCC on silica gel to afford pure ether.

General Procedure D. Wittig-Horner Reaction of aryl aldehyde with Wittig-Horner Reagents for the Preparation of Stilbene Analogues.

Benzylbromide or a substituted benzylbromide (1.0 equiv.) was heated with excess triethylphosphite (1.5 equiv.) to 130° C. under argon until the evolution of ethyl bromide had ceased. Excess triethylphosphite was removed by distillation in vacuo and the residual diethylbenzylphosphonate or the ring substituted diethylbenzylphosphonate, Wittig-Horner reagent, respectively, was used directly for the later step.[5]

Benzaldehyde or a substituted-benzaldehyde (1.0 eq) was added to the dry solution of diethylbenzylphosphonate analogues (1.1 equiv) and NaH (60% wt dispersed in mineral oil, 3.5 eq) in dry DMF under argon and at 0° C. The reaction mixture was allowed to stir at rt for 1 h and was then heated to 80-90° C. for an additional 1 h. The reaction mixture was cooled to rt and allowed to stand overnight. A mixture of water-methanol (2:1) was then added slowly until the stilbene analogues precipitated.[5] The solid stilbene analogue was collected by filtration, and was purified either by crystallization or by flash column chromatography (FCC).

General Procedure E. Negeshi Coupling of aryl bromides with vinyl iodides for the Preparation of Stilbene Analogues.

n-Butyllithium (1.5 eq, 2.87 M in hexane) was added to the arylbromide (1.1 eq) solution in THF at −78° C. under argon and the mixture was stirred for 30 min. The temperature of the reaction mixture was brought to 0° C. and allowed to stir for 10 min at rt. Anhydrous $ZnCl_2$ (1.2 eq) was added to the reaction mixture at 0° C. and this slurry was stirred for 1 h. The vinyliodide in THF (0.5 M) was added to the reaction mixture followed by the rapid addition of Pd $(PPh_3)_4$ (7 mol %) and this slurry was allowed to stir at rt for a specific period of time depending on the substrate. The solvent from the reaction mixture was then evaporated in vacuo. The crude oil was then suspended in $H_2O$ and extracted with EtOAc (3×mL). The combined organic extracts were washed with 5% aq $NaHCO_3$ (2×mL) and dried ($Na_2SO_4$). This organic extracts were concentrated in vacuo and subjected to FCC on silica gel to afford the stilbene analogues.[6]

TABLE 3

Minimum Inhibitory Concentration (MIC) Values For Selected Synthetic Analogs of the Natural Product Stilbene*, CL-3/CL-Low (Chemical Structures of These Coded Samples Shown In FIG. 6)

| Sample | S. aureus 29213, G+ | S. aureus MC-1, G+ | E. faecium VRE 1, G+ | S. pyogenes, G+ | B. cereus, G+ (anthrax surrogate) | M. smegmatis (TB surrogate) |
|---|---|---|---|---|---|---|
| CL-1 | 32 | 64 | 64 | 32 | 16 | 128 |
| CL-2 | 32 | 32 | 32 | 16 | 64 | 128 |
| CL-3* | 8 | 16 | 32 | 16 | 16 | 64 |
| CL-3D (31) | >512 | — | — | — | — | — |
| CL-4 | 16 | 32 | 32 | 8 | 16 | 128 |
| CL-5 (37) | 16 | 32 | 32 | 4 | 32 | 128 |
| CL-6 (35) | 32 | 32 | 64 | 32 | 32 | 64 |
| 13 (A11) | 16 | 32 | 32 | 32 | 64 | >128 |
| 14 (A9) | 8 | 32 | 32 | 32 | 16 | 64 |
| 15 (A10) | 16 | 32 | 32 | 32 | 64 | >128 |
| 16 (A8) | 16 | 64 | 64 | 16 | 64 | 128 |
| 17 (A6) | 16 | 64 | 64 | 32 | 64 | 128 |

EXAMPLE 6

Experimental Results For Efficacy of SK-03-92

In light of the results obtained on the bioactivity of substituted stilbenes such as reservatrol, as well as the promising antimicrobial MIC studies on E-3-hydroxy-5-methoxy stilbene and certain analogs thereof shown in Tables 2 and 3, various analogs of E-3-hydroxy-5-methoxy stilbene, including E-phenoxystyrenes, E-phenolthiolstyrenes and other substituted E-stilbenoid analogs. Some of these analogs, and their MIC values for various bacteria are as follows:

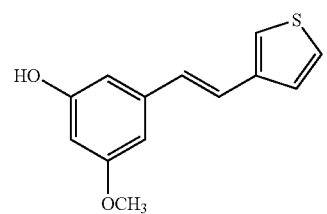

CL-5

Minimum Inhibitory Concentration (MIC) Values
(CL-5)

| | |
|---|---|
| S. aureus | 16 µg/mL |
| MRSA | 32 µg/mL |
| VRE | 32 µg/mL |
| S. pyogenes | 4 µg/mL |
| B. cereus | 32 µg/mL |
| M. smegmatis | 128 µg/mL |

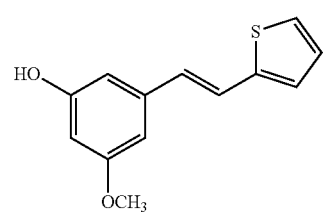

CL-6

Minimum Inhibitory Concentration (MIC) Values
(CL-6)

| | |
|---|---|
| S. aureus | 32 µg/mL |
| MRSA | 32 µg/mL |
| VRE | 64 µg/mL |
| S. pyogenes | 32 µg/mL |
| B. cereus | 32 µg/mL |
| M. smegmatis | 64 µg/mL |

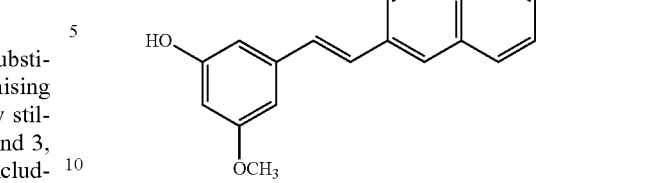

SK-03-28F$_2$

Minimum Inhibitory Concentration (MIC) Values
(Cpd. #106 (FIGS. 6-7), SK-03-28F$_2$)

| | |
|---|---|
| S. aureus | 8 µg/mL |
| MRSA | N/A |
| VRE | N/A |
| S. pyogenes | N/A |
| B. cereus | 16 µg/mL |
| M. smegmatis | 256 µg/mL |

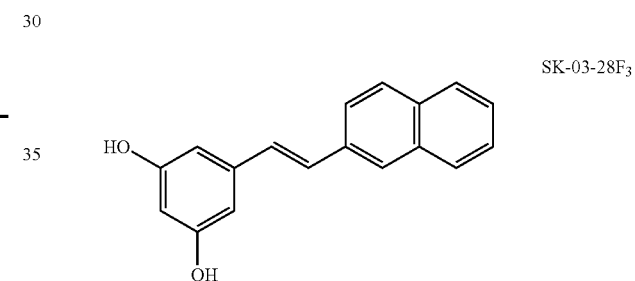

SK-03-28F$_3$

Minimum Inhibitory Concentration (MIC) Values
(SK-03-28F$_3$)

| | |
|---|---|
| S. aureus | 8 µg/mL |
| MRSA | 256 µg/mL |
| VRE | N/A |
| S. pyogenes | N/A |
| B. cereus | 8 µg/mL |
| M. smegmatis | >512 µg/mL |

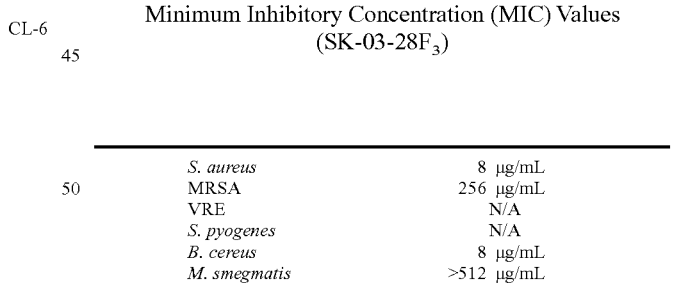

SK-03-44F$_2$

Minimum Inhibitory Concentration (MIC) Values
(SK-03-44F$_2$)

| | |
|---|---|
| S. aureus | 32 μg/mL |
| MRSA | >512 μg/mL |
| VRE | N/A |
| S. pyogenes | N/A |
| B. cereus | 256 μg/mL |
| M. smegmatis | >512 μg/mL |

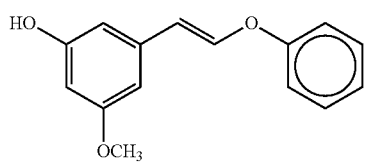

CL-1

Minimum Inhibitory Concentration (MIC) Values
(CL-1)

| | |
|---|---|
| S. aureus | 32 μg/mL |
| MRSA | 64 μg/mL |
| VRE | 64 μg/mL |
| S. pyogenes | 32 μg/mL |
| B. cereus | 32 μg/mL |
| M. smegmatis | 128 μg/mL |

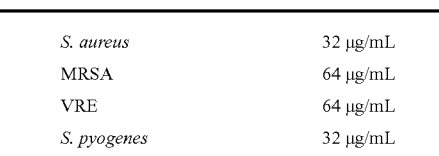

A8

Minimum Inhibitory Concentration (MIC) Values
(Cpd. #16, A8)

| | |
|---|---|
| S. aureus | 32 μg/mL |
| MRSA | 64 μg/mL |
| VRE | 64 μg/mL |
| S. pyogenes | 16 μg/mL |
| B. cereus | 64 μg/mL |
| M. smegmatis | 128 μg/mL |

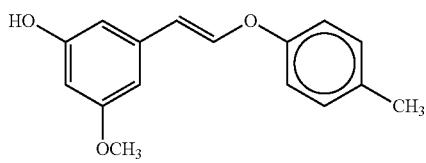

A10

Minimum Inhibitory Concentration (MIC) Values
(Cpd. #15, A10)

| | |
|---|---|
| S. aureus | 16 μg/mL |
| MRSA | 32 μg/mL |
| VRE | 32 μg/mL |
| S. pyogenes | 32 μg/mL |
| B. cereus | 64 μg/mL |
| M. smegmatis | >128 μg/mL |

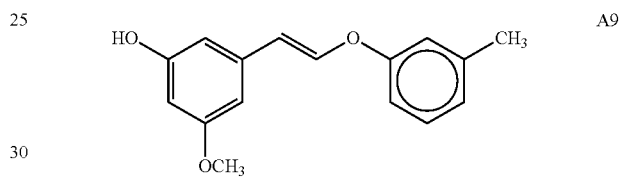

A9

Minimum Inhibitory Concentration (MIC) Values
(Cpd. #14, A9)

| | |
|---|---|
| S. aureus | 16 μg/mL |
| MRSA | 32 μg/mL |
| VRE | 32 μg/mL |
| S. pyogenes | 32 μg/mL |
| B. cereus | 32 μg/mL |
| M. smegmatis | 64 μg/mL |

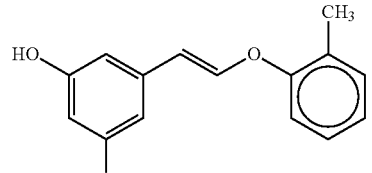

A11

Minimum Inhibitory Concentration (MIC) Values
(Cpd. #13, A11)

| | |
|---|---|
| S. aureus | 16 μg/mL |
| MRSA | 32 μg/mL |
| VRE | 32 μg/mL |

-continued

| | |
|---|---|
| S. pyogenes | 32 μg/mL |
| B. cereus | 32 μg/mL |
| M. smegmatis | >128 μg/mL |

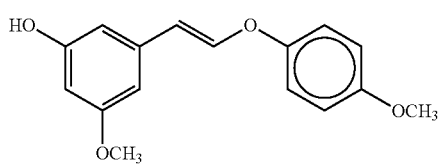

A6

Minimum Inhibitory Concentration (MIC) Values
(Cpd. #17, A6)

| | |
|---|---|
| S. aureus | 32 μg/mL |
| MRSA | 64 μg/mL |
| VRE | 64 μg/mL |
| S. pyogenes | 32 μg/mL |
| B. cereus | 64 μg/mL |
| M. smegmatis | 128 μg/mL |

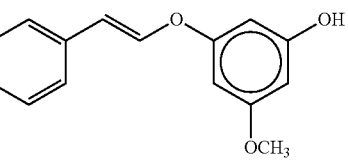

CL-2

Minimum Inhibitory Concentration (MIC) Values
(CL-2)

| | |
|---|---|
| S. aureus | 32 μg/mL |
| MRSA | 32 μg/mL |
| VRE | 32 μg/mL |
| S. pyogenes | 16 μg/mL |
| B. cereus | 64 μg/mL |
| M. smegmatis | 128 μg/mL |

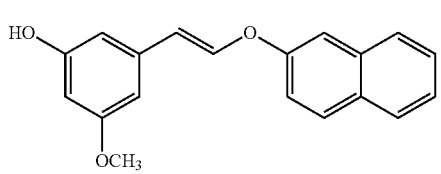

SK-04-23

Minimum Inhibitory Concentration (MIC) Values
(Cpd. #86, SK-04-23)

| | |
|---|---|
| S. aureus | 16 μg/mL |
| MRSA | 8 μg/mL |
| VRE | N/A |
| S. pyogenes | N/A |
| B. cereus | 8 μg/mL |
| M. smegmatis | 128 μg/mL |

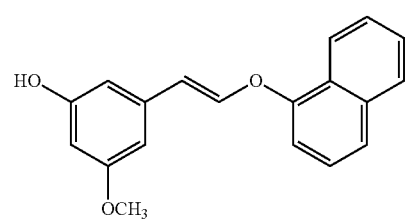

SK-04-22

Minimum Inhibitory Concentration (MIC) Values
(SK-04-22)

| | |
|---|---|
| S. aureus | 32 μg/mL |
| MRSA | 16 μg/mL |
| VRE | N/A |
| S. pyogenes | N/A |
| B. cereus | 8 μg/mL |
| M. smegmatis | 128 μg/mL |

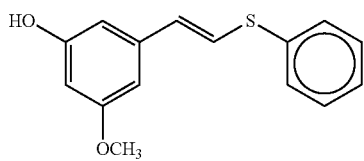

CL-4

Minimum Inhibitory Concentration (MIC) Values
(CL-4)

| | |
|---|---|
| S. aureus | 16 μg/mL |
| MRSA | 32 μg/mL |
| VRE | 32 μg/mL |
| S. pyogenes | 8 μg/mL |
| B. cereus | 16 μg/mL |
| M. smegmatis | 128 μg/mL |

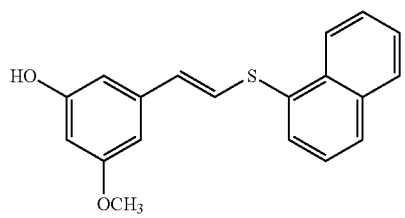

SK-05-16

Minimum Inhibitory Concentration (MIC) Values
(SK-05-16)

| | |
|---|---|
| S. aureus | 4 µg/mL |
| MRSA | N/A |
| VRE | N/A |
| S. pyogenes | N/A |
| B. cereus | 4 µg/mL |
| M. smegmatis | 128 µg/mL |

SK-05-17

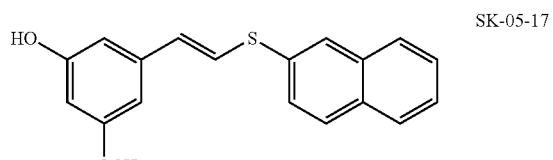

Minimum Inhibitory Concentration (MIC) Values
(Cpd. #145, SK-05-17)

| | |
|---|---|
| S. aureus | 4 µg/mL |
| MRSA | N/A |
| VRE | N/A |
| S. pyogenes | N/A |
| B. cereus | 4 µg/mL |
| M. smegmatis | 128 µg/mL |

SK-05-04

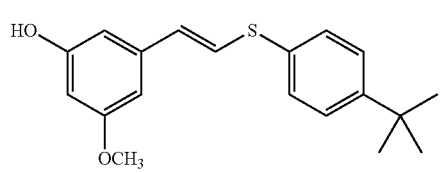

Minimum Inhibitory Concentration (MIC) Values
(SK-05-04)

| | |
|---|---|
| S. aureus | 16 µg/mL |
| MRSA | N/A |

-continued

| | |
|---|---|
| VRE | N/A |
| S. pyogenes | N/A |
| B. cereus | 8 µg/mL |
| M. smegmatis | 128 µg/mL |

SK-05-01

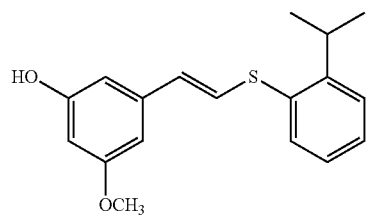

Minimum Inhibitory Concentration (MIC) Values
(SK-05-01)

| | |
|---|---|
| S. aureus | 16 µg/mL |
| MRSA | N/A |
| VRE | N/A |
| S. pyogenes | N/A |
| B. cereus | 16 µg/mL |
| M. smegmatis | 256 µg/mL |

SK-05-22

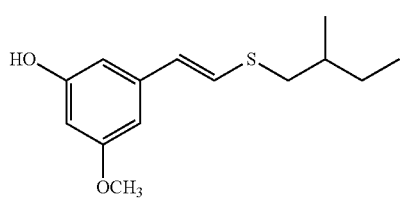

Minimum Inhibitory Concentration (MIC) Values
(SK-05-22)

| | |
|---|---|
| S. aureus | 16 µg/mL |
| MRSA | N/A |
| VRE | N/A |
| S. pyogenes | N/A |
| B. cereus | 16 µg/mL |
| M. smegmatis | 128 µg/mL |

With particular regard to SK-03-92, once isolated, the minimum inhibitory concentrations (MIC) of SK-03-92 were determined against several clinically significant bacteria. The results of these MIC assays are presented in Tables 4 and 5.

TABLE 4

MICs of SK-03-92 Against Gram positive Bacteria

| Species | Source | MIC (µg/ml) |
|---|---|---|
| Staphylococcus aureus ATCC 29213 | American Type Culture Collection (ATCC) | 2.0 |
| Staphylococcus aureus MW 2 | Jean Lee | 2.0 |
| Enterococcus faecalis ATCC 29212 | ATCC | 4.0 |
| Enterococcus faecium VRE 1 | Marshfield Clinic (MC) | 2.0 |
| Enterococcus faecium VRE 14 | MC | 2.0 |
| Clostridium tertium | University of Wisconsin-Lacrosse (UWL) | 1.0 |
| Clostridium novyi A | UWL | 2.0 |
| Clostridium difficile | UWL | 2.0 |
| Propionibacterium acnes | UWL | 2.0 |
| Peptostreptococcus anaerobius | UWL | 1.0 |
| Erysipelothrix rhusiopathiae | UWL | 8.0 |
| Streptococcus pneumoniae | UWL | 16.0 |
| Streptococcus agalactiae | UWL | 2.0 |
| Streptococcus bovis | UWL | 2.0 |
| Streptococcus mitis | UWL | 2.0 |
| Listeria monocytogenes | UWL | 2.0 |
| Bacillus cereus | UWL | 1.0 |
| Mycobacterium avium | UWL | 16.0 |
| Mycobacterium bovis BCG | David Sherman | 25.0 |
| Mycobacterium chelonae | UWL | 32.0 |
| Mycobacterium fortuitum | UWL | 16.0 |
| Mycobacterium intracellulare | UWL | 32.0 |
| Mycobacterium kamasii | UWL | 16.0 |
| Corynebacterium pseudodiphthericum | UWL | 2.0 |
| Corynebacterium xerosis | UWL | 2.0 |

TABLE 5

Screening SK-03-92 against a number of methicillin-sensitive S. aureus (MSSA) and community-associated methicillin-resistant S. aureus (CA-MRSA) strains

| Methicillin sensitivity | Source | # Tested | MIC range (µg/ml) |
|---|---|---|---|
| MSSA | MC | 39 | 1-2 |
| CA-MRSA | Wisconsin State Laboratory of Hygiene | 43 | 2-4 |

Bacteria

All of the species used in this study are listed in Table 4.

Safety Testing with Swiss Webster Mice

The safety testing was done with 6-8 week old female Swiss Webster mice. The mice were tested for SK-03-92 safety according to OECD 425 regulations using doses of 300 mg/kg and ~3 g/kg injected intraperitoneally.

Minimum Inhibitory Concentration (MICs)

The MICs were performed according to CLSI regulations using S. aureus ATCC 29213 and E. faecalis ATCC 29212 tested against tetracycline as controls.

Minimal Bacterial Concentration Testing (MBC)

Following the MIC, the last three wells showing no bacterial growth were diluted and plated onto BHI agar to do MBC testing.

Efficacy Testing with Swiss Webster Mice

Efficacy testing was done using 6-8 week old female Swiss Webster mice. A murine thigh was injected with 50 ul (1×106 CFU/ml) of S. aureus MW2 mixed with Cytodex beads (Sigma). One day after the bacterial were injected the mice were intraperitoneally injected with 50 ul of DMSO, a low dose (2.56 mg/ml) of SK-03-92 in DMSO, or a high dose (128 mg/ml) of SK-03-92 in DMSO. After 2 days following the injection of SK-03-92, the mice were euthanized by IACUC regulations and the soft tissues were collected homogenized and cultured on BHI agar plates.

Many analogs of the stilbene, phenoxystyrene and phenothiostyrene were synthesized, including the compound SK-03-92. The new analog was tested against a variety of Gram-positive bacteria, including VRE and MRSA. In this study, it is shown that the SK-03-92 has MICs of 2-4 µg/ml against many MRSA strains and MICs of 2 µg/ml against VRE strains. Furthermore, the compound has MICs from 1-8 µg/ml against a variety of other Gram-positive species. In addition, preliminary safety testing has demonstrated that intraperitoneal injections of SK-03-92 up to 3 g/kg did not appear to harm the mice and a thigh abscess model showed in vivo efficacy. Our results suggest that SK-03-92 may be safe in animals and covers a wide range of Gram-positive bacteria. All other analogues of phenoxystyrene and phenothiostyrene were also shown the potential activity against a wide range of Gram-positive bacteria.

Figure 8:
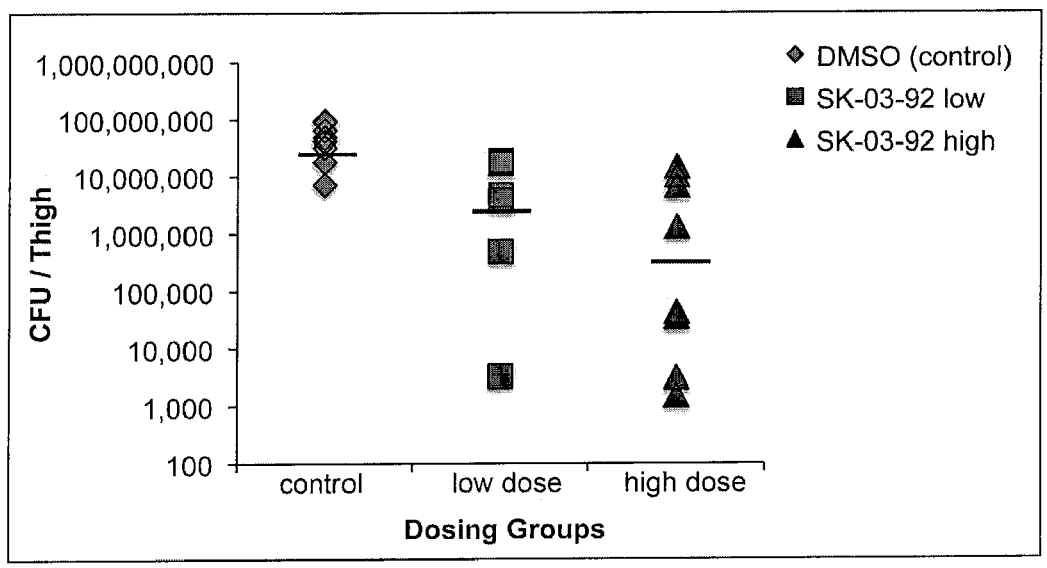

The preliminary efficacy testing demonstrated, as shown in FIG. 8, that thigh abscess infections treated with SK-03-92 have their CFU/thigh reduced 2.5 (low dose) to 3 logs (high dose) using a single intraperitoneal injection of the drug.

The MICs were 2-4 µg/ml for all of the S. aureus strains tested, including MRSA. In addition, the MICs were 2-4 µg/ml against Enterococcus sp., including VRE strains. Moreover, all of the Gram-positive bacterial species tested were killed by SK-03-92.

An MBC analysis showed the drug was bactericidal.

Safety testing demonstrated that the drug did not harm mice even at a ~2 g/kg dose administered intraperitoneally and after a repeated dose.

Preliminary efficacy testing in a murine thigh abscess model showed a 2-3 log drop in the bacterial counts two days after drug injection.

These results suggest that SK-03-92 maybe safe and effective for treatment against many Gram-positive bacterial infections.

In addition, other stilbene analogs have been developed and evaluated for their antimicrobial activity. More particularly, the following Bacteria and Growth Conditions Mycobacterium species were initially grown on tryptic soy agar (TSA) for three to four days. The culture was then inoculated into Middlebrook 7H9 broth medium supplemented with OADC and allowed to grow at 37° C. for five days. Staphylococcus aureus strain ATCC 29123 was grown on TSA for 24 hours at 37° C.

Chemicals Tested

The original compound isolated from C. peregrina was identified as a stilbene. A series of 80 structural analogs of the drug were synthesized and suspended in dimethylsulfoxide. The following compound structures are for those compounds identified in Table 5.

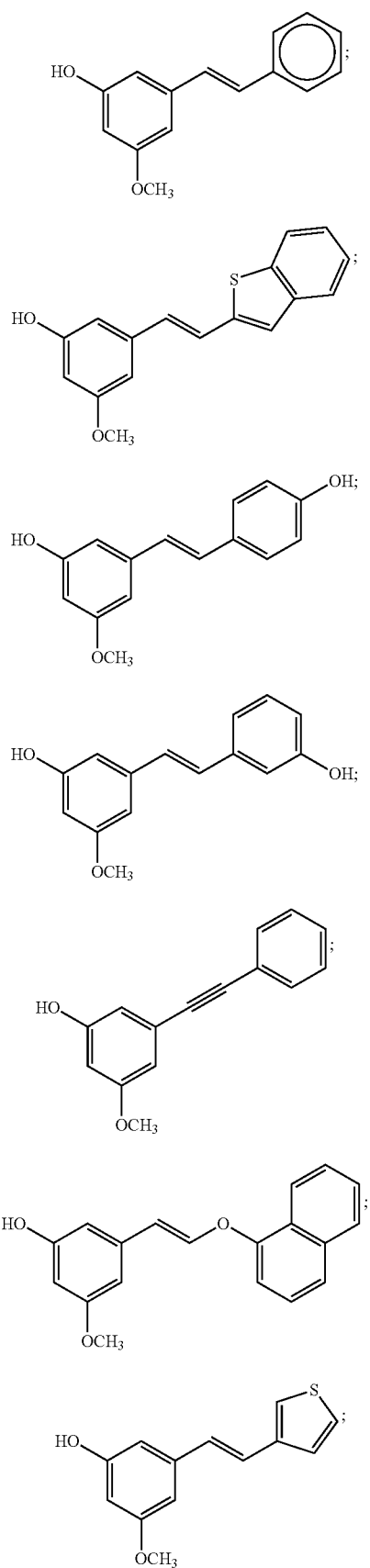
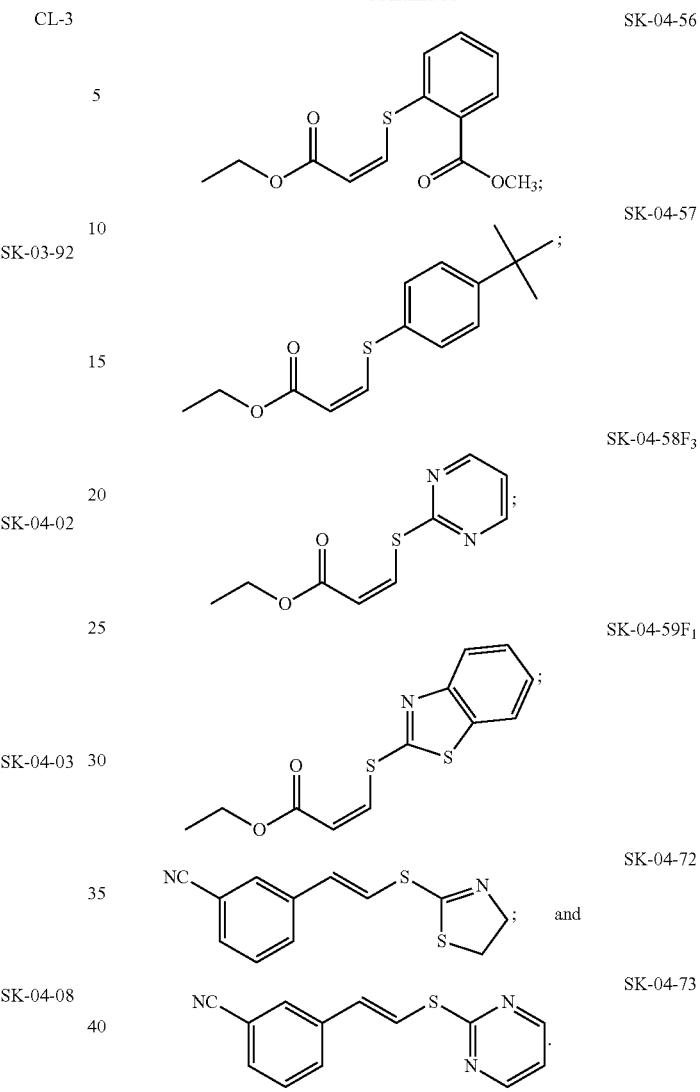

Minimum Inhibitory Concentration Assay

All MICs, the results of which are shown in Table 6, were performed under CLSI regulations. Briefly, each drug was diluted two-fold in cation-adjusted Mueller-Hinton broth, starting at a concentration of 512 mg/ml in a microtiter plate. Next, the *S. aureus* culture was suspended in cation-adjusted Mueller-Hinton broth to a 0.5 McFarland turbidity standard. The culture was diluted to 1×106 CFU/ml in the same medium and added to each well of the microtiter plate. Plates were read after 24 h. For the *Mycobacterium* species, some modifications of this procedure were done. Bacterial cells were dispersed by adding sterile glass beads to a test tube and mixing them vigorously on a vortex mixer for three minutes. After the bacteria were suspended, they were diluted to a 0.5 McFarland turbidity standard in Middlebrook 7H9 broth medium supplemented with OADC. The bacterial suspensions were diluted 100-fold in the broth medium appropriate for the organism to a bacterial concentration of 1.0×106 cells/ml and processed as described above. Plates were read at 24, 48, and 72 h.

TABLE 6

Minimum Inhibitory Concentration (MIC - µg/ml) of Various Synthetic Stilbene Analogs

| | S. aureus ATCC 29213 | S. aureus MC-1 | M. smegmatis | M. chelonae | M. fortuitum | M. avium | M. intracellulare | M. kansasii |
|---|---|---|---|---|---|---|---|---|
| CL-3 | 16 | 16 | 64 | 16 | 16 | N/A | N/A | N/A |
| SK-03-92 | 4 | 2 | 32 | 32 | 16 | 16 | 32 | 16 |
| SK-04-02 | 32 | 32 | 64 | 32 | 64 | 16 | 16 | 32 |
| SK-04-03 | 32 | 16 | 64 | 64 | 64 | 8 | 16 | 64 |
| SK-04-08 | 32 | 1 | 64 | N/A | 32 | 16 | 16 | 32 |
| SK-04-22 | 16 | 16 | 128 | 256 | 128 | 64 | 128 | 64 |
| SK-04-23 | 8 | 8 | 128 | 128 | 128 | 64 | 64 | 64 |
| SK-04-56 | >512 | >512 | 64 | 64 | 64 | 64 | 256 | 64 |
| SK-04-57 | >512 | >512 | 16 | 8 | 4 | 64 | 128 | 16 |
| SK-04-58F | >512 | >512 | 64 | 32 | 64 | 64 | 128 | 64 |
| SK-04-59F | >512 | >512 | 16-32 | 8 | 16 | 64 | 16 | 8 |
| SK-04-72 | >512 | >512 | 64 | 64 | 64 | 64 | 64 | N/A |
| SK-04-73 | 512 | >512 | 64 | 256 | 256 | 512 | 512 | 128 |

With regard to these compounds and the above results, it can be seen that:

the SK-03-92 analog had the best activity against *S. aureus;*

27/47 analogs had activity against *S. aureus* and *Mycobacterium* species;

7/47 analogs only had activity against *S. aureus;* optimal activity was achieved in the presence of benzothiophene and phenolicgroups; and derivitization of the native compound increased the antimicrobial activity.

Anthelmintic Activity Experimental

In addition to the antibacterial efficacy of the compounds discussed previously, a number of the compounds evaluated also show efficacy as anthelmintic agents. Specific examples of these compounds include:

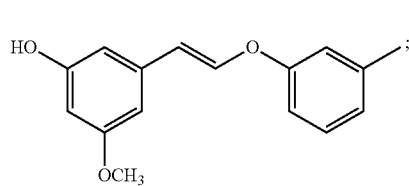
A-9

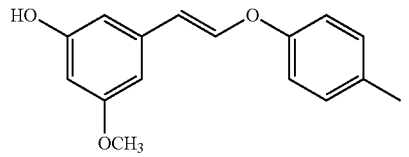
A-10

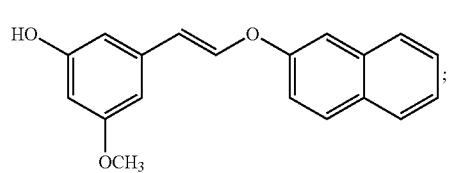
SK-04-23

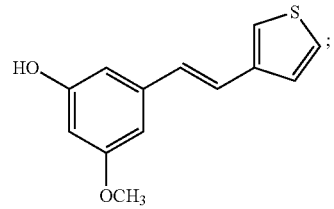
CL-5

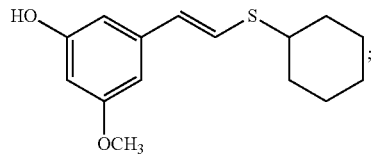
SK-04-50

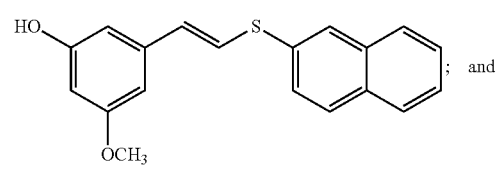
SK-05-17; and

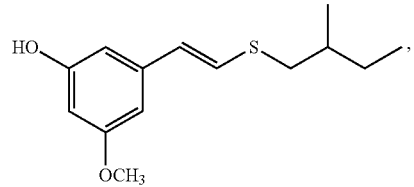
SK-05-22 as well as compounds represented by Formula V:

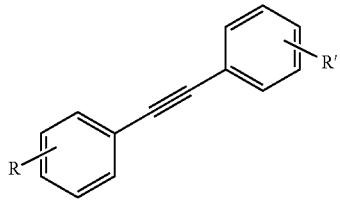
Formula (V)

wherein:
R is selected from —OH and —OCH₃ and combinations thereof, and in one embodiment is

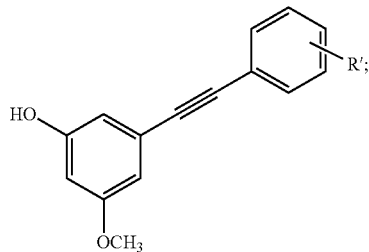

and
R' is selected from H, hydroxy, alkyl, alkoxy, amino, nitro, halo, or a substituted or unsubstituted aryl group, including certain unsubstituted and substituted aromatic heterocycles and combinations thereof.

In one embodiment, the compound of Formula V is:

SK-04-08

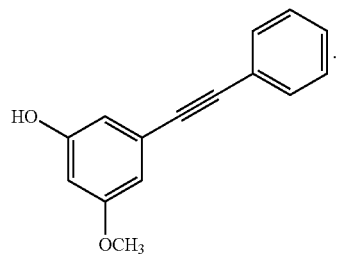

Anthelmintic Activity Assays

Two microscale assays to screen for anthelmintic activity were developed and employed: the "motility assay" and the "developmental assay." The motility assay screens the animals for paralysis, which is the final outcome of treatment with most existing anthelmintic drugs and is easy to detect in worms grown in liquid culture. Although different classes of anthelmintics cause paralysis, they accomplish this task by distinct mechanisms with different target proteins. Therefore, a synthetic compound from our library that caused nematode paralysis might do so by a molecular mechanism that is different from existing anthelmintics. To allow us to detect activities that might negatively affect aspects of nematode function other than the neuromuscular system, the developmental assay screens animals for developmental arrest prior to sexual maturity, a decrease in fecundity, or lethality. We have successfully adapted both assays to 96-well microtiter plates.

Prior to conducting the motility or developmental assays, the proper assay conditions and controls were determined. All of the synthetic derivatives were first dissolved in DMSO, which is somewhat toxic to living organisms. It was determined that worms could survive and maintain normal motility and development in DMSO levels of 3% or lower (data not shown). Because the most concentrated drug solution the worms were exposed to in either assay was a 1/100 dilution from the stilbene stock, worms were never exposed to DMSO levels exceeding 1%. Thus, deleterious effects from solvent alone were not an issue.

Figure 9A:
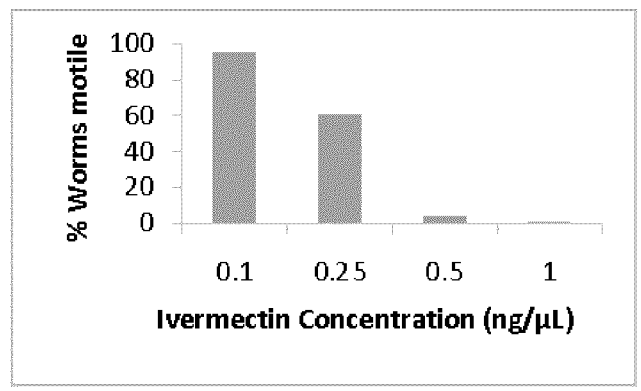
Figure 9B:
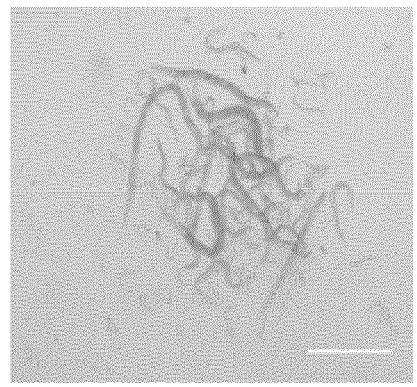
Figure 9C:
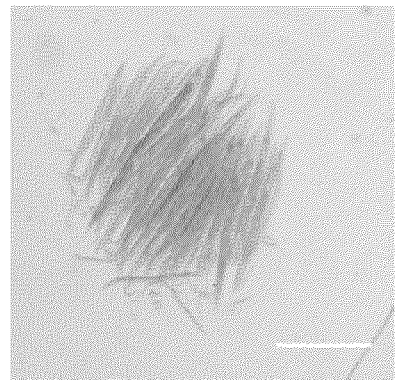

As a positive control, worms were exposed to ivermectin, which is a highly studied and commonly used anthelmintic agent known to target the neuromuscular system of nematodes and cause paralysis. Animals were incubated in microtiter plates overnight with concentrations of ivermectin ranging from 0.1 ng/µL to 1 ng/µL. Over 40% of animals were affected at 0.25 ng/µL (~140 nM), which represented the lowest effective concentration, while more than 90% of animals in each well were paralyzed at the 0.5 ng/µL treatment (FIG. 9A). All worms were paralyzed in the 1 ng/µL treatment (FIGS. 9B, 9C). Values for ivermectin sensitivity in the literature range greatly from 1 nM to over 100 times that concentration. These values depend in large part on the developmental stage of the nematodes, whether the animals are soaked in the drug solution or fed the drug on culture plates, and whether the researchers were reporting the lowest effective concentration or when 100% of the exposed animals were affected. The ivermectin concentrations at which we saw >90% paralysis fell within that range, but were near the high end. We attribute this to using a mixed population of animals, including many adults instead of L1 larvae, and the exposure via soaking, which requires the drug to cross the cuticular barrier. It has been estimated that soaking vs. feeding alone can require up to 1,000 times more of the drug due to the thickness of the proteinaceous cuticle. This suggests that any test compound that showing an effect with our assay must have a relatively low $LD_{50}$.

Screening for Anthelmintic Activity with the Motility Assay

The motility assay is a short-term assay where nematodes at various stages of the life cycle are rinsed off culture plates with standard M9 buffer, washed several times, and then incubated in the presence of test compound at 20° C. overnight. Animals were incubated in M9 buffer alone as the negative control or in the presence of 1 ng/µL of ivermectin for the positive control. The compounds were provided at a concentration of 10.24 mg/mL, and serial dilutions were performed to more accurately obtain lower concentrations for testing. A total of 67 synthetic compounds were initially screened in the motility assay at higher concentrations (serial dilutions from the stock in the range of 1/50-1/200; data not shown). Thirty-nine synthetic derivatives that showed activity in the first round of screening, or had structural similarities to compounds that showed the strongest activities, were then re-screened at lower concentrations, with dilutions up to 1/1600 or ~6.4 ng/mL the results of which are shown in Table 7. The movement of animals was scored and classified as "normal" (−), "slow" (+), "very slow" (++), or "no movement/straightened" (+++). Animals determined to be "normal" moved in a manner similar to those in the M9-only control wells. "Slow" worms moved around but not as vigorously as those in the M9-only wells, and these often showed signs of distress (jerky or uncoordinated movements). Animals exhibiting "very slow" movements only moved when agitated (tapping the plate or removing fluid from the well) and only moved the head or tail ends of their bodies. Worms that never moved, even when agitated, were classified in the "no movement/straightened" category. All of the compounds were tested at least in triplicate, and six caused reduced motility, paralysis, or death in worms at the lowest concentrations tested (A9, A10, CL-5, SK-03-28F₂, SK-04-23, and SK-05-17). Of these, CL-5 and SK-05-17 were the most active, causing severe distress in worms at the lowest concentration tested. While these were the most active compounds tested so far, they still showed less activity than ivermectin at 6.4 times the concentration. The exact molecular weight of each compound is different, but on average, when they were compared using molarity, the lowest effective concentration was between 200-400 nM. These data illustrate the need for further refinement of these compounds.

TABLE 7

Motility Assay Data for Several Synthetic Derivatives

| Synthetic Compound | 1/1600 | 1/800 | 1/400 | 1/200 | 1/100 |
|---|---|---|---|---|---|
| A6 | − | + | ++ | +++ | +++ |
| A8 | + | + | ++ | ++ | +++ |
| A9* | + | ++ | ++ | +++ | +++ |
| A10* | + | ++ | +++ | +++ | +++ |
| CL-1 | − | − | − | +++ | +++ |
| CL-2 | − | − | +++ | +++ | +++ |
| CL-3# | − | − | + | +++ | +++ |
| CL-4 | − | + | ++ | +++ | +++ |
| CL-5* | ++ | +++ | +++ | +++ | +++ |
| CL-6 | − | − | +++ | +++ | +++ |
| SK-03-28F2* | − | ++ | ++ | +++ | +++ |
| SK-03-77 | − | − | − | − | − |
| SK-03-92## | − | − | − | − | + |
| SK-04-03 | − | + | + | ++ | ++ |
| SK-04-08 | + | + | ++ | +++ | +++ |
| SK-04-22 | − | − | + | + | ++ |
| SK-04-23* | + | ++ | ++ | ++ | ++ |
| SK-04-48 | − | − | − | + | + |
| SK-04-48F1 | − | + | − | − | +++ |
| SK-04-50 | + | + | + | + | ++ |
| Ive (1 ng/μL) | +++ | +++ | +++ | +++ | +++ |
| SK-04-57 | − | − | − | − | + |
| SK-04-59F1 | − | − | − | − | − |
| SK-05-01 | − | − | − | − | + |
| SK-05-02 | − | − | + | + | + |
| SK-05-03 | − | − | − | + | + |
| SK-05-13 | − | − | − | − | − |
| SK-05-14 | − | − | − | + | ++ |
| SK-05-15 | − | − | − | − | − |
| SK-05-16 | − | + | ++ | ++ | ++ |
| SK-05-17* | ++ | ++ | ++ | ++ | ++ |
| SK-05-21 | − | − | ++ | +++ | +++ |
| SK-05-22 | − | + | ++ | +++ | +++ |
| SK-09-06 | − | − | − | − | − |
| SK-09-54 | − | − | − | ++ | ++ |
| SK-09-61 | − | − | − | − | − |
| VR-072209-01 | − | − | − | − | − |
| VR-072209-02 | − | − | − | − | − |
| VR-072309-01 | − | + | +++ | +++ | +++ |
| VR-072309-02 | − | − | − | − | − |
| M9 + DMSO | − | − | − | − | − |
| M9 Only | − | − | − | − | − |

[1]Movements scored as normal (−), slow (+), very slow (++), or not motile/paralyzed (+++).
[2]M9 only, M9 + DMSO, and ivermectin (Ive; 1 ng/μL in all wells) controls also included.
CL-3 is the parent compound from which all of the other synthetic compounds were derived.
SK-03-92 was provided at 1.024 μg/μL (all others 10.24 μg/μL), but was diluted in the same manner as the other compounds in the assay.
*Extracts marked with an asterisk consistently showed activity (distress, paralysis, and/or death) at the lowest tested concentrations.

Screening for Anthelmintic Activity with the Developmental Assay

The developmental assay is a longer-term assay that monitors developmental progression, reproduction, and death in nematodes. In brief, a synchronized population of C. elegans L1 larvae was generated and suspended in M9 buffer to a density of 10-20 worms per 50 μL volume. These worms were added to individual wells of a microtiter plate that already contained a prepared media solution with E. coli (food), ampicillin (antibiotic), and nystatin (anti-fungal). The plate was incubated at 20° C. for 4-5 days, and the worms were observed and scored every day. Variations in developmental progress were noted by comparing worms in the treated wells to worms in the wells containing only M9 buffer, the results of which are shown in Table 8. The majority of worms treated with the lowest concentrations of the synthetic compounds developed at the same rate as worms in the untreated wells (−), and the two highest concentrations were lethal (+++) to the worms for twelve of the sixteen synthetic compounds. Some compounds caused severe distress (++) to nematodes in the test wells. There were five instances of worms that were delayed but otherwise healthy (+). Two compounds (CL-5 and SK-05-22) showed death or delays in development at the two highest dilutions.

TABLE 8

Developmental Assay Data for Several Synthetic Derivatives (After Four Days)

| Synthetic Compound | 1/1600 | 1/800 | 1/400 | 1/200 | 1/100 |
|---|---|---|---|---|---|
| M9 only | Adults, many L1s and embryos | Adults, many L1s and embryos | Adults, many L1s and embryos | Adults, many L1s and embryos | Adults, many L1s and embryos |
| A6 | − | − | + | +++ | +++ |
| A8 | − | − | − | +++ | +++ |
| A9 | − | − | +++ | +++ | +++ |
| A10 | − | − | ++ | +++ | +++ |
| CL-3 | − | − | − | + | +++ |
| CL-4 | − | − | +++ | +++ | +++ |
| CL-5* | + | +++ | +++ | +++ | +++ |
| SK-03-28F2 | − | − | − | +++ | +++ |
| SK-04-03 | − | − | − | + | +++ |
| SK-04-08 | − | − | − | +++ | +++ |
| SK-04-23 | − | − | + | +++ | +++ |
| SK-04-50 | − | − | − | + | +++ |
| SK-05-16 | − | − | − | − | ++ |
| SK-05-17 | − | − | ++ | ++ | +++ |
| SK-05-22* | − | + | +++ | +++ | +++ |
| Ive (1 ng/μL) | ++ | ++ | +++ | +++ | +++ |
| M9 + DMSO | − | − | − | − | − |

[1]Worms were monitored in M9-only wells to ensure that they could develop to fertile adults under assay conditions.
[2]Worms were scored as dead (+++), distressed (++), slightly delayed (+), or the same as M9-only untreated wells (−).
[3]Ivermectin was tested at 1 ng/μL in each well and M9 + DMSO wells had 1% DMSO, the highest percentage in the test wells.
*Extracts marked with an asterisk consistently showed activity (distress, paralysis, and/or death) at the lowest two tested concentrations.

Specific Synthesis Procedures

Scheme 1. Synthesis of 3,5-dimethoxybenzaldehyde and 3-hydroxy-5-methoxybenzaldehyde

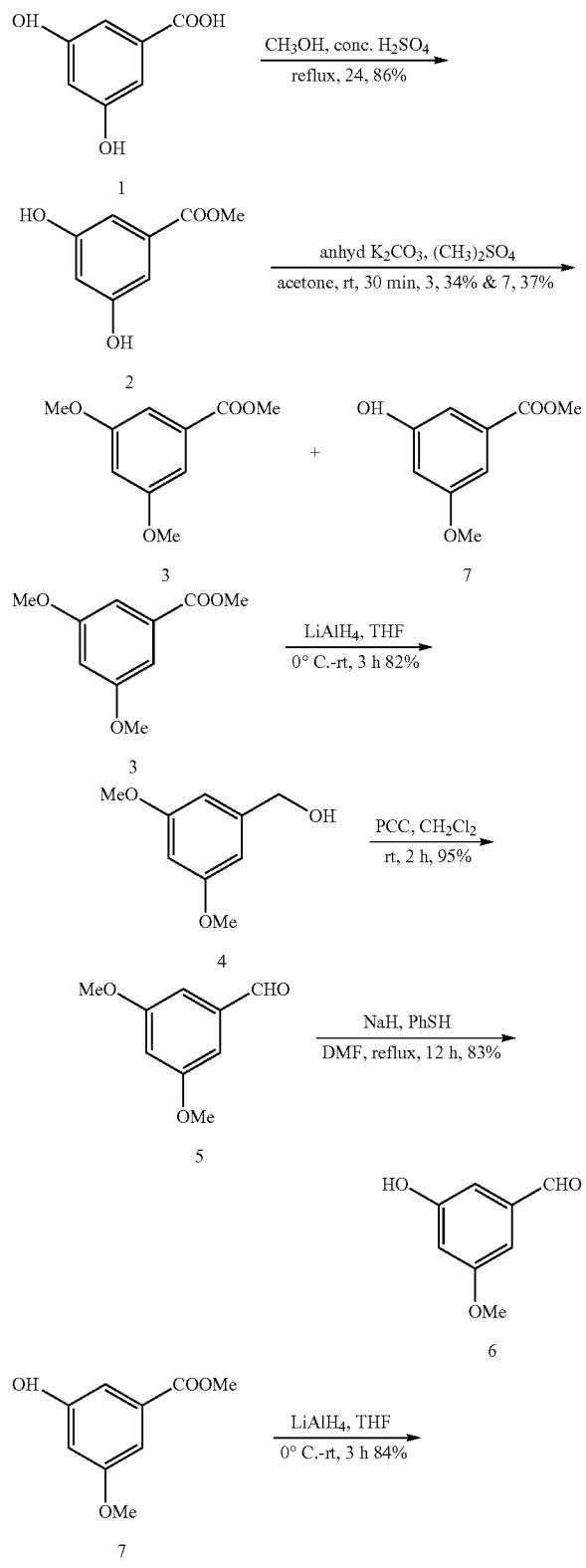

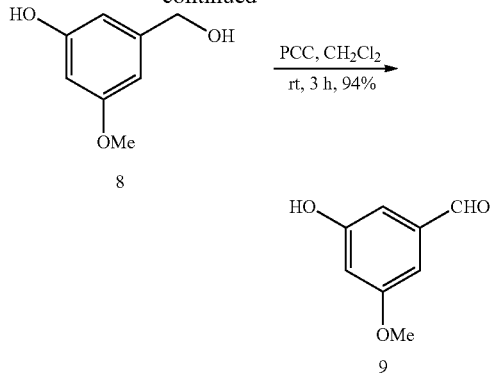

3,5-Dihydroxymethylbenzoate (2)

Concentrated $H_2SO_4$ (80 mL) was added slowly to a stirred solution of 3,5-dihydroxybenzoic acid 1 (50 g, 0.33 mol) in $CH_3OH$ (660 mL) at rt and this solution was heated to reflux for 24 h. The reaction mixture was cooled to rt and $H_2O$ (500 mL) was added to the solution. The solution was extracted with EtOAc (3×300 mL), and the combined organic extracts were washed with a saturated aq NaHCO.sub.3 solution (2×300 mL). The organic layer was dried ($Na_2SO_4$), and concentrated under reduced pressure to afford a white crude powder. The crude solid was purified by FCC (10% ethyl acetate in hexane) to afford white powdered ester 2 (48 g, 86%): $^1$H NMR (300 MHz, $CDCl_3$) δ7.10 (2H, d, J=2.4 Hz HAr), 6.57 (1H, t, J=2.0 Hz, HAr), 4.99, (2H, br, s, HO), 3.84 (3H, s, $H_3COO$). The spectral data for 2 were in excellent accord with data previously reported on 2 (Seidel et al., 1990).[1] This material was employed directly in the next step.

3,5-Dimethoxymethylbenzoate (3) & 3-hydroxy-5-methoxy methylbenzoate (7)

The $(CH_3)_2SO_4$ (51.76 mL, 69 g, 0.547 mol) was added slowly to a stirred suspension of 2 (46 g, 0.27 mol) and anhydrous $K_2CO_3$ (94.45 g, 0.6835 mol) in acetone (700 mL) at rt and this mixture was stirred for 30 min. Ice cold $H_2O$ (400 mL) was then added to the reaction mixture and the solution was extracted immediately with EtOAc (3×300 mL). The combined organic extracts were washed with brine (2×300 mL), dried ($Na_2SO_4$), and concentrated under reduced pressure to afford a yellow oil. The crude oil was purified by FCC (50% dichloromethane in hexane) to give a white powder 3 (18 g, 34%), the phenol 7 (18.5 g, 37%) and starting material 2. 3: .sup.1H NMR (300 MHz, $CDCl_3$) δ 7.11 (2H, d, J=2.4 Hz HAr), 6.56 (1H, t, J=4.5 Hz, HAr), 3.91, (3H, s, H.sub.3COO), 3.84 (6H, s, H.sub.3CO). 7: $^1$H NMR (300 MHz, $CDCl_3$) δ 7.21 (1H, dd, J=2.1 Hz, HAr), 7.16 (1H, dd, J=2.1 Hz, HAr), 6.67 (1H, t, J=3.6 Hz, HAr), 3.92 (3H, s, $H_3$COO), 3.82 (3H, s, $H_3CO$). The spectral data for 3 and 7 were in excellent accord with data previously reported on these (Seidel et al., 1990).[1] Both the materials were employed directly in the later step.

3,5-Dimethoxy benzylalcohol (4)

Ester 3 (25 g, 0.13 mol) in THF (50 mL) was added slowly to a dry stirred suspension of $LiAlH_4$ (7.25 g 0.19 mol) in THF (550 mL) at 0° C. The reaction mixture was stirred for 3 h at rt at which time all the starting material had disappeared (TLC). The reaction mixture was quenched by addition of ice-cold H$_2$O (1.0 eq), 10% aq NaOH (3.0 eq), and H$_2$O (1.0 eq), sequentially and then filtered through a Buchner funnel. The filtrate was diluted with brine (800 mL) and extracted with EtOAc (3×300 mL). The combined organic extracts were dried (Na$_2$SO$_4$) and concentrated in vacuo. The crude oil was purified by FCC (20% ethyl acetate in hexane) to afford a yellow oily alcohol 4 (17.5 g, 82%): $^1$H NMR (300 MHz, CDCl.sub.3) δ 6.53 (2H, d, J=6 Hz HAr), 6.35 (1H, t, J=2.4 Hz, HAr), 4.49 (2H, s, H$_2$COH), 3.80 (6H, s, H$_3$CO). The spectral data for 4 were in excellent accord with data previously reported on it (Seidel et al., 1990).[1] This material was employed directly in the next step.

3,5-Dimethoxybenzaldehyde (5)

Alcohol 4 (17.5 g, 0.11 mol) in CH$_2$Cl$_2$ (50 mL) was added slowly to a dry stirred suspension of freshly prepared pyridinium chlorochromate (33.64 g 0.16 mol) in CH$_2$Cl$_2$ (100 mL) at 0.degree. C. The reaction mixture was stirred for 2 h at rt after which the solvent was removed under reduced pressure on a rotatory evaporator. The residue from the reaction mixture was washed with diethyl ether (3×150 mL) and then filtered. The organic filtrate was diluted with a saturated aq solution of NaHCO$_3$3 (250 mL) and extracted with EtOAc (3×250 mL). The combined organic extracts were dried (Na$_2$SO$_4$) and concentrated in vacuo. The crude oil was purified by FCC (10% ethyl acetate in hexane) to afford a yellow solid aldehyde 5 (16.4 g, 95%): $^1$H NMR (300 MHz, CDCl$_3$) δ 9.92 (1H, s, HCO), 7.03 (2H, d, J=2.4 Hz HAr), 6.72 (1H, t, J=2.4 Hz, HAr), 3.87 (6H, s, H$_3$ CO). The spectral data for 5 were in excellent accord with data previously reported on it (Seidel et al., 1990).[1] This material was employed directly in the later step.

3-Hydroxy-5-methoxybenzylalcohol (8)

Ester 7 (17.23 g, 0.095 mol) in THF (50 mL) was added slowly to a dry stirred suspension of LiAlH$_4$ (5.38 g 0.14 mol) in THF (250 mL) at 0.degree. C. The reaction mixture was stirred for 2 h at rt until all of the starting material had been consumed (TLC). The reaction solution was quenched by addition of ice-cold H$_2$O (1.0 eq), 10% aq NaOH (3.0 eq), and H$_2$O (1.0 eq), sequentially and then filtered through a Buchner funnel. The filtrate was diluted with brine (400 mL) and extracted with EtOAc (3×200 mL). The combined organic extracts were dried (Na$_2$SO$_4$) and concentrated in vacuo. The crude oil was purified by FCC (30% ethyl acetate in hexane) to afford a yellow powdered alcohol 8 (12.25 g, 84): $^1$H NMR (300 MHz, CDCl$_3$) δ 7.5 (1H, dd, J=2.1 Hz, HAr), 6.47 (1H, dd, J=2.1 Hz, HAr), 6.35 (1H, t, J=3.6 Hz, HAr), 4.64 (2H, s, H$_2$COH), 3.81 (3H, s, H$_3$CO). The spectral data for 8 were in excellent accord with data previously reported on it (Seidel et al., 1990).[1] This material was employed directly in the next step.

3-Hydroxy-5-methoxybenzaldehyde (6)

Alcohol 6 was prepared from two different starting materials, 5 and 8, employing two different methods.
a. Alcohol 8 (12.4 g, 0.08 mol) in CH$_2$Cl$_2$ (40 mL) was added slowly to a dry stirred suspension of freshly prepared pyridinium chlorochromate (25.96 g 0.12 mol) in CH$_2$Cl$_2$ (80 mL) at 0° C. The reaction mixture was stirred for 2 h at rt and the solvents were removed under reduced pressure on a rotatory evaporator. The residue was diluted with diethyl ether, shaken and decanted (3×100 mL). The combined organic layer was diluted with a saturated aq solution of NaHCO$_3$ (200 mL) and then extracted with EtOAc (3×200 mL). The combined organic extracts were dried (Na$_2$SO$_4$) and concentrated in vacuo. The crude oil was purified by FCC (20% ethyl acetate in hexane) to afford a yellow oily aldehyde 6 (16.4 g, 95%).

b. The NaH (60% dispersed in mineral oil, 3.6 g, 0.090 mol) was added to anhydrous DMF (100 mL) at 0° C. The PhSH (12.2 mL, 13.22 g, and 0.12 mol) was then added dropwise and stirred at 0° C. for 30 min. The aldehyde 5 (5.0 g, 0.03 mol) in dry DMF (30 mL) was added dropwise to the reaction mixture. This mixture was heated to 140° C. and stirred for 12 h at this temperature. The reaction mixture was then cooled to rt, and quenched by addition of brine (540 mL). This was followed by addition of formaldehyde (37% aq. 42 mL) and HOAc (68 mL). This mixture was extracted with EtOAc (3×200 mL). The combined organic layers were washed sequentially with a saturated aq solution of NH$_4$Cl (3×60 mL), and with brine (3×60 mL). The organic layer was dried (Na$_2$SO$_4$), and the solvent was removed in vacuo. The crude oil was purified by FCC (20% ethylacetate in hexane) to afford a yellow oil of aldehyde[2] 6 (3.8 g, 83%): $^1$H NMR (300 MHz, CDCl$_3$) δ 9.90 (1H, s, HCO), 7.02 (1H, dd, J=2.1 Hz, HAr), 6.98 (1H, dd, J=2.1 Hz, HAr), 6.70 (1H, t, J=2.7 Hz, HAr), 3.86 (3H, s, H$_3$CO). The spectral data for 8 were in excellent accord with data previously reported on it (Seidel et al., 1990).[1] This material was employed directly in the next step.

Scheme 2. General Scheme for the Synthesis of β-iodostyrenes

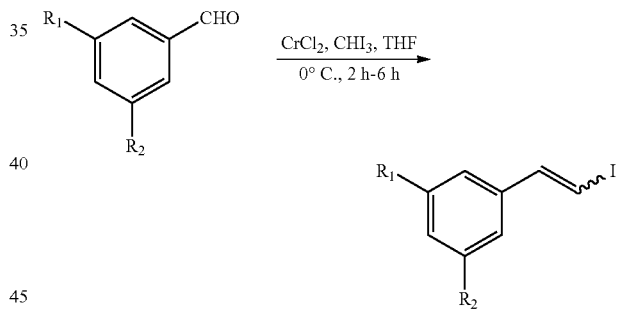

9, R$_1$ = H, R$_2$ = H, 85% E:Z 94:6
10, R$_1$ = OH, R$_2$ = OMe, 92% E:Z 94:6
11, R$_1$ = OMe, R$_2$ = OMe, 84% E:Z 92:8

1-(E)-Styryl iodide (9)

A solution of benzaldehyde (2 g, 0.019 mol) and iodoform (14.9 g, 0.038 mol) in THF (90 mL) was added to a suspension of anhydrous CrCl$_2$ (14.0 g, 0.11 mol) in dry THF (195 mL) under argon at 0° C.[3] The reaction mixture was stirred at 0° C. for 3 h and then poured into water and extracted with ether (3×200 mL). The combined organic extracts were dried (Na$_2$SO$_4$) and concentrated in vacuo. The crude oil was purified by FCC (1% ethylacetate in hexane) to afford a yellow oily mixture of E and Z isomers (E:Z 94:6) of vinyliodide 9 (3.8 g, 85%): $^1$H NMR (300 MHz, CDCl$_3$) δ 7.46 (1H, d, J=15 Hz Hz, HC=), 7.35-728 (5H, m, HAr), 6.85 (1H, d, J=15 Hz, (HC=); $^{13}$C NMR (75 MHz, CDCl$_3$) δ 144.9, 137.6, 128.6, 128.3, 125.9, 80.6; LRMS (EI), m/z (relative intensity) 230 ([M]$^+$, 100), 199 (10), 165 (9), 145 (7), 127 (27). The spectral data for 9 were in excellent accord with data previously reported on it (Takai, K. et al., 1986).[3] This material was employed directly in the later step.

1-(E)-(3-Hydroxy-5-methoxy)-styryl iodide (10)

A solution of aldehyde 6 (1 g, 0.007 mol) and iodoform (5.2 g, 0.013 mol) in THF (30 mL) was added to a suspension of anhydrous $CrCl_2$ (4.8 g, 0.04 mol) in dry THF (65 mL) under argon at 0° C. The reaction mixture was stirred at 0° C. for 2 h and then poured into water and extracted with ether (3×100 mL). The combined organic extracts were dried ($Na_2SO_4$) and concentrated in vacuo. The crude oil was purified by gradient FCC (hexane, and 2% ethyl acetate in hexane, 5% ethyl acetate in hexane) to afford a yellow oily mixture of E and Z isomers (E:Z 94:6) of vinyl iodide 10 (1.6 g, 92%): $^1$H NMR (300 MHz, $CDCl_3$) δ 7.34 (1H, d, J=15 Hz, HC=), 6.97 (1H, d, J=15 Hz, HC=), 6.42 (1H, t, J=2.0 Hz, HAr), 6.39 (1H, t, J=2.0 Hz, HAr), 6.32 (1H, t, J=2.5 Hz, HAr), 5.05 (1H, br, s, HO—), 3.80 (3H, s, $H_3CO$); $^{13}$C NMR (75 MHz, $CDCl_3$) δ161.0, 158.3, 144.9, 139.4, 105.1, 102.8, 101.0, 75.9, 54.2; LRMS (EI), m/z (relative intensity) 276 ([M]$^+$ 100), 184 (16), 149 (68), 134 (68), 106 (29). This material was employed directly in the later step.

1-(E)-(3,5-Dimethoxy)-styryliodide (11)

A solution of aldehyde 5 (2 g, 0.012 mol) and iodoform, $CHI_3$ (9.9 g, 0.024 mol) in THF (60 mL) was added to a suspension of anhydrous $CrCl_2$ (8.9 g, 0.07 mol) in dry THF (100 mL) under argon at 0° C. The reaction mixture was stirred at 0° C. for 6 h and then poured into water and the solution was extracted with ether (3×200 mL). The combined organic extracts were dried ($Na_2SO_4$) and concentrated in vacuo. The crude oil was purified by FCC on silica gel (1% ethyl acetate in hexane) to afford a yellow oily mixture of E and Z isomers (E:Z, 92:8) of vinyl iodide 11 (2.9 g, 84%): $^1$H NMR (300 MHz, $CDCl_3$) δ 7.36 (1H, d, J=14.7 Hz, HC=), 6.84 (1H, d, J=14.7 Hz, HC=) 6.46-6.42 (3H, m, HAr), 3.82 (6H, s, $H_3CO$); $^{13}$C NMR (75 MHz, $CDCl_3$) δ 160.8, 144.8, 139.4, 104.1, 100.8, 77.1, 55.3. This vinyl iodide 11 was employed directly in the later step.

Scheme 3. General Scheme for the O-vinylation of phenol or Substituted phenols and S-vinylation of thiophenols by Reaction with 1-(E)-(3-hydroxy-5methoxy)-styryliodide, 10

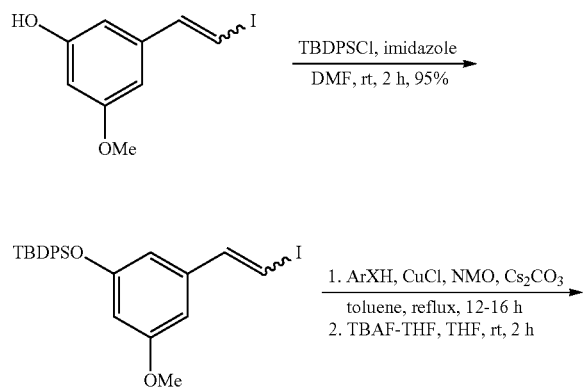

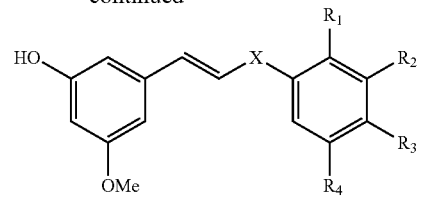

CL-1, CL-4, 13-17

CL-1, $R_1 = H$, $R_2 = R_3 = H$, $R_4 = H$, X = O 54%
CL-4, $R_1 = H$, $R_2 = R_3 = H$, $R_4 = H$, X = S 46%
13, $R_1 = CH_3$, $R_2 = R_3 = H$, $R_4 = H$, X = O, 52%
14, $R_1 = R_3 = H$, $R_2 = CH_3$, $R_4 = H$, X = O, 56%
15, $R_1 = R_2 = H$, $R_3 = CH_3$, $R_4 = H$, X = O, 51%
16, $R_1 = R_3 = H$, $R_2 = OMe$, $R_4 = H$, X = O, 50%
17, $R_1 = R_2 = H$, $R_3 = OMe$, $R_4 = H$, x = O, 49%
(Percentages are overall yields from 10 to ether or thioether)

1-(E)-(5-Dimethoxy-3-tert-butyldiphenylsilyloxy)-styryl iodide (12)

tert-Butyldiphenylsilyl chloride (TBDPSCl) (1.36 mL, 1.47 g, 5.33 mmol) was added slowly to a solution of vinyl iodide 10 (981 mg, 3.55 mmol) and imidazole (484 mg, 7.11 mmol) in dry DMF (5 mL) under argon at rt. The mixture was allowed to stir for 2 h. The reaction mixture was diluted with $H_2O$ (25 mL) and extracted with EtOAc (3×25 mL). The combined organic extracts were washed with 1M of aq HCl (2×25 mL), and brine (2×25 mL). The organic extract was dried ($Na_2SO_4$) and concentrated in vacuo. The crude oil was purified by FCC on silica gel (5% ethyl acetate in hexane) to afford vinyl iodide 12 (1.79 g, 95%): $^1$H NMR (300 MHz, $CDCl_3$) δ 7.75-7.72 (4H, m, HAr), 7.49-7.37 (6H, m, HAr), 7.21 (1H, d, J=15 Hz, HC=), 6.57 (1H, d, J=15 Hz, HC=) 6.37 (1H, t, J=1.8 Hz, HAr), 6.33 (1H, t, J=1.8 Hz, HAr), 6.26 (1H, t, J=2.4 Hz, HAr), 3.59 (3H, s, $H_3CO$), 1.13 (9H, s, $(H_3C)C$—); $^{13}$C NMR (75 MHz, $CDCl_3$) δ 160.3, 156.7, 144.6, 139.0, 135.4, 132.6, 129.9, 127.7 109.9, 105.7, 105.0, 55.1, 26.5; LRMS (EI), m/z (relative intensity): 514([M]$^+$46), 457 (100), 379 (15), 331 (25), 251 (19).

Phenyl-E-(3-hydroxy-5-methoxy)-styryl ether (CL-1)

The coupling of phenol (726 mg, 7.72 mmol) and vinyl iodide 12 (1.99 g, 3.86 mmol) was carried out according to general procedure B. The crude oil was purified by FCC on silica gel (10% ethyl acetate in hexane) to afford CL-1 (silyl group comes off during the coupling reaction) and silylvinyl ether CL-1i. The reaction of silylvinyl ether CL-1i (263 mg, 0.55 mmol) with TBAF.THF (1.0 M, 0.58 mL, 1.1 eq) in THF (5 mL) gave the crude CL-1, according to general procedure C. The crude oil was purified by FCC on silica gel (5% ethyl acetate in hexane) and afforded pure vinyl ether CL-1; overall yield of CL-1 from 12 (505 mg, 54%). CL-1i: $^1$H NMR (300 MHz, $CDCl_3$) δ 7.76-7.73 (4H, m, HAr), 7.46-7.33 (8H, m, HAr), 7.12 (1H, t, J=7.5 Hz, HAr), 6.99 (2H, d, J=7.8 Hz, HAr), 6.87 (1H, d, J=12.6 Hz, HC=), 6.37 (1H, t, J=1.5 Hz, HAr), 6.34 (1H, t, J=1.5 Hz, HAr), 6.20 (1H, t, J=2.1 Hz, HAr), 6.12 (1H, d, J=12.3 Hz, HC=) 3.60 (3H, s, $H_3CO$), 1.13 (9H, s, $(H_3C)C$—); $^{13}$C NMR (75 MHz, $CDCl_3$) δ: 160.5, 156.9, 156.8, 143.6, 135.5, 132.9, 129.8, 129.6, 129.1, 127.7, 123.1, 116.8, 113.2, 109.2, 104.9, 103.9, 55.0, 26.5; LRMS (EI), m/z (relative intensity): 480([M]$^+$, 48), 423 (39), 332 (28), 275 (100), 197 (36). CL-1: $^1$H NMR (300 MHz, $CDCl_3$) δ 7.40-7.35 (2H, m, HAr), 7.19-7.06 (4H, m, HAr & HC=), 6.46 (1H, t, J=1.5 Hz, HAr), 6.42 (1H, t, J=1.5 Hz, HAr), 6.30 (1H, t, J=2.4 Hz, HAr), 6.25 (1H, d, J=12.3 Hz, HC=), 4.97 (1H, br, s, HO—), 3.80 (3H, s, H$_3$CO); $^{13}$C NMR (75 MHz, CDCl$_3$) δ: 161.0, 156.9, 156.7, 144.1, 137.4, 129.7, 123.3, 116.9, 113.1, 105.0, 104.1, 99.8, 55.2; LRMS (CI), m/z (relative intensity): 243([M+1]$^+$, 5), 194 (25), 151 (100), 95 (30), 63 (27); HRMS calcd for C$_{15}$H$_{14}$O$_3$ 242.0943, Found 242.1025.

2-Methylphenyl-E-(3-hydroxy-5-methoxy)-styryl ether (13)

The coupling of o-cresol (0.09 mL, 94.08 mg, 0.87 mmol) and vinyl iodide 12 (300 mg, 0.58 mmol) was carried out according to general procedure B. The crude oil was purified by FCC on silica gel (3% ethylacetate in hexane) to afford ether 13 and the silylvinylether intermediate of 13. The reaction of the silylvinyl ether intermediate 13 (49 mg, 0.01 mmol) with TBAF-THF (1.0 M, 0.12 mL, 1.1 eq) in THF (3 mL) gave the crude oil of 13, according to the general procedure C. The crude oil was purified by FCC on silica gel (7% ethyl acetate in hexane) and afforded pure vinyl ether 13; overall yield of ether 13 from 12 (76 mg, 52%): $^1$H NMR (300 MHz, CDCl$_3$) δ 7.24-7.14 (3H, m, HAr & HC=), 7.06-6.99 (2H, m, HAr), 6.44 (1H, t, J=1.2 Hz, HAr), 6.39 (1H, t, J=1.2 Hz, HAr), 6.28 (1H, t, J=2.1 Hz, HAr), 6.15 (1H, d, J=12.6 Hz, HC=), 4.81 (1H, br, s, HO—), 3.80 (3H, s, H$_3$CO), 2.31 (3H, s, H$_3$C); $^{13}$C NMR (75 MHz, CDCl$_3$) δ 160.9, 156.8, 156.5, 145.0, 144.1 137.6, 131.2, 127.0, 123.5, 116.6, 111.9, 104.9, 103.9, 99.6, 55.2, 15.9.

3-Methylphenyl-E-(3-hydroxy-5-methoxy)-styryl ether (14)

The coupling of m-cresol (94.08 mg, 0.87 mmol) with vinyl iodide 12 (300 mg, 0.58 mmol) was carried out according to general procedure B. The crude oil was purified by FCC on silica gel (5% ethyl acetate in hexane) to afford vinyl ether 14 and the silylvinyl ether intermediate of 14. The reaction of the silylvinyl ether intermediate of 14 (51 mg, 0.01 mmol) with TBAF.THF (1.0 M, 0.12 mL, 1.1 eq) in THF (3 mL) gave the crude oil of vinyl ether 14, according to general procedure C. The crude oil was purified by FCC on silica gel (5% ethyl acetate in hexane) to afford pure vinyl ether 14; overall yield of vinyl ether 14 from 12 (84 mg, 56%): $^1$H NMR (300 MHz, CDCl$_3$) δ 7.28-7.14 (2H, m, HAr & HC=), 6.96-6.87 (3H, m, HAr), 6.47 (1H, t, J=1.2 Hz, HAr), 6.42 (1H, t, J=1.2 Hz, HAr), 6.30 (1H, t, J=2.1 Hz, HAr), 6.24 (1H, d, J=12.3 Hz, HC=), 4.93 (1H, br, s, HO—), 3.81 (3H, s, H$_3$CO), 2.38 (3H, s, H$_3$C); $^{13}$C NMR (75 MHz, CDCl$_3$) δ 161.0, 156.8, 156.7, 144.2, 139.9, 137.5, 129.4, 124.1, 117.6, 113.9, 112.8, 105.0, 104.1, 99.7, 55.2, 21.3; LRMS (EI), m/z (relative intensity): 256 [M]$^+$, 241, 91, 77, 63.

4-Methylphenyl-E-(3-hydroxy-5-methoxy)-styryl ether (15)

The coupling of p-cresol (94.08 mg, 0.87 mmol) with vinyl iodide 12 (300 mg, 0.58 mmol) was carried out according to general procedure B. The crude oil was purified by FCC on silica gel (3% ethylacetate in hexane) to afford vinyl ether 15 and the silylvinyl ether intermediate of 15. The reaction of the silylvinyl ether intermediate of 15 (48 mg, 0.01 mmol) with TBAF.THF (1.0 M, 0.12 mL, 1.1 eq) in THF (3 mL) gave the crude oil of vinyl ether 15, according to the general procedure C. The crude ether was purified by FCC on silica gel (7% ethyl acetate in hexane) to afford vinyl ether 15; overall yield of vinyl ether 15 from 12 (75 mg, 51%): $^1$H NMR (300 MHz, CDCl$_3$) δ 7.18-7.12 (3H, m, HAr & HC=), 6.98-6.95 (2H, m, HAr), 6.45 (1H, t, J=1.2 Hz, HAr), 6.41 (1H, t, J=1.2 Hz, HAr), 6.29 (1H, t, J=2.1 Hz, HAr), 6.21 (1H, d, J=12.3 Hz, HC=), 5.21 (1H, br, 5, HO—), 3.79 (3H, s, H$_3$CO), 2.35 (3H, s, H$_3$C); $^{13}$C NMR (75 MHz, CDCl$_3$) δ 161.0, 156.8, 144.6, 137.5, 135.4, 132.8, 130.1, 116.9, 112.5, 105.0, 104.0, 99.7, 55.2, 20.6; LRMS (EI), m/z (relative intensity): 256 [M]$^+$, 241, 91, 77, 65.

3-Methoxyphenyl-E-(3-hydroxy-5-methoxy)-styryl ether (16)

The coupling of m-anisole (0.094 mL, 108.5 mg, 0.87 mmol) with vinyl iodide 12 (300 mg, 0.58 mmol) was carried out according to general procedure B. The crude oil was purified by FCC on silica gel (2% ethylacetate in hexane) to afford vinyl ether 16 and silylvinyl ether intermediate 16i. The reaction of the silylvinyl ether intermediate 16i (112 mg, 0.22 mmol) with TBAF.THF (1.0 M, 0.24 mL, 1.1 eq) in THF (3 mL) gave the crude oil of vinyl ether 16, according to the general procedure C. The crude oil was purified by FCC on silica gel (2% ethyl acetate in hexane) to afford vinyl ether 16; overall yield of vinyl ether 16 from 12 (79.5 mg, 50%). 16i: $^1$H NMR (300 MHz, CDCl$_3$) δ 7.78-7.74 (4H, m, HAr), 7.45-7.37 (6H, m, HAr), 7.28-6.26 (1H, m, HAr), 6.88 (1H, d, J=12.3 Hz, HC=), 6.69-6.57 (3H, n, HAr), 6.39 (1H, t, J=1.2 Hz, HAr), 6.35, (1H, t, J=1.2 Hz, HAr), 6.22 (1H, t, J=2.1 Hz, HAr), 6.15 (1H, d, J=12.3 Hz, HC=), 3.83 (3H, s, H$_3$ CO), 3.60 (3H, s, H$_3$CO); $^{13}$C NMR (75 MHz, CDCl$_3$) δ 160.8, 160.5, 158.1, 156.8, 143.4, 134.9, 132.9, 129.8, 127.7, 113.4, 109.3, 108.9, 108.8, 104.9, 104.0, 103.0, 55.3, 55.0; LRMS (EI), m/z (relative intensity): 511 [M]$^+$, 454, 305 (100), 227, 77. 16: $^1$H NMR (300 MHz, CDCl$_3$) δ 7.29-7.26 (1H, m, HAr), 7.15 (1H, d, J=12.3 Hz, HC=), 6.70-6.62 (3H, m, HAr), 6.46 (1H, t, J=1.2 Hz, HAr), 6.41 (1H, t, J=1.2 Hz, HAr), 6.30 (1H, t, J=2.1 Hz, HAr), 6.25 (1H, d, J=12.3 Hz, HC=), 5.05 (1H, br, s, HO—), 3.83 (3H, s, H$_3$CO), 3.30 (3H, s, H$_3$CO); $^{13}$C NMR (75 MHz, CDCl$_3$) δ 161.0, 160.8, 158.1, 156.8, 143.8, 137.3, 130.1, 113.3, 109.0, 105.1, 104.1, 103.1, 99.9, 55.3, 55.2; LRMS (EI), m/z (relative intensity): 272 [M]$^+$, 255, 92, 77, 64.

4-Methoxyphenyl-E-(3-hydroxy-5methoxy)-styryl ether (17)

The coupling of p-anisole (108.5 mg, 0.87 mmol) with vinyl iodide 12 (300 mg, 0.58 mmol) was carried out according to general procedure B. The crude oil was purified by FCC on silica gel (2% ethylacetate in hexane) to afford vinyl ether 17 and the silylvinyl ether intermediate of 17. The reaction of the silylvinyl intermediate of 17 (111 mg, 0.22 mmol) with TBAF.THF (1.0 M, 0.24 mL, 1.1 eq) in THF (3 mL) gave the crude oil of vinyl ether 17, according to the general procedure C. The crude oil was purified by FCC on silica gel (2% ethyl acetate in hexane) to afford pure vinyl ether 17; overall yield of vinyl ether 17 from 12 (77.8 mg, 49%): $^1$H NMR (300 MHz, CDCl$_3$) δ 7.10 (1H, d, J=12.3 Hz, HC=), 7.03-7.00 (2H, m, HAr), 6.91-6.88 (2H, m, HAr), 6.43 (1H, t, J=1.2 Hz, HAr), 6.39 (1H, t, J=1.2 Hz, HAr), 6.28 (1H, t, J=2.1 Hz, HAr), 6.15 (1H, d, J=12.3 Hz, HC=), 5.17 (1H, br, s, HO—), 3.82 (3H, s, H$_3$CO), 3.79 (3H, s, H$_3$CO); $^{13}$C NMR (75 MHz, CDCl$_3$) δ 161.0, 156.7, 155.7, 150.8, 145.4, 137.6, 118.4, 114.7, 111.9, 104.9, 103.9, 99.6, 55.6, 55.2; LRMS (EI), m/z (relative intensity): 272 [M]$^+$, 255, 134, 109, 77.

Phenyl-E-(3-hydroxy-5methoxy)-styryl thioether (CL-4)

The coupling of thiophenol (329 mg, 2.98 mmol) with vinyl iodide 12 (770 mg, 1.5 mmol) was carried out according to general procedure B. The crude oil was purified by FCC on silica gel (20% dichloromethane in hexane) to afford vinyl thioether CL-4 and the silylvinyl thioether intermediate CL-4i. The reaction of the silylvinyl thioether intermediate CL-4i (192 mg, 0.39 mmol) mL) with TBAF.THF (1.0 M, 0.41 mL, 1.1 eq) in THF (5 mL) gave crude vinyl thioether CL-4, according to general procedure C. The crude oil was purified by FCC on silica gel (10% dichloromethane in hexane) to afford pure vinyl thioether CL-4; overall yield of thioether CL-4 from 12 (185 mg, 48%). CL-4i: $^1$H NMR (300 MHz, CDCl$_3$) δ 7.76-7.73 (4H, m, HAr), 7.43-7.28 (11H, m, HAr), 6.88 (2H, dd, J=6.0 Hz, J=2.1 Hz, HC═), 6.42 (1H, t, J=1.5 Hz, HAr), 6.39 (1H, t, J=1.5 Hz, HAr), 6.23 (1H, t, J=2.1 Hz, HAr), 3.60 (3H, s, H$_3$CO); $^{13}$C NMR (75 MHz, CDCl$_3$) δ 160.4, 156.8, 138.0, 135.4, 132.8, 131.2, 129.9, 129.0, 127.7, 126.8, 123.7, 109.8, 105.0, 104.9, 104.8, 55.1, 26.5, 19.4; LRMS (EI), m/z (relative intensity): 497[M]$^+$, 440 (100), 362, 220, 105. CL-4: $^1$H NMR (300 MHz, CDCl$_3$) δ 7.75-7.28 (5H, m, HAr), 6.87 (1H, d, J=15.3 Hz, HC═), 6.61 (1H, dd, J=15.3, HC═), 6.49 (1H, t, J=1.5 Hz, HAr), 6.44 (1H, t, J=1.5 Hz, HAr), 6.33 (1H, t, J=2.1 Hz, HAr), 5.09 (1H, br, s, HO—), 3.79 (3H, s, H$_3$CO); $^{13}$C NMR (75 MHz, CDCl$_3$) δ 161.0, 156.7, 138.7, 134.8, 130.8, 130.0, 129.1, 127.0, 124.5, 105.4, 104.4, 100.8, 55.3; LRMS (EI), m/z (relative intensity): 258[M]$^-$, 225 (100), 181, 77, 51.

Scheme 4. Synthesis of phenyl-E-(3-hydroxy-5-methoxy)-styryl ether, CL-2

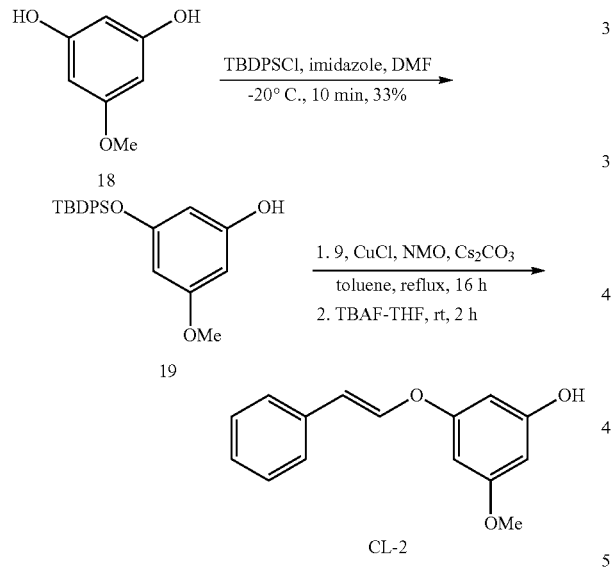

5-Methoxy-3-tert-butyldiphenylsilyloxyphenol (19)

tert-Butyldiphenylsilylchloride (TBDPSCl) (1.8 mL, 1.96 g, 7.14 mmol) was added to a suspension of 5-methoxyresorcinol 18 (1.0 g, 7.14 mmol) and imidazole (729 mg, 10.71 mmol) in dry DMF (5 mL) under argon at −22° C. and the mixture was stirred for 10 min. The reaction mixture was diluted with H$_2$O (25 mL) and extracted with EtOAc (3×25 mL). The combined organic extracts were washed with aq 1M of HCl (2×25 mL), and brine (2×25 mL). The organic layer was then dried (Na$_2$SO$_4$) and concentrated in vacuo. The crude silyl phenol 19 was purified by FCC on silica gel (5% ethyl acetate in hexane) to afford pure silyl phenol 19 (892 mg, 33%): $^1$H NMR (300 MHz, CDCl$_3$) δ 7.89-7.75 (4H, m, HAr), 7.48-7.34 (6H, m, HAr), 5.98 (2H, t, J=2.1 Hz, HAr), 5.92 (1H, t, J=2.1 Hz, HAr), 5.13 (1H, br, s, HO—), 3.56 (3H, s, H$_3$CO), 1.14 (9H, s, [(H$_3$C)$_3$C]; $^{13}$C NMR (75 MHz, CDCl$_3$) δ 161.1, 157.3, 156.8, 135.4, 132.8, 129.9, 127.7, 100.1, 98.5, 95.0, 55.0, 26.4, 19.4; LRMS (CI), m/z (relative intensity): 378([M+1]$^+$, 30), 321 (100), 243 (30), 213 (10), 199 (29). This material was employed directly in the next step.

Phenyl-E-(3-hydroxy-5methoxy)-styryl ether (CL-2)

The coupling of phenol 19 (700 mg, 1.85 mmol) with vinyl iodide 9 (425 mg, 1.85 mmol) was carried out according to general procedure B. The crude oil was purified by FCC on silica gel (5% ethyl acetate in hexane) to afford vinyl ether CL-2 and the silylvinyl ether intermediate of CL-2. The reaction of the silylvinyl ether intermediate of CL-2 (392 mg, 0.82 mmol) with TBAF-THF (1.0 M, 0.87 mL, 1.1 eq) in THF (5 mL) gave a crude oil of CL-2, according to general procedure C. The crude oil was purified by FCC on silica gel (10% ethyl acetate in hexane) and afforded pure vinyl ether CL-2; overall yield of ether CL-2 from 19 (362 mg, 52%): $^1$H NMR (300 MHz, CDCl$_3$) δ 7.35-7.33 (4H, m, HAr), 7.28-7.25 (1H, m, HAr), 7.14 (1H, d, J=12.3 Hz, HC═), 6.39 (1H, d J=12.3 Hz, HC═), 6.27 (1H, t, J=2.1 Hz, HAr), 6.22-6.19 (2H, m, HAr), 5.46 (1H, br, s, HO—), 3.79 (3H, s, H$_3$CO); $^{13}$C NMR (75 MHz, CDCl$_3$) δ 161.6, 159.0, 157.3, 142.7, 134.8, 128.7, 126.8, 125.7, 114.2, 97.0, 96.6, 95.7, 55.4; LRMS (CI), m/z (relative intensity): 242([M+1]$^+$, 100), 213 (13), 199 (13), 185 (16), 141 (24).

Scheme 5. Synthesis of phenyl-E-(3,5-dimethoxy)-styryl ether, 21

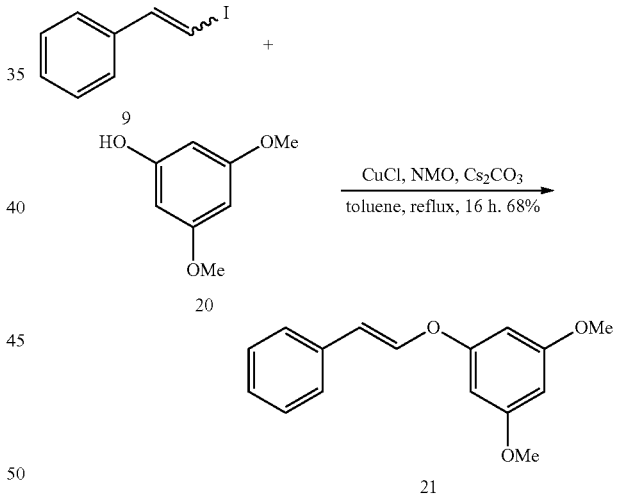

Phenyl-E-(3,5-dimethoxy)-styryl ether (21)

The coupling of 3,5-dimethoxyphenol 20 (503 mg, 3.26 mmol) with vinyl iodide 9 (500 mg, 2.17 mmol) was carried out according to general procedure$^4$ B. The crude ether was purified by FCC on silica gel (5% ethyl acetate in hexane) to afford pure vinyl ether 21 (325 mg, 68%): $^1$H NMR (300 MHz, CDCl$_3$) δ 7.34 (4H, d, J=4.2 Hz, HAr), 7.28-7.22 (1H, m, HAr), 7.17 (1H, d, J=12.6 Hz, HC═), 6.37 (1H, d J=12.6, HC═), 6.27-6.25 (3H, m, HAr), 3.81 (6H, s, H$_3$CO); $^{13}$C NMR (75 MHz, CDCl.sub.3) δ 161.5, 158.9, 142.9, 134.9, 128.6, 126.7, 125.6, 113.9, 95.4, 55.4; LRMS (CI), m/z (relative intensity): 256([M+1]$^+$100), 241 (10), 213 (10), 181 (17), 154 (80).

Scheme 6. General Scheme for the O-vinylation of phenol or Substituted phenols and S-vinylation of thiophenols with 1-E-(3,5-dimethoxy)-styryl iodide

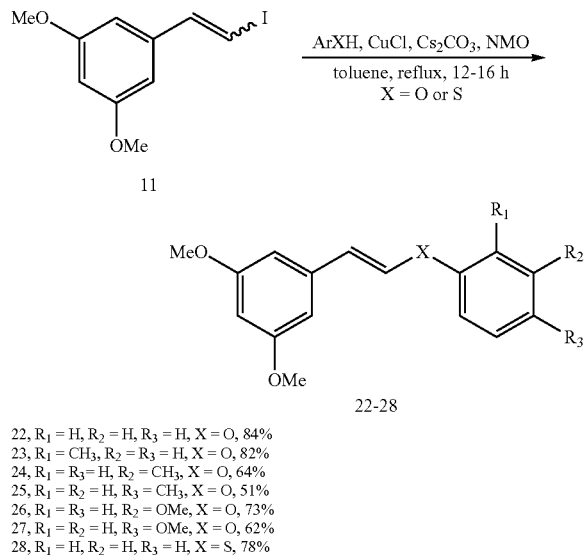

22, $R_1$ = H, $R_2$ = H, $R_3$ = H, X = O, 84%
23, $R_1$ = $CH_3$, $R_2$ = $R_3$ = H, X = O, 82%
24, $R_1$ = $R_3$= H, $R_2$ = $CH_3$, X = O, 64%
25, $R_1$ = $R_2$ = H, $R_3$ = $CH_3$, X = O, 51%
26, $R_1$ = $R_3$ = H, $R_2$ = OMe, X = O, 73%
27, $R_1$ = $R_2$ = H, $R_3$ = OMe, X = O, 62%
28, $R_1$ = H, $R_2$ = H, $R_3$ = H, X = S, 78%

3,5-Dimethoxyphenyl-E-styryl ether (22)

The coupling of phenol (454 mg, 4.84 mmol) with vinyl iodide 11 (935 mg, 3.22 mmol) was carried out according to general procedure B. The crude ether was purified by FCC on silica gel (7% ethyl acetate in hexane), to afford pure vinyl ether 22 (652 mg, 84%): $^1$H NMR (300 MHz, $CDCl_3$) δ 7.40-7.35 (2H, m, HAr), 7.19 (1H, d, J=12.6 Hz, HC═), 6.49 (2H, d, J=2.4 Hz, HAr), 6.36 (1H, t, J=2.1 Hz, HAr), 6.29 (1H, d, J=12.6 Hz, HC═), 3.82 (6H, s, $H_3CO$); $^{13}$C NMR (75 MHz, $CDCl_3$) δ 160.9, 157.0, 144.0, 137.1, 129.7, 123.3, 117.0, 113.4, 103.7, 98.7, 80.4, 55.2.

2-Methylphenyl-E-(3,5-dimethoxy)-styryl ether (23)

The coupling of o-cresol (0.16 mL, 167 mg, 1.55 mmol) with vinyl iodide 11 (300 mg, 0.1.03 mmol) was carried out according to general procedure B. The crude ether was purified by FCC on silica gel (20% dichloromethane in hexane) to afford pure vinyl ether 23 (227 mg, 82%): $^1$H NMR (300 MHz, $CDCl_3$) δ 7.28-7.19 (3H, m, HAr & HC═), 7.11-7.04 (2H, m, HAr), 6.50 (2H, d, J=2.4 Hz, HAr), 6.38 (1H, t, J=2.1 Hz, HAr), 6.22 (1H, d, J=12.6 Hz, HC═), 3.83 (6H, s, $H_3CO$), 2.35 (3H, s, $H_3C$); $^{13}$C NMR (75 MHz, $CDCl_3$) δ 160.9, 157.0, 144.9, 137.3, 131.2, 127.0, 123.5, 116.6, 112.3, 103.6, 98.6, 55.2, 16.5; LRMS (EI), m/z (relative intensity): 270[M]$^+$, 227, 362, 91, 77, 65 (100).

3-Methylphenyl-E-(3,5-dimethoxy)-styryl ether (24)

The coupling of m-cresol (167 mg, 1.55 mmol) with vinyl iodide 11 (300 mg, 1.03 mmol) was carried out according to general procedure B. The crude ether was purified by FCC on silica gel (1% ethyl acetate in hexane) to afford pure vinyl ether 24 (179 mg, 64%): $^1$H NMR (300 MHz, $CDCl_3$) δ 7.28-7.23 (1H, m, HAr), 7.19 (1H, d, J=12.3 Hz HC═), 6.96-6.88 (3H, m, HAr), 6.49 (2H, d, J=2.4 Hz, HAr), 6.37 (1H, t, J=2.1 Hz, HAr), 6.28 (1H, d, J=12.6 Hz, HC═), 3.82 (6H, s, $H_3CO$), 2.39 (3H, s, $H_3C$); $^{13}$C NMR (75 MHz, $CDCl_3$) δ 160.9, 157.0, 144.1, 139.9, 137.2, 129.4, 124.1, 117.6, 113.9, 113.2, 103.7, 98.6, 55.2, 21.3; LRMS (EI), m/z (relative intensity): 270[M]$^+$, 255, 91, 77, 65 (100).

4-Methylphenyl-E-(3,5-dimethoxy)-styryl ether (25)

The coupling of p-cresol (167 mg, 1.55 mmol) with vinyl iodide 11 (300 mg, 1.03 mmol) was carried out according to general procedure B. The crude ether was purified by FCC on silica gel (3% ethyl acetate in hexane) to afford pure vinyl ether 25 (143 mg, 51%): $^1$H NMR (300 MHz, $CDCl_3$) δ 7.20-7.16 (3H, m, HAr & HC═), 7.00-6.98 (2H, m, HAr), 6.47 (2H, d, J=2.4 Hz, HAr), 6.36 (1H, t, J=2.1 Hz, HAr), 6.26 (1H, d, J=12.3 Hz, HC═), 3.82 (6H, s, H.sub.3CO), 2.36 (3H, s, $H_3C$); $^{13}$C NMR (75 MHz, $CDCl_3$) δ 160.9, 154.9, 144.5, 137.2, 132.8, 130.1, 117.0, 112.8, 103.7, 98.6, 55.2, 20.6; LRMS (EI), m/z (relative intensity): 270[M]$^+$ (100), 255, 91, 77, 65.

3-Methoxyphenyl-E-(3,5-dimethoxy)-styryl ether (26)

The coupling of m-anisole (192 mg, 1.55 .mu.mmol) with vinyl iodide 11 (300 mg, 1.03 mmol) was carried out according to general procedure B. The reaction mixture was refluxed for 16 h. The crude ether was purified by FCC on silica gel (20% ethyl acetate in hexane) to afford pure ether 26 (216 mg, 73%): $^1$H NMR (300 MHz, $CDCl_3$) δ 7.29-7.24 (1H, m, HAr), 7.18 (1H, d, J=12.6 Hz, HC═), 6.70-6.63 (3H, m, HAr), 6.47 (2H, d, J=2.4 Hz, HAr), 6.36 (1H, t, J=2.1 Hz, HAr), 6.30 (1H, d, J=12.6 Hz, HC═), 3.82 (9H, s, $H_3CO$); $^{13}$C NMR (75 MHz, $CDCl_3$) δ 160.9, 158.1, 143.7, 137.0, 130.1, 113.6, 108.9, 103.7, 103.1, 98.8, 55.3.

4-Methoxyphenyl-E-(3,5-dimethoxy)-styryl ether (27)

The coupling of p-anisole (192 mg, 1.55 mmol) with vinyl iodide 11 (300 mg, 1.03 mmol) was carried out according to general procedure B. The reaction mixture was refluxed for 16 h. The crude ether was purified by FCC on silica gel (10% ethyl acetate in hexane) to afford pure vinyl ether 27 (183 mg, 62%): $^1$H NMR (300 MHz, $CDCl_3$) δ 7.13 (11H, d J=12.3 Hz, HC═), 7.02 (2H, d, J=8.7 Hz, HAr), 6.90 (2H, d, J=8.7 Hz, HAr), 6.45-6-34 (3H, m, HAr), 6.19 (1H, d, J=12.3 Hz, HC═), 3.80 (9H, s, $H_3CO$); $^{13}$C NMR (75 MHz, $CDCl_3$) δ 160.9, 150.8, 145.3, 137.3, 118.4, 114.7, 112.2, 103.6, 98.6, 55.5, 55.2.

Phenyl-E-(3,5-dimethoxy)-styryl thioether (28)

The coupling of thiophenol (0.15 mL, 171 mg, 1.55 mmol) with vinyl iodide 11 (300 mg, 1.03 mmol) was carried out according to general procedure B. The reaction mixture was refluxed for 12 h. The crude thioether was purified by FCC on silica gel (20% dichloromethane in hexane) to afford pure thioether 28 (171 mg, 78%): $^1$H NMR (300 MHz, $CDCl_3$) δ 7.47-7.30 (5H, m, HAr), 6.92 (1H, d, J=15.3 Hz HC═), 6.68 (1H, d, J=15.3 Hz, HC═), 6.53 (2H, d, J=1.8 Hz, HAr), 6.40 (1H, t, J=1 Hz, H), 3.81 (6H, s, $H_3CO$); $^{13}$C NMR (75 MHz, $CDCl_3$) δ 160.9, 144.9, 139.4, 138.4, 131.3, 129.9, 127.0, 104.1, 100.5, 55.3.

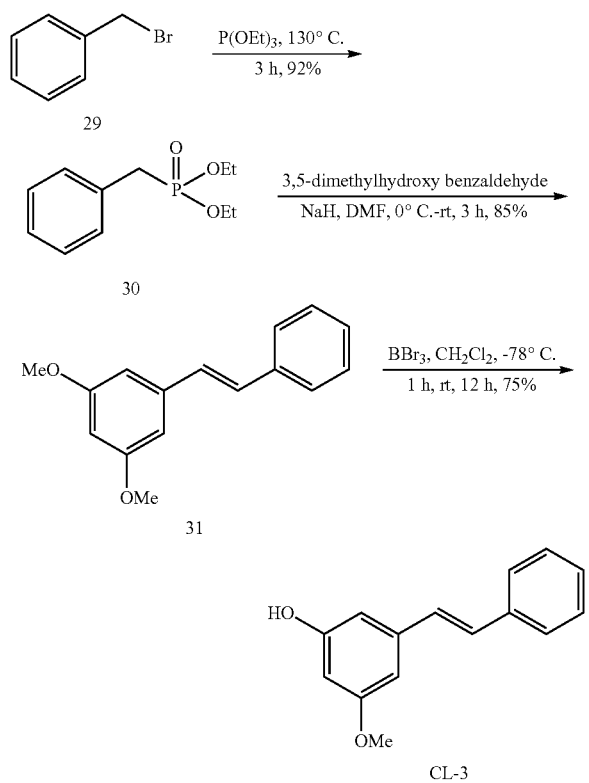

Scheme 7. Synthesis of 3,5-dimethoxystilbene (31) and 3-hydroxy-5-methoxystilbene (CL-3)

Synthesis of diethylbenzylphosphonate (30) & its conversion to 3,5-dimethoxystilbene (31)

Benzylbromide 29 (0.7 mL, 1.0 g, 5.85 mmol.) was heated with excess triethylphosphite (1.5 mL, 1.46 g, 8.76 mmol) at 130° C. under argon following general procedure D. This gave phosphonate 30 (1.23 g, 92%), which was employed directly for the next step without any further purification.[5]

The 3,5-dimethoxybenzaldehyde (1 g, 6.02 mmol) was added slowly to a combined solution of dry diethylbenzylphosphonate 30 (1.51 g, 6.62 mmol) and NaH (60% wt dispersed in mineral oil, 842 mg, 21.1 mmol) in dry DMF (5.0 mL), under argon at 0° C. This mixture was stirred at rt for 1 h. Then reaction mixture was heated to 80-90° C. and stirred for an additional 1 h. The reaction mixture was allowed to stand at rt overnight. A mixture of water-methanol (2:1) was added slowly until the stilbene 31 precipitated. The crude solid was collected by filtration and purified by FCC on silica gel (20% ethyl acetate in hexane) to afford pure stilbene 31 (1.22 g, 85%): $^1$H NMR (300 MHz, CDCl$_3$) δ 7.53 (2H, d, J=7.5 Hz, HAr), 7.38 (2H, t, J=7.2 Hz, HAr), 7.28 (1H, m, HAr), 7.09 (2H, dd, J=18 Hz, J=4.8 Hz, HC=CH), 6.70 (2H, d, J=2.1 Hz, HAr), 6.43 (1H, t, J=2.1 Hz, HAr), 3.86 (6H, s, H$_3$CO); $^{13}$C NMR (75 MHz, CDCl$_3$) δ 160.9, 139.3, 137.0, 129.1, 128.6, 127.7, 126.5, 104.5, 99.9, 55.3; LRMS (EI), m/z (relative intensity): 240[M]$^+$ (100), 209, 194, 165, 152. The spectral data for both 30, and 31 were in excellent accord with that previously reported for these compounds (Bachelor, F. W., 1970).[5]

3-hydroxy-5-methoxystilbene (CL-3)

A solution of stilbene 31 (400 mg, 1.66 mmol) in CH$_2$Cl$_2$ (5 mL) was added to a solution of BBr$_3$ (1M solution in CH$_2$Cl$_2$, 727 mg, 2.91 mmol) in CH$_2$Cl$_2$ (5 mL) at −78° C. The reaction mixture was then allowed to warm to rt and stirred overnight. The reaction mixture was shaken with a 10% aq solution of KOH (30 mL) and then brought to acidic pH by addition of 3 M of HCl. The mixture was extracted with CH$_2$Cl$_2$ (3×25 mL). The combined organic extracts were dried (Na$_2$SO$_4$) and the solvent was removed in vacuo. The solid crude stilbene was crystallized from benzene to yield stilbene CL-3 (282 mg, 75%): $^1$H NMR (300 MHz, CDCl$_3$) δ 7.51 (2H, d, J=7.2 Hz, HAr), 7.39 (2H, t, J=7.2 Hz, HAr), 7.30 (1H, t, J=7.2 Hz, HAr), 7.05 (2H, dd, J=18 Hz, J=4.8 Hz, HC=CH), 6.70 (1H, s, HAr), 6.65 (1H, s, HAr) 6.40 (1H, t, J=2.1 Hz, HAr), 3.84 (3H, s, H$_3$CO); $^{13}$C NMR (75 MHz, CDCl$_3$) δ 160.9, 156.7, 139.7, 137.0, 129.4, 128.6, 128.2, 127.7, 126.6, 106.0, 105.0, 101.0, 55.4; LRMS (EI), m/z (relative intensity): 240[M]$^+$, 226 (100), 221, 194, 165. The spectral data for stilbene CL-3 were in excellent accord with that previously reported on it (Bachelor, F. W., 1970).[5]

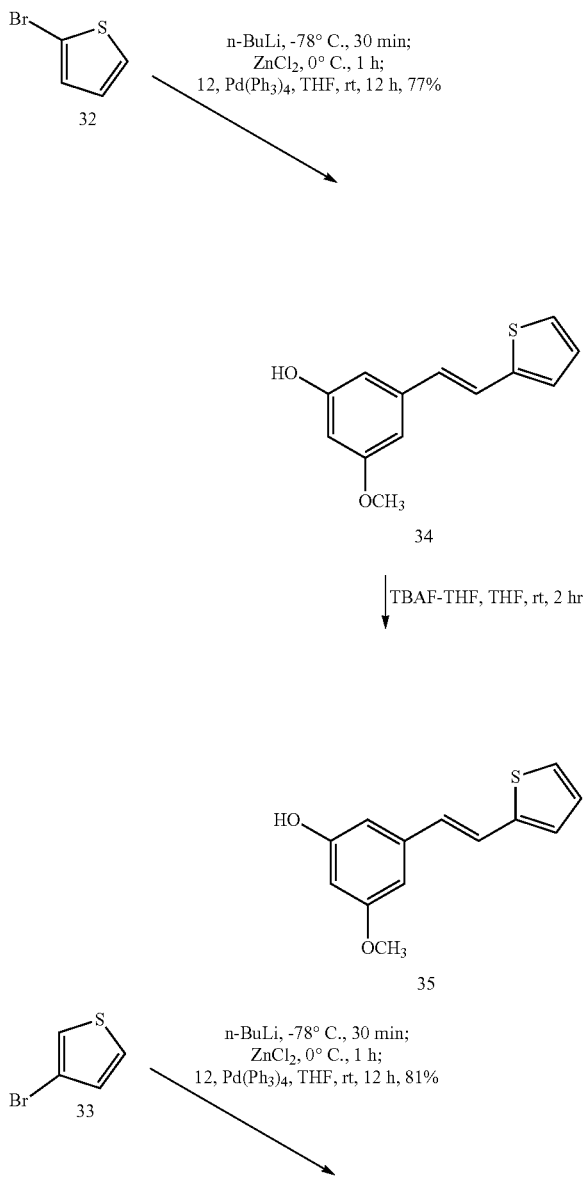

Scheme 8. Example synthesis of stilbene analogues I

-continued

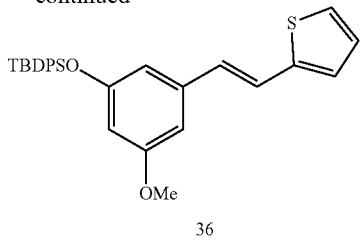

36

↓ TBAF-THF, THF, rt, 2 hr

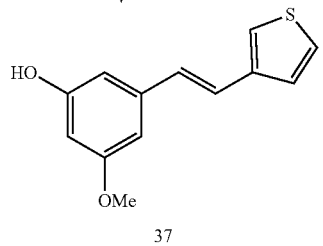

37

(E)-2-[2-(3-tert-Butyldiphenylsilyloxy-5-methoxy)-vinyl]thiophene (34)

n-Butyllithium (0.41 mL, 1.66 mmol, 2.87 M in hexane) was added to 2-bromothiophene 32 (0.08 mL, 0.85 mmol) in THF (12 mL), followed by the addition of anhydrous ZnCl$_2$ (116 mg, 0.85 mmol), the vinyl iodide 12 (400 mg, 0.78 mmol) and 12.7 mg of Pd(PPh$_3$)$_4$, (7 mol %) sequentially.[6] The exact conditions outlined in general procedure E were maintained. The crude oil of silyl stilbene analogue 34 was purified by FCC on silica gel (5% dichloromethane in hexane) to give silyl stilbene 34 (290 mg, 77%). Silyl stilbene 34 contained a little impurity; therefore, it was not fully characterized. This material was employed directly in the next step to prepare stilbene analogue 35.

(E)-2-[2-(3-Hydroxy-5-methoxy)-vinyl]thiophene (35)

The reaction of the silyl stilbene analogue 34 (280 mg, 0.60 mmol) mL) with TBAF.THF (1.0 M, 0.65 mL, 1.1 eq) in THF (5 mL) gave crude thiophene analogue 35, according to general procedure C. The crude oil was purified by FCC on silica gel (10% ethyl acetate in hexane) to afford pure thiophene analogue 35 (79 mg, 57%): $^1$H NMR (300 MHz, CDCl$_3$) δ 7.23-7.17 (2H, m, HAr & HC═), 7.09-7.08 (1H, m, HAr), 7.04-7.00 (1H, m, HAr), 6.84 (1H, d, J=16.2 Hz, HC═), 6.63 (1H, s, HAr), 6.57 (1H, s, HAr) 6.36 (1H, t, J=2.1 Hz, HAr), 5.04 (1H, br, s, HO), 3.83 (3H, s, H$_3$CO); $^{13}$C NMR (75 MHz, CDCl$_3$) δ 161.0, 156.7, 142.4, 139.3, 127.8, 127.5, 126.3, 124.5, 122.4, 105.7, 104.7, 101.0, 55.3; LRMS (EI), m/z (relative intensity): 232[M]$^+$ (100), 199, 171, 115, 69.

(E)-3-[2-(3-tert-Butyldiphenylsilyloxy-5-methoxy)-vinyl]thiophene (36)

n-Butyllithium (0.41 mL, 1.66 mmol, 2.87 M in hexane) was added to 3-bromothiophene 33 (0.08 mL, 0.85 mmol) in THF (12 mL) and this was followed by the addition of anhydrous ZnCl$_2$ (116 mg, 0.85 mmol), vinyl iodide 12 (400 mg, 0.78 mmol) and 12.7 mg of Pd(PPh$_3$)$_4$, (7 mol %) sequentially. The exact conditions outlined in the general procedure E were maintained. The crude silyl stilbene analogue 36 was purified by FCC on silica gel (5% dichloromethane in hexane) to afford the pure thiophene analogue 36 (335 mg, 81%): $^1$H NMR (300 MHz, CDCl$_3$) δ 7.78-7.74 (4H, m, HAr), 7.47-7.38 (7H, m, HAr, & HC═), 7.28 (1H, s HAr), 7.13-6.99 (1H, m, HAr), 6.98-6.95 (1H, m, HAr), 6.75 (1H, d, J=16.5 Hz, HC═) 6.58-6.56 (1H, m, HAr), 6.54-649 (1H, m, HAr), 6.25-6.24 (1H, m, HAr), 3.61 (3H, s, H.sub.3CO), 1.14 (9H, s, H$_3$C); $^{13}$C NMR (75 MHz, CDCl$_3$) δ 160.4, 156.8, 144.1, 138.1, 132.7, 130.7, 129.9, 129.3, 127.8, 123.8, 121.1, 120.7, 120.2, 110.4, 110.2, 105.5, 55.1, 26.5, 19.4; LRMS (EI), m/z (relative intensity): 470[M]$^+$, 392, 171, 105, 57.

(E)-3-[2-(3-Hydroxy-5-methoxy)-vinyl]thiophene (37)

The reaction of the silyl thiophene analogue 36 (280 mg, 0.60 mmol) mL) with TBAF.THF (1.0 M, 0.65 mL, 1.1 eq) in THF (5 mL) gave crude thiophene analogue 37, according to general procedure C. The crude thiophene analogue was purified by FCC on silica gel (7% ethyl acetate in hexane) to afford pure thiophene analogue 37 (85 mg, 61%): $^1$H NMR (300 MHz, CDCl$_3$) δ 7.27 (1H, d, J=2.7 Hz, HAr), 7.22-7.18 (2H, m, HAr, & HC═), 6.99 (1H, d, J=5.1 Hz HAr), 6.87 (1H, d, J=16.2 Hz HC═), 6.65-6.63 (2H, m, HAr), 6.37 (1H, t, J=4.2 Hz, HAr), 4.83 (1H, br, s, HO), 3.84 (3H, s, H$_3$CO); $^{13}$C NMR (75 MHz, CDCl$_3$) δ 161.1, 156.7, 138.9, 136.8, 130.7, 129.7, 124.1, 120.7, 105.7, 105.2, 101.3, 55.3; LRMS (EI), m/z (relative intensity): 232[M]$^+$ (100), 216, 200, 171, 115.

Scheme 9. Synthesis of stilbene analogues II

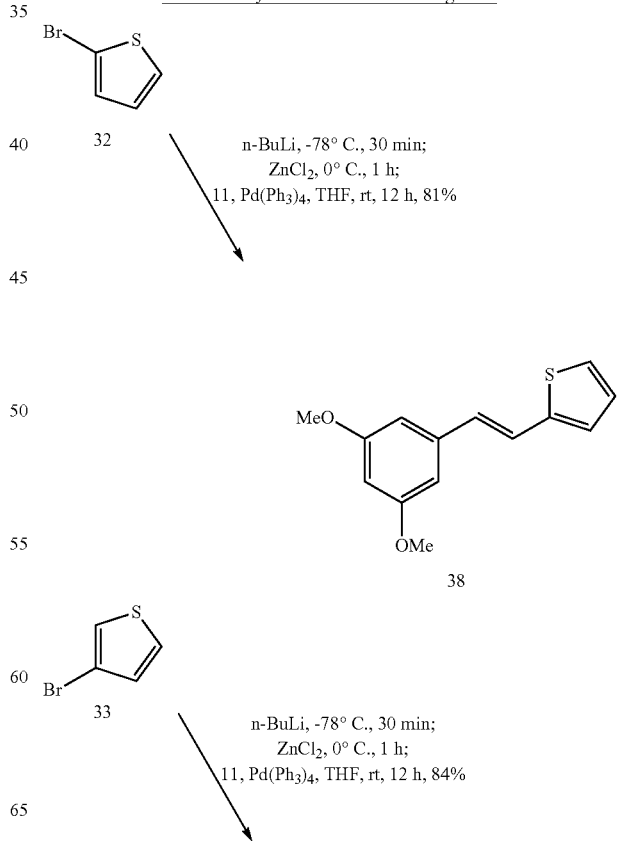

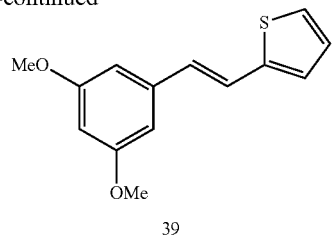

39

(E)-2-[2-(3,5-Dimethoxy)-vinyl]thiophene (38)

n-Butyllithium (0.48 mL, 1.38 mmol, 2.87 M in hexane) was added to 2-bromothiophene 32 (0.08 mL, 134.83 mg, 0.83 mmol) in THF (8 mL) and this was followed by the addition of anhydrous $ZnCl_2$ (112 mg, 0.83 mmol), vinyl iodide 11 (200 mg, 0.69 mmol) and 10 mg of $Pd(PPh_3)_4$, (7 mol %) sequentially. The exact conditions outlined in the general procedure E were maintained. The crude oil of thiophene analogue 38 was purified by FCC on silica gel (20% dichloromethane in hexane) to afford pure thiophene analogue 38 (139 mg, 82%): $^1$H NMR (300 MHz, $CDCl_3$) δ 7.28-7.21 (2H, m, HAr), 7.11-7.02 (2H, m, HAr, & HC═), 6.89 (1H, d, J=16.2 Hz, HC═), 6.65 (2H, d, J=2.4 Hz, HAr), 6.41 (1H, t, J=2.1 Hz, HAr), 3.85 (6H, s, $H_3CO$); $^{13}$C NMR (75 MHz, $CDCl_3$) δ 160.9, 143.3, 138.9, 128.2, 127.5, 126.2, 124.4, 122.2, 104.2, 100.0, 55.3; LRMS (EI), m/z (relative intensity): 246[M]⁻ (100), 213, 171, 115, 63.

(E)-3-[2-(3,5-Dimethoxy)-vinyl]thiophene (39)

n-Butyllithium (0.48 mL, 1.38 mmol, 2.87 M in hexane) was added to 3-bromothiophene 33 (0.08 mL, 134.83 mg, 0.83 mmol) in THF (8 mL) and this was followed by the addition of anhydrous $ZnCl_2$ (112 mg, 0.83 mmol), vinyl iodide 11 (200 mg, 0.69 mmol) and 10 mg of Pd $(PPh_3)_4$, (7 mol %) sequentially. The exact conditions outlined in the general procedure E were maintained. The crude oil of thiophene analogue 39 was purified by FCC on silica gel (10% dichloromethane in hexane) to afford pure thiophene analogue 39 (144 mg, 84%): $^2$H NMR (300 MHz, $CDCl_3$) δ 7.37-7.33 (2H, m, HAr), 7.29-7.27 (1H, m, HAr), 7.13 (1H, d, J=15.9 Hz, HC═), 6.91 (1H, d, J=16.2 Hz, HC═), 6.66 (2H, d, J=2.1 Hz, HAr), 6.41 (1H, t, J=2.1 Hz, HAr), 3.85 (6H, s, $H_3CO$); $^{13}$C NMR (75 MHz, $CDCl_3$) δ 160.9, 139.8, 139.3, 128.5, 126.1, 124.8, 123.3, 122.5, 104.3, 99.7, 55.3; LRMS (EI), m/z (relative intensity): 246[M]⁺ (100), 231, 215, 171, 115.

Scheme 10. Synthesis of 3-(E)-2-(benzo[b]thiophen-2-yl)vinyl-5methoxyphenol, SK-03-92

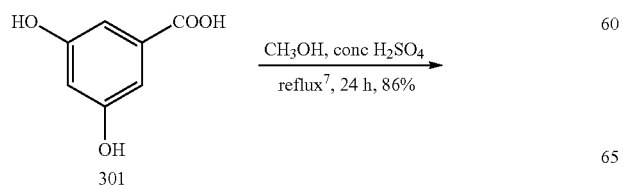

301

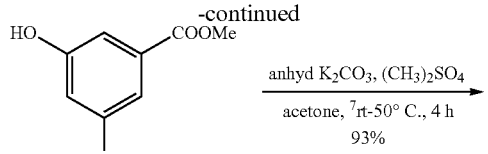

302

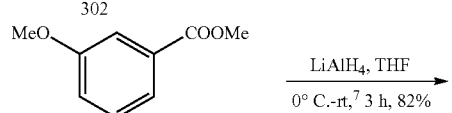

303

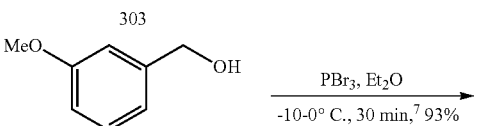

304

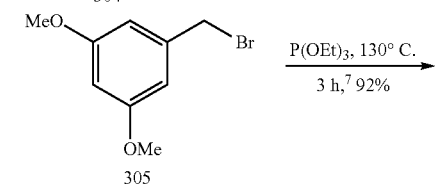

305

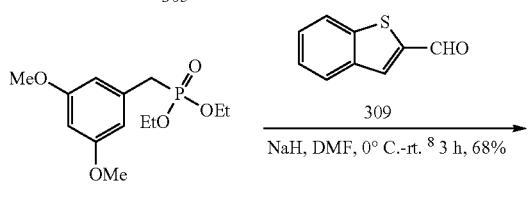

306

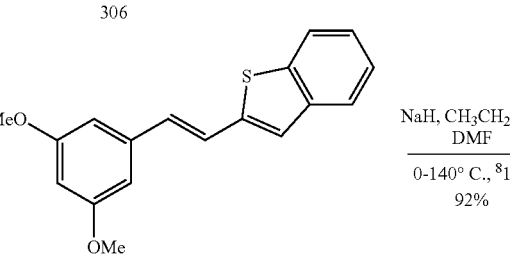

307

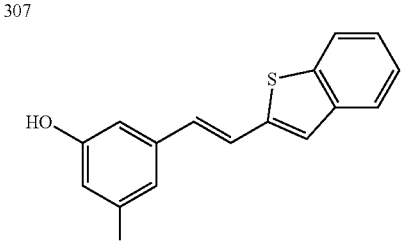

308
SK-03-92

3,5-Dihydroxy methylbenzoate (302)

Conc. $H_2SO_4$ (80 mL) was added slowly to a stirred solution of 3,5-dihydroxybenzoic acid 1 (50 g, 0.33 mol) in $CH_3OH$ (660 mL) at rt and this solution was heated to reflux for 24 h. The reaction mixture was cooled to rt and $H_2O$ (500 mL) was added to the solution. The solution was extracted with EtOAc (3×300 mL), and the combined organic extracts were washed with a saturated aq $NaHCO_3$ solution (2×300 mL). The organic layer was dried ($Na_2SO_4$), and concentrated under reduced pressure to afford a white crude powder. The crude solid was purified by flush column chromatography (FCC) (10% ethyl acetate in hexane) to afford a white powdered ester 302 (48 g, 86%): $^1$H NMR (300 MHz, $CDCl_3$) δ 7.10 (2H, d, J=2.4 Hz HAr), 6.57 (1H, t, J=2.0 Hz, HAr), 4.99, (2H, br, s, HO), 3.84 (3H, s, $H_3COO$). The spectral data for 302 were in excellent accord with data previously reported on 302 (Seidel et al., 1990)[1]. This material was employed directly in the next step.

3,5-Dimethoxy methylbenzoate (303)

The $(CH_3)_2SO_4$ (51.76 mL, 69 g, 0.547 mol) was added slowly to a stirred suspension of 302 (46 g, 0.27 mol) and anhydrous $K_2CO_3$ (94.45 g, 0.6835 mol) in acetone (700 mL) at rt and this mixture was heated to 50° C. and stirred for 48 h. Ice cold $H_2O$ (400 mL) was then added to the reaction mixture and the solution was extracted immediately with EtOAc (3×300 mL). The combined organic extracts were washed with brine (2×300 mL), dried ($Na_2SO_4$), and concentrated under reduced pressure to afford a yellow oil. The crude oil was purified by FCC (50% dichloromethane in hexane) to give a white powder 303 (92%), 303: $^1$H NMR (300 MHz, $CDCl_3$) δ 7.11 (2H, d, J=2.4 Hz HAr), 6.56 (1H, t, J=4.5 Hz, HAr), 3.91, (3H, s, $H_3COO$), 3.84 (6H, s, $H_3CO$). The spectral data for 303 were in excellent accord with data previously reported on this compound (Seidel et al., 1990)[1]. This material was employed directly in a later step.

3,5-Dimethoxy benzylalcohol (304)

Ester 303 (25 g, 0.13 mol) in THF (50 mL) was added slowly to a dry stirred suspension of $LiAlH_4$ (7.25 g 0.19 mol) in THF (550 mL) at 0° C. The reaction mixture was stirred for 3 h at rt at which time all the starting material had disappeared (TLC). The reaction mixture was quenched by addition of ice-cold $H_2O$ (1.0 eq), 10% aq NaOH (3.0 eq), and $H_2O$ (1.0 eq), sequentially and then filtered through a Buchner funnel. The filtrate was diluted with brine (800 mL) and extracted with EtOAc (3×300 mL). The combined organic extracts were dried ($Na_2SO_4$) and concentrated in vacuo. The crude oil was purified by FCC (20% ethylacetate in hexane) to afford a yellow oily alcohol 304 (17.5 g, 82%): $^1$H NMR (300 MHz, $CDCl_3$) δ 6.53 (2H, d, J=6.0 Hz HAr), 6.35 (1H, t, J=2.4 Hz, HAr), 4.49 (2H, s, $H_2COH$), 3.80 (6H, s, $H_3CO$). The spectral data for 304 were in excellent accord with data previously reported on it (Seidel et al., 1990)[1]. This material was employed directly in the next step.

3,5-Dimethoxy benzylbromide (305)

Phosphorus tribromide (0.4 eq) was added to the alcohol 304 (25 g, 0.13 mol) in THF (100 mL) very slowly at −10° C. and the mixture which resulted was stirred for 15-30 min at the same temperature. By this time all the starting material had disappeared (TLC). The reaction mixture was quenched by addition of ice-cold $H_2O$ (100 mL) and then filtered through a Buchner funnel. The filtrate was diluted with brine (100 mL) and extracted with EtOAc (3×300 mL). The combined organic extracts were dried ($Na_2SO_4$) and concentrated in vacuo. The crude oil was purified by FCC (20% ethylacetate in hexane) to afford the bromide 305 as a white solid (92%)[a]: $^1$H NMR (500 MHz, $CDCl_3$) δ 6.61 (2H, d, J=2.3 Hz), 6.46 (1H, t, J=2.3 Hz), 4.5 (2H, s), 3.85 (6H, s). $^{13}$C NMR (125 MHz, $CDCl_3$): δ 161.3, 140.2, 107.4, 101.0, 55.8, 34.1. The spectral data for 305 were in excellent accord with data previously reported on it (Seidel et al., 1990)[1]. This material was employed directly in the next step.

Synthesis of diethylbenzylphosphonate (306) and its conversion into the 3,5-dimethoxybenzothiostilbene (307)

Benzylbromide 305 (0.7 mL, 1.0 g, 5.85 mmol.) was heated with excess triethylphosphite (1.5 mL, 1.46 g, 8.76 mmol) at 130° C. under argon for 3 h while an outlet was set through the septum (16 guess needle) so that the volatile byproduct can be removed by evaporation during the reaction period. This gave phosphonate 306 (1.23 g, 92%), which was employed directly for the next step without any further purification[7].

Aldehyde 309 (1 g, 6.02 mmol) was added slowly to a combined solution of dry 3,5-dimethoxyethylbenzylphosphonate 306 (1.51 g, 6.62 mmol) and NaH (60% wt dispersed in mineral oil, 842 mg, 21.1 mmol) in dry DMF (5.0 mL), under argon at 0° C. This mixture was stirred at rt for 2 h, after which the reaction mixture was heated to 80-90° C. and stirred for an additional 1 h. The reaction solution was quenched by adding ice cold water slowly (25 mL) and extracted with EtOAc (50 mL×5). The total organic extract was washed with brine (100 mL×3), dried over $Na_2SO_4$ and evaporated on a rotatory evaporator. The crude solid which resulted was purified by FCC on silica gel (20% ethyl acetate in hexane) to afford pure 3,5-dimethoxybenzothiostilbene 307 (1.22 g, 85%) $^1$H NMR (300 MHz, $CDCl_3$) δ 7.82-7.71 (2H, m), 7.38-7.28 (4H, m), 6.96 (1H, d, J=15.9 Hz), 6.70 (2H, d, J=2.2 Hz), 6.45 (1H, t, J=2.2 Hz), 3.87 (6H, s). $^{13}$C NMR (75 MHz, $CDCl_3$): δ 161.5, 143.2, 140.7, 139.1, 131.3, 125.3, 125.0, 124.0, 123.9, 123.3, 122.7, 105.1, 101.0, 55.9. FIRMS (EI) (M)$^+$, Calcd. for $C_{18}H_{16}O_2S$ 296.0871; Found 296.0864.

(E)-3-(2-(Benzo[b]thiophen-2-yl)vinyl)-5-methoxyphenol 8, (SK-03-92)

The NaH (60% dispersed in mineral oil, 3.6 g, 0.090 mol) was added to anhydrous DMF (100 mL) at 0° C. The $CH_3CH_2SH$ (12.2 mL, 13.22 g, and 0.12 mol) was then added dropwise and stirred at 0° C. for 30 min. The temperature of the reaction mixure was allowed to rise to rt and the mixture stirred for 1 h. Then the temperature of the reaction mixture was raised to 140° C. and at 140° C. the 3,5-dimethoxybenzothiostilbene 307 (5.0 g, 0.03 mol) in dry DMF (30 mL) was added dropwise to the reaction mixture. This mixture was held at 140° C. and stirred for 1 h at this temperature. The reaction mixture was then cooled to rt and quenched by addition of brine (540 mL).This was followed by addition of formaldehyde (37% aq. 42 mL) and HOAc (68 mL). This mixture was extracted with EtOAc (3×200 mL). The combined organic layers were washed sequentially with a saturated aq solution of $NH_4Cl$ (3×60 mL), and with brine (3×60 mL). The organic layer was dried ($Na_2SO_4$), and the solvent was removed in vacuo. The crude oil was purified by FCC (20% ethylacetate in hexane) to afford the desired 3-hydroxy-5-methoxybenzothiostilbene 308 (92%) as a pale yellow solid: $^1$H NMR (300 MHz, $CD_3COCD_3$): δ 8.43 (1H, s), 7.89-7.77 (2H, m), 7.52-7.34 (4H, m), 6.97 (1H, d, J=15.9 Hz), 6.72 (2H, m), 6.40 (1H, t, J=2.2 Hz), 3.81 (3H, s). $^{13}$C NMR (75 MHz, $CD_3COCD_3$): δ 161.3, 158.7, 142.7, 140.3, 138.6, 130.8, 124.8, 124.5, 123.6, 123.4, 122.4, 122.0, 106.2, 103.4, 101.5, 54.6. HRMS (EI) (M)$^+$, Calcd. for $C_{17}H_{14}O_2S$ 282.0715; Found 282.0722. Anal. Calcd for $C_{17}H_{14}O_2S$ (MW: 282.36 g/mol): C, 72.31;H, 5.00; O, 11.33; S, 11.36. Found: C, 72.07; H, 4.99. Log P: 7.47; ClogP: 5.2962.

The organic layer was dried over anhydrous $MgSO_4$, and this was followed by concentration under reduced pressure to give a oily residue. It was further purified by column chromatog-

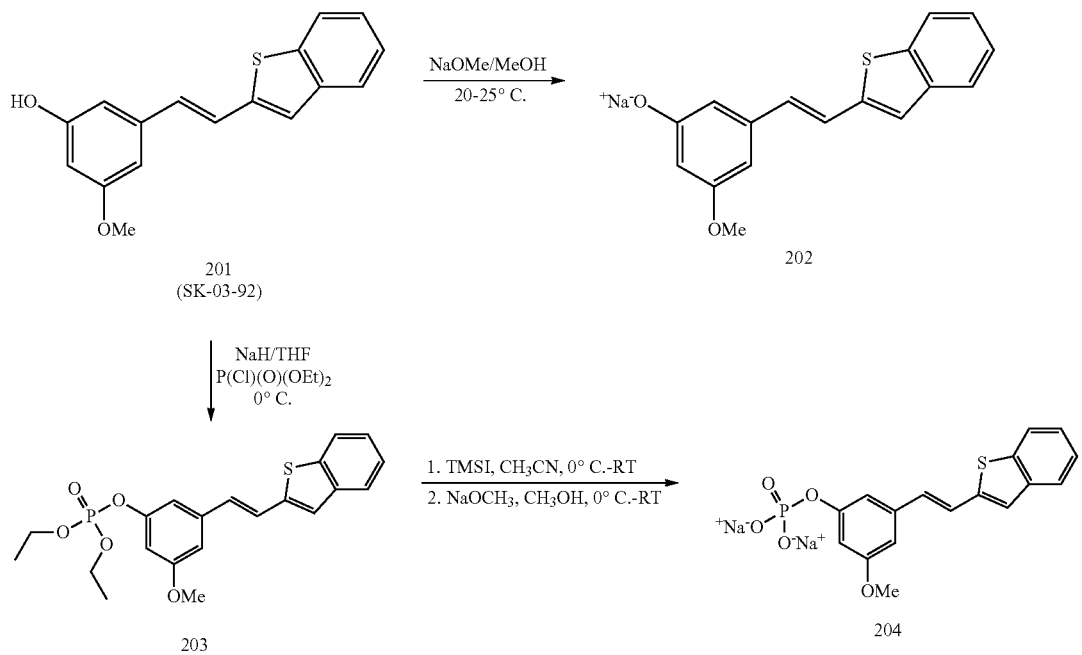

Scheme 11. Synthesis of SK-03-92 Salts

3-((E)-2-(Benzo[b]thiophen-2-yl)vinyl)-5-methoxyphenol sodium salt (202)

The 282 mg (1.0 mmole) of 201 was dissolved in 5 mL of dry methanol under anhydrous conditions at rt. To this stirred solution was added dropwise a solution of sodium methoxide (54 mg, 1.0 mmole) in 5 mL of dry methanol. The reaction solution was stirred for 1 hr after which, 10 mL of distilled water was added and solution was washed three times with dichloromethane (15 mL). The aq solution was then concentrated to dryness under reduced pressure to yield a white colored compound in 99% yield 202 (303 mg). $^1H$ NMR (300 MHz.) ($D_2O$) 7.84-7.82 (1H, m, benzothiazole C7-H), 7.76-7.74 (1H,m,benzothiazole C4-H), 7.38-7.35 (2H,m, benzothiazole C5 and C6), 7.34-7.31 (1H, d, J=9.5 Hz, HC=CH), 6.96-6.92 (1H, d, J=9.6 Hz, HC=CH),6.7-6.65 (2 h, m, 2Ar—H) and 6.42-6.41 (1H, t, Ar—H). $^{13}C$ NMR ($D_2O$) 161.60, 157.29, 143.03, 140.59, 139.40, 130.786, 125.29, 124.08, 123.48, 122.68, 106.43, 105.46, 101.89 and 55.87. LRMS [FAB+] (intensity %) [M+Na] 307 (40%), $M^+$304 (10%) other 282, 176 (100%) 154, 136.

3-((E)-2-(Benzo[b]thiophen-2-yl)vinyl)-5-methoxyphenyl diethyl phosphate (203)

To a solution of 201 (282 mg, 1.0 mmole) in 10 mL of dry THF, under an argon atmosphere at 0° C. was added with stirring, NaH (60% dispersion in oil) (44 mg, 1.1 mmole). The reaction mixture was stirred at 0° C. for 30 min after which Diethyl chlorophosphate (181 mg, 1.05 mmole) was added drop wise. The reaction mixture was allowed to warm to rt and stirred for 2 hr. The reaction progress was followed by TLC, after which the reaction was diluted with ether. The solution which resulted was washed with 10% aq sodium hydroxide. The organic layer was dried over anhydrous MgSO4, and this was followed by concentration under reduced pressure to give a oily residue. It was further purified by column chromatography to yield a yellow, colored oil 203 in 80% yield (335 mg). $^1H$ NMR (300 MHz.) ($CDCl_3$) 7.83-7.78 (1H, m benzothiazole C7-H), 7.69-7.43 (1 H,m,benzothiazole C4-H), 7.37-7.33 (2H,m, benzothiazole C5 and C6), 7.35-7.32 (1H, d,HC=CH), 6.96-6.92 (1H,d,HC=CH),6.86-6.83 (2 h,m, 2Ar—H) and 6.79-6.73 (1H,t,Ar—H), 4.31-4.24 (4H, q, 2×$CH_2$), 3.86 (3H,s, $OCH_3$), 1.42-1.37 (6H, t, 2×$CH_3$).

3-((E)-2-(Benzo[b]thiophen-2-yl)vinyl)-5-methoxyphenyl disodium phosphate (204)

To a solution of 203 (418 mg 1.0 mmole) in dry acetonitrile (10 mL) at 0° C. was added TMSI (500 mg, 2.5 mmole) with stirring. The reaction was warmed up to rt and stirred for 2 hrs. A solution of sodium methoxide (270 mg) in dry methanol 10 mL was added at 0° C. The reaction was again warmed to rt and stirred for 30 min. The solvent was then removed under reduced pressure to give a off white powder. It was dissolved in distilled water 10 mL and extracted three times with DCM (15 mL). The aq portion was then evaporated to dryness to yield the disodium phosphate salt 204 (220 mg) in 55% yield.

REFERENCES

1. Seidel, W. W. and Davidson D. W. J. Chem. Ecology 1990, 16, 1791-1870
2. Brendan, M. C.; Mori, Y.; Casey, C. M.; Datong, T.; Dale, L. B. J. Am. Chem. Soc. 2004, 126, 4310-4317
3. Takai, K.; Nitta, K.; Utimoto, K. J. Am. Chem. Soc. 1986, 108, 7408-7410
4. Wan, Z.; Jones, C. D.; Koenig, T. M.; Pu, Y. J.; Mitchell, D. Tetrahedron Letters 2003, 44, 8257-8259
5. Bachelor, F. W.; Loman, A. A.; Snowdon, L. R. Can. J. Chem. 1970, 48, 1554-1557

6. Palmgren, A.; Thorarensen, A.; Backvall, J. E. J. Org. Chem. 1998, 63, 3764-3768

7. Kabir, M. S.; Engelbrecht, K.; Polanowski, R.; Krueger, S. M.; Ignasiak, R.; Rott, M.; Schawan, W. R.; Stemper, M. E.; Reed, K. D.; Sherman, D.; Cook, J. M.; Monte, A.; "New Classes of Gram-positive Selective Antibacterials: Inhibitors of MRSA and Surrogates of The Causative Agents of Anthrax and Tuberculosis", *Bioorg. Med. Chem. Lett.,* 2008, 18, 5745-5749.

8. Monte A.; Kabir, M. S.; Cook, J. M.; Rott, M.; Schawn, W, Defoe, L., Anti-Infective Agents and Methods of Use, US Patent Application, US 2007/0292545 A1, Dec. 20, 2007, 37 pages.

We hereby claim:

1. A compound of Formula IV, or a salt or prodrug thereof:

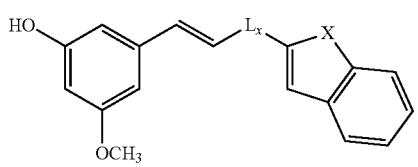

Formula (IV)

or salt and prodrug thereof, wherein X is selected from S, NH and O; and L is an optional linker or linking group selected from O, S, NH, $CF_2$, or $CH_2$, and x=0 or 1, i.e., if x=0, no linking group is present.

2. The compound according to claim 1, wherein said compound is selected from the group consisting of:

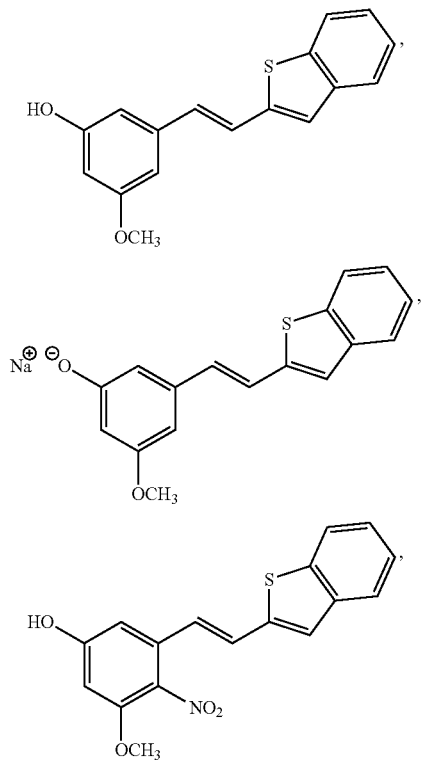

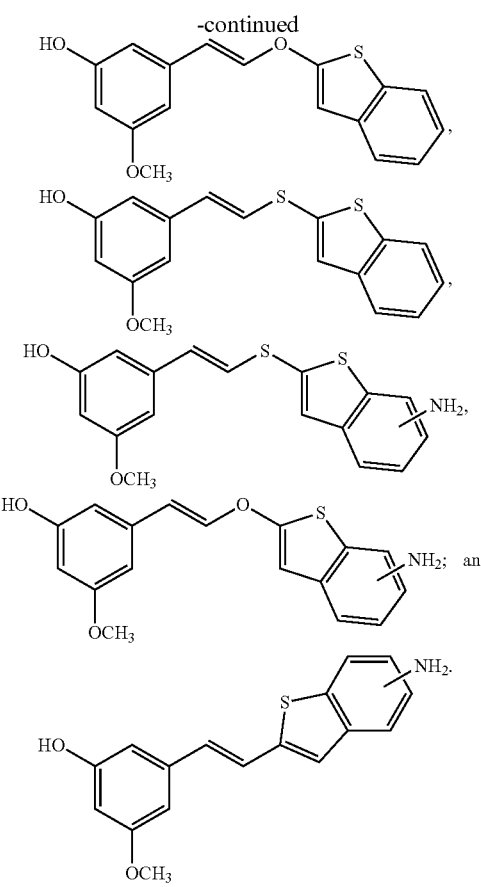

3. A method of treating infections or inhibiting microbial and/or helminth growth in a subject in need thereof, said method comprising the step of administering an effective amount of a compound having a structure represented by Formula IV or a salt or prodrug thereof.

4. The method according to claim 3, wherein said infection is caused by a bacterium.

5. The method according to claim 3, wherein said infection is caused by a helminth.

6. A pharmaceutical composition, comprising: (a) an effective amount of a compound having a chemical structure represented by Formula IV, or a salt or a prodrug thereof; and (b) a pharmaceutically-acceptable carrier.

7. The pharmaceutical composition of claim 6, wherein said compound is an anti-infective agent useful for the treatment of disease caused by a bacterium or a helminth.

8. The composition according to claim 7, wherein said bacterium is selected from the group consisting of *Staphylococcus aureus, Staphylococcus epidermidis, Streptococcus pneumoniae, Enterococcus faecalis, Bacillus cereus, Helicobacter pylori, Bacillus megaterium, Bacillus subtilis, Corynebacterium pseudodipthericum, Corynebacterium diphtheriae toxxerosis, Corynebacterium xerosisurealyticum, Enterococcus faecium* VRE 1, *Enterococcus faecium* VRE 14, *Enterococcus faecalis* ATCC 29212, *Staphylococcus aureus* ATCC 29213, *Staphylococcus aureus* ATCC 25923, *Staphylococcus aureus* MRSA MC-1, *Staphylococcus aureus* MRSA MC-4, *Streptococcus mitis, Streptococcus bovis, Streptococcus agalactiae, Streptococcus pyogenes, Streptococcus pneumoniae* ATCC 49619, *Listeria monocytogenes, Mycobacterium* bo vs BCG, *Mycobacterium tuberculosis, Brevibacillus* sp., *Clostridium difficile, Clostridium* novyi A, *Clostridium perfringens, Peptostreptococcus anaerobius, Mycobacterium bovis* BCG, *Mycobacterium avium, Mycobacterium chelonae, Mycobacterium fortuitum, Mycobacterium intracellulare, Mycobacterium kansasii*, and *Bacillus anthracis*.

9. The composition according to claim 8, wherein said bacterium is a Gram-positive bacterium or a *Mycobacterium*.

10. A method of inhibiting helminth growth, said method comprising contacting a bacterium to be inhibited with a helminth inhibiting amount of a compound, salt or prodrug according to:

a) Formula III

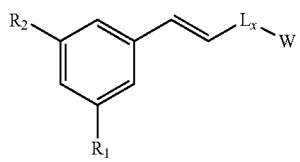

Formula (III)

wherein:
R$_1$ is not H when R$_2$ is H and R$_2$ is not H when R$_1$ is H, further wherein R$_1$ is OH or $CH^{(2n+1)}O$, wherein n is 1-10;
R$_2$ is OH or $CH_{(2n+1)}O$, where n is 1-10;
W is alkyl, phenyl, haylophenyl, pyridyl, piperidyl, or a substituted or unsubstituted aryl group, including unsubstituted and substituted aromatic heterocycles;
L is an optional linker or linking group selected from O, S, NH, CF$_2$, or CH$_2$, and x=0 or 1, i.e., if x=0, no linking group is present; and
when x=0, W is not phenyl; or b) Formula V

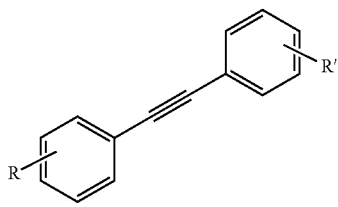

Formula (V)

wherein:
R is selected from the group consisting of hydroxyl, methoxy and combinations thereof;
R' is selected from the group consisting of H, hydroxy, alkyl, alkoxy, amino, nitro, halo, a substituted or unsubstituted aryl group, including certain unsubstituted and substituted aromatic heterocycles, and combinations thereof, wherein the compound is selected from the group consisting of:

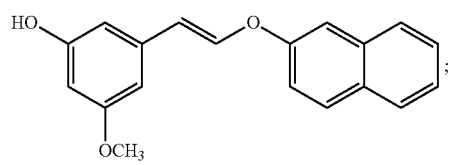

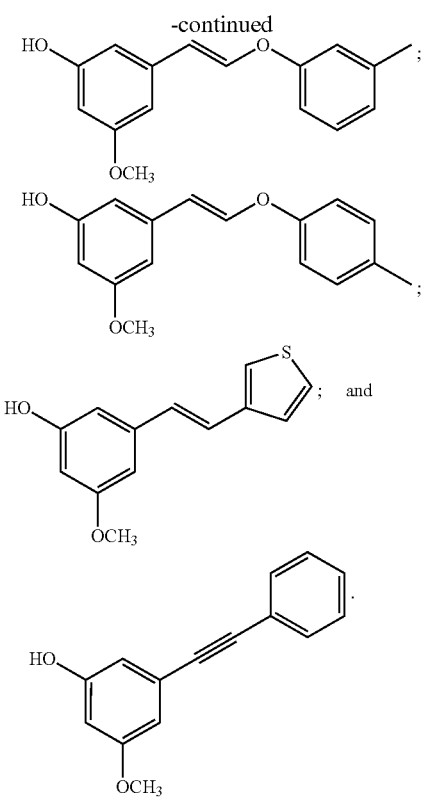

11. A composition suitable for inhibiting growth of microbes, wherein said composition comprises: a first ingredient which inhibits microbial growth comprising the compound, prodrug or salt of Formula III:

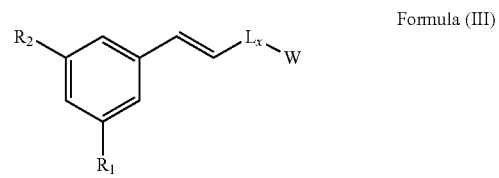

Formula (III)

wherein:
R$_1$ is not H when R$_2$ is H and R$_2$ is not H when R$_1$ is H, further wherein R$_1$ is OH or $CH_{(2n+1)}O$, wherein n is 1-10;
R$_2$ is OH or $CH_{(2n+1)}O$, where n is 1-10;
W is alkyl, phenyl, halophenyl, pyridyl, piperidyl, or a substituted or unsubstituted aryl group, including unsubstituted and substituted aromatic heterocycles;
L is an optional linker or linking group selected from O, S, NH, CF$_2$, or CH$_2$, and x=0 or 1, i.e., if x=0, no linking group is present and
when x=0, W is not phenyl; and
a second ingredient which comprises an acceptable carrier or an article of manufacture, wherein the first ingredient is (E)-3-(2-(benzo[b]thiophen-2-yl)vinyl)-5-methoxyphenol.

12. The composition according to claim 11, wherein the acceptable carrier is a pharmaceutically acceptable carrier, an antibacterial agent, a skin conditioning agent, a lubricating agent, a coloring agent, a moisturizing agent, binding and anti-cracking agent, a perfuming agent, a brightening agent, a UV absorbing agent, a whitening agent, a transparency imparting agent, a thixotropic agent, a solubilizing agent, an abrasive agent, an antioxidant, a skin healing agent, a cream, a lotion, an ointment, a shampoo, an emollient, a patch, a gel or a sol.

13. The composition according to claim 11, wherein the article of manufacture is a textile, a fiber, a glove or a mask.

\* \* \* \* \*